(12) United States Patent
Eid et al.

(10) Patent No.: US 12,343,360 B2
(45) Date of Patent: Jul. 1, 2025

(54) METHODS AND COMPOSITIONS FOR MICROBIAL ENGRAFTMENT

(71) Applicant: Pendulum Therapeutics, Inc., San Francisco, CA (US)

(72) Inventors: John S. Eid, San Francisco, CA (US); Colleen Cutcliffe, Menlo Park, CA (US); James H. Bullard, San Francisco, CA (US); Nicholas Justice, San Francisco, CA (US); Jessica Gines, San Francisco, CA (US); Surabhi Tyagi, San Francisco, CA (US); Marcus F. Schicklberger, Richmond, CA (US); Andrew T. Cheng, San Mateo, CA (US); Paul McMurdie, San Francisco, CA (US); Christian Sieber, San Francisco, CA (US)

(73) Assignee: Pendulum Therapeutics Inc, San Francisco, CA (US)

( * ) Notice: Subject to any disclaimer, the term of this patent is extended or adjusted under 35 U.S.C. 154(b) by 779 days.

(21) Appl. No.: 17/150,501

(22) Filed: Jan. 15, 2021

(65) Prior Publication Data

US 2021/0205374 A1 Jul. 8, 2021

Related U.S. Application Data

(63) Continuation of application No. PCT/US2019/042670, filed on Jul. 19, 2019.

(60) Provisional application No. 62/700,682, filed on Jul. 19, 2018.

(51) Int. Cl.
 A61K 35/74 (2015.01)
 A61K 38/28 (2006.01)
 A61P 37/06 (2006.01)

(52) U.S. Cl.
 CPC ............. *A61K 35/74* (2013.01); *A61K 38/28* (2013.01); *A61P 37/06* (2018.01)

(58) Field of Classification Search
 None
 See application file for complete search history.

(56) References Cited

U.S. PATENT DOCUMENTS

| | | |
|---|---|---|
| 3,625,214 A | 12/1971 | Higuchi |
| 4,789,734 A | 12/1988 | Pierschbacher |
| 4,897,268 A | 1/1990 | Tice et al. |
| 4,906,474 A | 3/1990 | Langer et al. |
| 4,925,673 A | 5/1990 | Steiner et al. |
| 5,075,109 A | 12/1991 | Tice et al. |
| 5,143,845 A | 9/1992 | Masuda et al. |
| 5,443,826 A | 8/1995 | Borody |
| 5,744,134 A | 4/1998 | Paul |
| 5,811,128 A | 9/1998 | Tice et al. |
| 5,814,344 A | 9/1998 | Tice et al. |
| 5,820,883 A | 10/1998 | Tice et al. |
| 5,853,763 A | 12/1998 | Tice et al. |
| 5,928,647 A | 7/1999 | Rock |
| 5,942,252 A | 8/1999 | Tice et al. |
| 6,028,098 A | 2/2000 | Goodman et al. |
| 6,241,983 B1 | 6/2001 | Paul et al. |
| 6,479,051 B1 | 11/2002 | Bruce et al. |
| 6,926,891 B1 | 8/2005 | Neeser et al. |
| 6,960,341 B2 | 11/2005 | Viscomi et al. |
| 7,033,764 B2 | 4/2006 | Korlach et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,101,565 B2 | 9/2006 | Monte |
| 7,183,101 B2 | 2/2007 | Arigoni et al. |
| 7,195,906 B2 | 3/2007 | Collins et al. |
| 7,307,062 B2 | 12/2007 | Bolte |
| 7,550,285 B2 | 6/2009 | Schiffrin et al. |
| 7,785,581 B2 | 8/2010 | Cui |
| 7,862,808 B2 | 1/2011 | Isolauri et al. |
| 7,947,482 B2 | 5/2011 | Molin et al. |
| 7,988,960 B2 | 8/2011 | Isolauri et al. |
| 8,192,733 B2 | 6/2012 | Cobb et al. |
| 8,329,672 B2 | 12/2012 | Rull Prous et al. |
| 8,343,482 B2 | 1/2013 | Bergonzelli et al. |
| 8,460,648 B2 | 6/2013 | Borody |
| 8,478,544 B2 | 7/2013 | Colwell et al. |
| 8,501,169 B2 | 8/2013 | Sanz Herranz et al. |
| 8,529,887 B2 | 9/2013 | Schiffrin |
| 8,557,233 B2 | 10/2013 | Macsharry et al. |
| 8,709,398 B2 | 4/2014 | Macsharry et al. |
| 8,728,794 B2 | 5/2014 | Miwa et al. |
| 8,734,783 B2 | 5/2014 | Mogna et al. |

(Continued)

FOREIGN PATENT DOCUMENTS

| | | |
|---|---|---|
| AU | 2012302364 A1 | 4/2014 |
| CA | 2851602 A1 | 3/2013 |

(Continued)

OTHER PUBLICATIONS

Abrahamsson, et al. Low Diversity of the Gut Microbiota in Infants with Atopic Eczema. J Allergy Clin. Immunol. 2012; 129:434-40.

(Continued)

*Primary Examiner* — Oluwatosin A Ogunbiyi
(74) *Attorney, Agent, or Firm* — Patent Law Works LLP

(57) ABSTRACT

The disclosure provides compositions and methods for therapeutic administration of the compositions to treat comorbidities associated with gut dysbiosis. The disclosure also provides compositions and methods for increasing engraftment of administered microbes. The disclosure also provides methods for stool sample collection.

7 Claims, 16 Drawing Sheets
Specification includes a Sequence Listing.

(56) References Cited

U.S. PATENT DOCUMENTS

| | | |
|---|---|---|
| 8,802,179 B2 | 8/2014 | Miller |
| 8,906,668 B2 | 12/2014 | Henn et al. |
| 8,951,512 B2 | 2/2015 | Blaser et al. |
| 9,011,834 B1 | 4/2015 | McKenzie et al. |
| 9,028,841 B2 | 5/2015 | Henn et al. |
| 9,040,101 B2 | 5/2015 | Heiman et al. |
| 9,168,275 B2 | 10/2015 | Finegold |
| 9,173,910 B2 | 11/2015 | Kaplan et al. |
| 9,180,147 B2 | 11/2015 | MckKenzie et al. |
| 9,192,179 B2 | 11/2015 | Roughead et al. |
| 9,192,554 B2 | 11/2015 | Guitard et al. |
| 9,259,447 B2 | 2/2016 | Burcelin et al. |
| 9,314,489 B2 | 4/2016 | Kelly et al. |
| 9,339,055 B2 | 5/2016 | Fujiwara et al. |
| 9,386,793 B2 | 7/2016 | Blaser et al. |
| 9,408,872 B2 | 8/2016 | Borody |
| 9,415,079 B2 | 8/2016 | Honda et al. |
| 9,421,230 B2 | 8/2016 | Honda et al. |
| 9,433,650 B2 | 9/2016 | Nieuwdorp et al. |
| 9,433,652 B2 | 9/2016 | Honda et al. |
| 9,439,933 B2 | 9/2016 | Masuoka et al. |
| 9,443,652 B2 | 9/2016 | Yoon et al. |
| 9,446,080 B2 | 9/2016 | McKenzie et al. |
| 9,463,169 B2 | 10/2016 | Heiman et al. |
| 9,486,487 B2 | 11/2016 | Cutcliffe et al. |
| 9,493,737 B2 | 11/2016 | Georgieva et al. |
| 9,533,014 B2 | 1/2017 | Henn et al. |
| 9,572,841 B2 | 2/2017 | Borody |
| 9,585,921 B2 | 3/2017 | McKenzie et al. |
| 9,603,876 B2 | 3/2017 | Blaser et al. |
| 9,623,055 B2 | 4/2017 | Nieuwdorp et al. |
| 9,623,056 B2 | 4/2017 | Borody |
| 9,642,881 B2 | 5/2017 | Honda et al. |
| 9,642,882 B2 | 5/2017 | Honda et al. |
| 9,644,210 B2 | 5/2017 | Schrezenmeir |
| 9,649,345 B2 | 5/2017 | Honda et al. |
| 9,649,346 B2 | 5/2017 | Klapper |
| 9,668,991 B1 | 6/2017 | Cahan |
| 9,668,992 B1 | 6/2017 | Cahan |
| 9,688,967 B2 | 6/2017 | Falb et al. |
| 9,710,606 B2 | 7/2017 | Apte et al. |
| 9,771,624 B2 | 9/2017 | Van Sinderen et al. |
| 9,833,484 B2 | 12/2017 | Mogna et al. |
| 10,149,867 B2 | 12/2018 | Kaplan et al. |
| 10,149,870 B2 | 12/2018 | Kaplan et al. |
| 10,668,116 B2 | 6/2020 | Cutcliffe et al. |
| 10,675,312 B2 | 6/2020 | Cutcliffe et al. |
| 10,729,732 B2 | 8/2020 | Kaplan et al. |
| 10,767,156 B2 | 9/2020 | Sorek et al. |
| 10,842,830 B2 | 11/2020 | Cutcliffe et al. |
| 10,842,831 B2 | 11/2020 | Cutcliffe et al. |
| 10,864,235 B2 | 12/2020 | Henn et al. |
| 11,096,971 B2 | 8/2021 | Possemiers |
| 11,213,556 B2 | 1/2022 | Cutcliffe et al. |
| 11,931,387 B2 | 3/2024 | Cutcliffe |
| 2002/0013270 A1 | 1/2002 | Bolte |
| 2004/0170617 A1 | 9/2004 | Finegold |
| 2005/0112112 A1 | 5/2005 | Park et al. |
| 2006/0115465 A1 | 6/2006 | Macfarlane et al. |
| 2007/0014756 A1 | 1/2007 | Touchot |
| 2007/0258953 A1 | 11/2007 | Duncan et al. |
| 2008/0038240 A1 | 2/2008 | Farmer et al. |
| 2008/0069861 A1 | 3/2008 | Brown et al. |
| 2008/0145341 A1 | 6/2008 | Myatt et al. |
| 2008/0182318 A1 | 7/2008 | Vanzin |
| 2008/0286252 A1 | 11/2008 | Sinnott |
| 2008/0311640 A1 | 12/2008 | Cox et al. |
| 2009/0010891 A1 | 1/2009 | Masuda et al. |
| 2009/0010892 A1 | 1/2009 | Masuda et al. |
| 2009/0010981 A1 | 1/2009 | Bechert et al. |
| 2009/0169531 A1 | 7/2009 | Lacoste et al. |
| 2009/0252708 A1 | 10/2009 | Fitzpatrick et al. |
| 2010/0086528 A1 | 4/2010 | Olofsson et al. |
| 2010/0086981 A1 | 4/2010 | LaTouf et al. |
| 2010/0087481 A1 | 4/2010 | Lee |
| 2010/0172874 A1 | 7/2010 | Turnbaugh et al. |
| 2010/0215738 A1 | 8/2010 | Ritter et al. |
| 2010/0284979 A1 | 11/2010 | O'Mahony et al. |
| 2010/0331641 A1 | 12/2010 | Bangera et al. |
| 2011/0081320 A1 | 4/2011 | Westall et al. |
| 2011/0287072 A1 | 11/2011 | Ritter et al. |
| 2012/0107291 A1 | 5/2012 | Burcelin et al. |
| 2012/0129794 A1 | 5/2012 | Dowd et al. |
| 2012/0165792 A1 | 6/2012 | Ortiz et al. |
| 2012/0183513 A1 | 7/2012 | Neu et al. |
| 2012/0183514 A1 | 7/2012 | Mercenier et al. |
| 2012/0230956 A1 | 9/2012 | McLean et al. |
| 2012/0238468 A1 | 9/2012 | Tuk et al. |
| 2013/0005586 A1 | 1/2013 | Ehrlich |
| 2013/0045874 A1 | 2/2013 | Ehrlich |
| 2013/0121968 A1 | 5/2013 | Quay |
| 2013/0143288 A1 | 6/2013 | Mullin et al. |
| 2013/0266539 A1 | 10/2013 | Borody |
| 2013/0280225 A1 | 10/2013 | Faure et al. |
| 2013/0296165 A1 | 11/2013 | Harel et al. |
| 2014/0037688 A1 | 2/2014 | Berkes et al. |
| 2014/0073610 A1 | 3/2014 | Ekwuribe |
| 2014/0079676 A1 | 3/2014 | Olmstead |
| 2014/0093478 A1 | 4/2014 | Turnbaugh et al. |
| 2014/0135398 A1 | 5/2014 | Matar et al. |
| 2014/0147417 A1 | 5/2014 | Sadowsky et al. |
| 2014/0286920 A1 | 9/2014 | Mayra-Makinen et al. |
| 2014/0341921 A1 | 11/2014 | Honda et al. |
| 2014/0363397 A1 | 12/2014 | Allen-Vercoe et al. |
| 2015/0209383 A1 | 7/2015 | Boileau et al. |
| 2015/0218507 A1 | 8/2015 | Georgieva et al. |
| 2015/0232801 A1 | 8/2015 | Yde et al. |
| 2015/0246081 A1 | 9/2015 | Morris |
| 2015/0258151 A1 | 9/2015 | Mani et al. |
| 2015/0259728 A1 | 9/2015 | Cutliffe et al. |
| 2015/0306152 A1 | 10/2015 | Cani et al. |
| 2015/0320808 A1 | 11/2015 | Burcelin et al. |
| 2015/0374760 A1 | 12/2015 | Scher et al. |
| 2016/0000838 A1 | 1/2016 | Harmsen et al. |
| 2016/0030494 A1 | 2/2016 | Henn et al. |
| 2016/0040215 A1 | 2/2016 | Henn et al. |
| 2016/0108442 A1 | 4/2016 | Adelstein et al. |
| 2016/0143961 A1 | 5/2016 | Berry et al. |
| 2016/0143962 A1 | 5/2016 | Berry et al. |
| 2016/0151432 A1 | 6/2016 | Borody |
| 2016/0151433 A1 | 6/2016 | Borody |
| 2016/0158294 A1 | 6/2016 | Von Maltzahn et al. |
| 2016/0193258 A1 | 7/2016 | Berry et al. |
| 2016/0199424 A1 | 7/2016 | Berry et al. |
| 2016/0228476 A1 | 8/2016 | Cutcliffe et al. |
| 2016/0232311 A1 | 8/2016 | Segal et al. |
| 2016/0232319 A1 | 8/2016 | Apte et al. |
| 2016/0243172 A1 | 8/2016 | Cook et al. |
| 2016/0243175 A1 | 8/2016 | Bushman et al. |
| 2016/0263144 A1 | 9/2016 | O'Hara et al. |
| 2016/0263153 A1 | 9/2016 | O'Hara |
| 2016/0263166 A1 | 9/2016 | Elinav et al. |
| 2016/0271188 A1 | 9/2016 | Berry et al. |
| 2016/0271189 A1 | 9/2016 | Cutcliffe et al. |
| 2016/0271190 A1 | 9/2016 | O'Hara et al. |
| 2016/0271191 A1 | 9/2016 | O'Hara |
| 2016/0287645 A1 | 10/2016 | O'Hara |
| 2016/0317432 A1 | 11/2016 | Garcia-Garcia et al. |
| 2016/0317653 A1 | 11/2016 | Cook et al. |
| 2016/0342735 A1 | 11/2016 | Apte et al. |
| 2016/0354417 A1 | 12/2016 | Smittle et al. |
| 2016/0354418 A1 | 12/2016 | Quintens et al. |
| 2016/0354509 A1 | 12/2016 | Parlato et al. |
| 2016/0355847 A1 | 12/2016 | Liu et al. |
| 2016/0367661 A1 | 12/2016 | Flavell et al. |
| 2016/0375068 A1 | 12/2016 | Borody |
| 2017/0000834 A1 | 1/2017 | Klosterbuer et al. |
| 2017/0007691 A1 | 1/2017 | Honda et al. |
| 2017/0020932 A1 | 1/2017 | Cutcliffe et al. |
| 2017/0027876 A1 | 2/2017 | Caillard |
| 2017/0042860 A1 | 2/2017 | Kashyap et al. |
| 2017/0058270 A1 | 3/2017 | Garcia-Garcia et al. |
| 2017/0067065 A1 | 3/2017 | Falb et al. |
| 2017/0080015 A1 | 3/2017 | Heiman et al. |

(56) References Cited

U.S. PATENT DOCUMENTS

| | | |
|---|---|---|
| 2017/0095517 A1 | 4/2017 | Mayra et al. |
| 2017/0101484 A1 | 4/2017 | Naeye et al. |
| 2017/0106026 A1 | 4/2017 | Kovarik |
| 2017/0112915 A1 | 4/2017 | Honda et al. |
| 2017/0119828 A1 | 5/2017 | Nakamura et al. |
| 2017/0143774 A1 | 5/2017 | Mulder et al. |
| 2017/0151290 A1 | 6/2017 | Blaser et al. |
| 2017/0151291 A1 | 6/2017 | Henn et al. |
| 2017/0157034 A1 | 6/2017 | Klapper |
| 2017/0165201 A1 | 6/2017 | Anselmo et al. |
| 2017/0165302 A1 | 6/2017 | Henn et al. |
| 2017/0273997 A1 | 9/2017 | Sakwinska et al. |
| 2017/0304375 A1 | 10/2017 | Kyle et al. |
| 2017/0312232 A1 | 11/2017 | Vitetta et al. |
| 2018/0094233 A1 | 4/2018 | Belzer et al. |
| 2018/0296613 A1 | 10/2018 | O'Mahony |
| 2018/0357375 A1 | 12/2018 | Cutcliffe et al. |
| 2019/0030096 A1 | 1/2019 | Cutcliffe et al. |
| 2019/0038678 A1 | 2/2019 | De Vos |
| 2019/0046590 A1 | 2/2019 | Kaplan et al. |
| 2019/0070227 A1 | 3/2019 | Cutcliffe et al. |
| 2019/0070228 A1 | 3/2019 | Cutcliffe et al. |
| 2020/0121733 A1 | 4/2020 | Kaplan et al. |
| 2020/0121734 A1 | 4/2020 | Kaplan et al. |
| 2020/0121735 A1 | 4/2020 | Kaplan et al. |
| 2020/0121736 A1 | 4/2020 | Kaplan et al. |
| 2020/0121738 A1 | 4/2020 | Cutcliffe et al. |
| 2020/0237835 A1 | 7/2020 | Kaplan et al. |
| 2020/0246395 A1 | 8/2020 | Kaplan et al. |
| 2020/0261517 A1 | 8/2020 | Cutcliffe et al. |
| 2020/0345796 A1 | 11/2020 | Cutcliffe et al. |
| 2021/0038654 A1 | 2/2021 | Culler |
| 2021/0386798 A1 | 12/2021 | Cutcliffe et al. |
| 2022/0002665 A1 | 1/2022 | Ko |
| 2022/0133812 A1 | 5/2022 | Seo |
| 2022/0211780 A1 | 7/2022 | Kolterman |

FOREIGN PATENT DOCUMENTS

| | | |
|---|---|---|
| CN | 101410128 A | 4/2009 |
| CN | 102448477 A | 5/2012 |
| CN | 102458415 A | 5/2012 |
| CN | 104244733 A | 12/2014 |
| CN | 105030841 A | 11/2015 |
| CN | 105106245 A | 12/2015 |
| EP | 0456418 A2 | 11/1991 |
| EP | 0446069 B1 | 9/1993 |
| EP | 0456418 B1 | 9/1996 |
| EP | 1600060 A1 | 11/2005 |
| EP | 1359924 B1 | 10/2007 |
| EP | 2030623 A1 | 3/2009 |
| EP | 2439264 A1 | 4/2012 |
| EP | 2442814 A2 | 4/2012 |
| EP | 2318513 B1 | 9/2012 |
| EP | 1680501 B1 | 12/2012 |
| EP | 2117567 B1 | 6/2014 |
| EP | 2753187 A1 | 7/2014 |
| EP | 2836224 A2 | 2/2015 |
| EP | 2766026 A4 | 5/2015 |
| EP | 2789340 A4 | 7/2015 |
| EP | 2556835 B1 | 8/2015 |
| EP | 2919796 A1 | 9/2015 |
| EP | 2951285 A1 | 12/2015 |
| EP | 2953472 A1 | 12/2015 |
| EP | 2953474 A2 | 12/2015 |
| EP | 2956006 A2 | 12/2015 |
| EP | 2988761 A1 | 3/2016 |
| EP | 3052111 A1 | 8/2016 |
| EP | 3058085 A2 | 8/2016 |
| EP | 3074027 A1 | 10/2016 |
| EP | 3102670 A4 | 7/2017 |
| EP | 3223834 A2 | 10/2017 |
| EP | 3135754 A4 | 12/2017 |
| FR | 2874825 A1 | 3/2006 |
| JP | H08298982 A | 11/1996 |
| JP | 2006314219 A | 11/2006 |
| JP | 2007031291 A | 2/2007 |
| JP | 2010126457 | 6/2010 |
| JP | 5019563 B2 | 9/2012 |
| JP | 2014527068 A | 10/2014 |
| JP | 2015537042 A | 12/2015 |
| JP | 2017535597 A | 11/2017 |
| JP | 2018-502926 | 2/2018 |
| KR | 20140128936 A | 11/2014 |
| KR | 20200040277 A | 4/2020 |
| RU | 2014112223 A | 10/2015 |
| WO | WO-199001335 A1 | 2/1990 |
| WO | WO-0015760 A1 | 3/2000 |
| WO | WO-0188095 A1 | 11/2001 |
| WO | WO-0193904 A1 | 12/2001 |
| WO | WO-0197822 A1 | 12/2001 |
| WO | WO-0207741 A1 | 1/2002 |
| WO | WO-03070203 A1 | 8/2003 |
| WO | WO-2004085628 A1 | 10/2004 |
| WO | WO-2005055934 A2 | 6/2005 |
| WO | WO-2006000992 A1 | 1/2006 |
| WO | WO-2006013441 A2 | 2/2006 |
| WO | WO-2007046697 A1 | 4/2007 |
| WO | WO-2007046699 A2 | 4/2007 |
| WO | WO-2007125566 A2 | 11/2007 |
| WO | WO-2008076696 A2 | 6/2008 |
| WO | WO-2009018447 A2 | 2/2009 |
| WO | WO-2009024429 A2 | 2/2009 |
| WO | WO-2009077352 A1 | 6/2009 |
| WO | WO-2009153662 A1 | 12/2009 |
| WO | WO-2010036876 A2 | 4/2010 |
| WO | WO-2010108865 A1 | 9/2010 |
| WO | WO-2010146568 A2 | 12/2010 |
| WO | WO-2011043654 A1 | 4/2011 |
| WO | WO-2010146568 A3 | 5/2011 |
| WO | WO-2011096809 A1 | 8/2011 |
| WO | WO-2011099514 A1 | 8/2011 |
| WO | WO-2011135194 A2 | 11/2011 |
| WO | WO-2012021678 A2 | 2/2012 |
| WO | WO-2012024638 A2 | 2/2012 |
| WO | WO-2012033814 A2 | 3/2012 |
| WO | WO-2012089782 A1 | 7/2012 |
| WO | WO-2012122478 A1 | 9/2012 |
| WO | WO-2012142605 A2 | 10/2012 |
| WO | WO-2013032328 A1 | 3/2013 |
| WO | WO-2013050792 A1 | 4/2013 |
| WO | WO-2013050833 A1 | 4/2013 |
| WO | WO-2013107913 A1 | 7/2013 |
| WO | WO-2013130773 A2 | 9/2013 |
| WO | WO-2013175038 A1 | 11/2013 |
| WO | WO-2013191845 A1 | 12/2013 |
| WO | WO-2014011233 A1 | 1/2014 |
| WO | WO-2014070014 A1 | 5/2014 |
| WO | WO-2014075745 A1 | 5/2014 |
| WO | WO-2014076246 A1 | 5/2014 |
| WO | WO-2014082050 A1 | 5/2014 |
| WO | WO-2014121298 A2 | 8/2014 |
| WO | WO-2014121301 A1 | 8/2014 |
| WO | WO-2014121302 A2 | 8/2014 |
| WO | WO-2014121304 A1 | 8/2014 |
| WO | WO-2014137211 A1 | 9/2014 |
| WO | WO-2014145958 A2 | 9/2014 |
| WO | WO-2014151565 A1 | 9/2014 |
| WO | WO-2014152338 A1 | 9/2014 |
| WO | WO-2014153194 A2 | 9/2014 |
| WO | WO-2014121302 A3 | 10/2014 |
| WO | WO-2014201037 A2 | 12/2014 |
| WO | WO-2014153194 A4 | 1/2015 |
| WO | WO-2015013214 A2 | 1/2015 |
| WO | WO-2015051323 A1 | 4/2015 |
| WO | WO-2015059690 A1 | 4/2015 |
| WO | WO-2015067936 A1 | 5/2015 |
| WO | WO-2015067938 A1 | 5/2015 |
| WO | WO-2015067947 A1 | 5/2015 |
| WO | WO-2015067948 A1 | 5/2015 |
| WO | WO-2015067949 A1 | 5/2015 |
| WO | WO-2015077794 A1 | 5/2015 |
| WO | WO-2015088227 A1 | 6/2015 |
| WO | WO-2015095241 A2 | 6/2015 |

(56) References Cited

FOREIGN PATENT DOCUMENTS

| | | |
|---|---|---|
| WO | WO-2015131076 A1 | 9/2015 |
| WO | WO-2015166489 A2 | 11/2015 |
| WO | WO-2015166492 A2 | 11/2015 |
| WO | WO-2015095241 A4 | 12/2015 |
| WO | WO-2015189472 A1 | 12/2015 |
| WO | WO-2016013921 A2 | 1/2016 |
| WO | WO-2016065419 A1 | 5/2016 |
| WO | WO-2016070151 A1 | 5/2016 |
| WO | WO-2016079731 A2 | 5/2016 |
| WO | WO-2016084029 A1 | 6/2016 |
| WO | WO-2016110585 A1 | 7/2016 |
| WO | WO-2016118730 A1 | 7/2016 |
| WO | WO-2016139217 A1 | 9/2016 |
| WO | WO-2016149149 A1 | 9/2016 |
| WO | WO-2016149687 A1 | 9/2016 |
| WO | WO-2016174677 A1 | 11/2016 |
| WO | WO-2016176380 A1 | 11/2016 |
| WO | WO-2016177797 A1 | 11/2016 |
| WO | WO-2016177801 A1 | 11/2016 |
| WO | WO-2016185469 A1 | 11/2016 |
| WO | WO-2016186243 A1 | 11/2016 |
| WO | WO-2016194427 A1 | 12/2016 |
| WO | WO-2016196440 A1 | 12/2016 |
| WO | WO-2016201053 A1 | 12/2016 |
| WO | WO-2017009187 A1 | 1/2017 |
| WO | WO-2017019273 A1 | 2/2017 |
| WO | WO-2017024237 A1 | 2/2017 |
| WO | WO-2017032897 A1 | 3/2017 |
| WO | WO-2017035188 A1 | 3/2017 |
| WO | WO-2017035412 A1 | 3/2017 |
| WO | WO-2017041039 A1 | 3/2017 |
| WO | WO-2017042347 A1 | 3/2017 |
| WO | WO-2017047968 A1 | 3/2017 |
| WO | WO-2017060468 A1 | 4/2017 |
| WO | WO-2017060698 A1 | 4/2017 |
| WO | WO-2017063066 A1 | 4/2017 |
| WO | WO-2017075098 A1 | 5/2017 |
| WO | WO-2017079450 A1 | 5/2017 |
| WO | WO-2017091783 A2 | 6/2017 |
| WO | WO-2017097987 A1 | 6/2017 |
| WO | WO-2017102816 A1 | 6/2017 |
| WO | 2017146580 | 8/2017 |
| WO | WO-2017130859 A1 | 8/2017 |
| WO | WO-2017134240 A1 | 8/2017 |
| WO | WO-2017159643 A1 | 9/2017 |
| WO | WO-2018106844 A1 | 6/2018 |
| WO | WO-2019046646 A1 | 3/2019 |
| WO | 2021094993 A1 | 5/2021 |
| WO | 2023020831 A1 | 2/2023 |
| WO | 2023161303 A1 | 8/2023 |
| WO | 2023178194 A2 | 9/2023 |

OTHER PUBLICATIONS

Agarwal, et al. The current and future state of companion diagnostics. Pharmgenomics Pers Med. Mar. 31, 2015;8:99-110. doi: 10.2147/PGPM.S49493. eCollection 2015.

Alger, et al. Multisite, multimodal neuroimaging of chronic urological pelvic pain: Methodology of the MAPP Research Network. Neuroimage Clin. Jan. 6, 2016;12:65-77. doi: 10.1016/j.nicl.2015.12.009. eCollection 2016.

Allen, et al. Probiotic May Help Alleviate Stress-Related Conditions. Society for Neuroscience (SfN) 2015 Annual Meeting. Abstract 162.04. Presented Oct. 18, 2015.

Allin, et al. Aberrant intestinal microbiota in individuals with prediabetes. Diabetologia. Jan. 29, 2018. doi: 10.1007/s00125-018-4550-1. [Epub ahead of print].

Amar, et al. (2011). Intestinal mucosal adherence and translocation of commensal bacteria at the early onset of type 2 diabetes: molecular mechanisms and probiotic treatment. EMBO Mol. Med. 3, 559-572. doi: 10.1002/emmm. 201100159.

American Chemical Society. "No guts no glory: Harvesting the microbiome of athletes." ScienceDaily. ScienceDaily, Aug. 20, 2017. www.sciencedaily.com/releases/2017/08/170820075017.htm.

Angelakis, et al. The relationship between gut microbiota and weight gain in humans. Future Microbiol. Jan. 2012;7(1):91-109. doi: 10.2217/fmb.11.142.

Anonymous. Allergies; New findings from Hokkaido University describe advances in allergies. Clinical Trials Week [Atlanta] (Mar. 22, 2010): 42.

Anonymous. Clostridium; New clostridium data have been reported by scientists at Ghent University. Science Letter [Atlanta] (Aug. 17, 2010): 1811.

Anonymous. Nutrition; Research on nutrition detailed by scientists at Institute of Agrochemistry and Food Technology. Obesit, Fitness & Wellness Week [Atlanta] (Jul. 17, 2010): 2819.

Ansel, Howard C, et al. Pharmaceutical Dosage Forms and Drug Delivery Systems. Philadelphia, PA: Lippincott-Williams & Wilkins, 1999. Print.

Arora, et al., Propionate Anti-Obesity and Satiety Enhancing Factor? Appetite, Apr. 2011, 56(2):511-5.

Asano, et al. Critical role of gut microbiota in the production of biologically active, free catecholamines in the gut lumen of mice. Am J Physiol Gastrointest Liver Physiol. Dec. 1, 2012;303(11):G1288-95. doi: 10.1152/ajpgi.00341.2012. Epub Oct. 11, 2012.

ATCC Catalogue, accessed Dec. 14, 2017. https://www.atcc.org/Search_Results.aspx?dsNav=Ntk:PrimarySearch°/07cClostridium+beijerinckii°/07c3 )/07c,NY:True, Rpp:100, N : 1000552&searchTerms=Clostridium+beijerinckii&redir=1.

Athauda, et al. Exenatide once weekly versus placebo in Parkinson's disease: a randomised, double-blind, placebo-controlled trial. Lancet. Aug. 3, 2017. pii: S0140-6736(17)31585-4. doi: 10.1016/S0140-6736(17)31585-4. [Epub ahead of print].

Atlas. Handbook of Microbiological Media. Fourth Edition. CRC Press. 2010.

Ausubel, et al. eds. Current Protocols in Molecular Biology. United States. Greene Publishing Associates and Wiley-Interscience. 1987. (Table of Contents).

Axling, et al. Green tea powder and Lactobacillus plantarum affect gut microbiota, lipid metabolism and inflammation in high-fat fed C57BL/6J mice. Nutr Metab (Lond). Nov. 26, 2012;9(1):105. doi: 10.1186/1743-7075-9-105.

Aziz, et al. Changes in gut hormones and fecal bacterial community composition in response to diet-induced obesity in the rat. Obesity, suppl. 1 19 (Nov. 2011): S166-S167.

Bach, et al. The presence of HLA-B27 shapes gut microbiome composition in rats. Arthritis and Rheumatism, suppl. 10 64 (Oct. 2012): S1052-S1053.

Backhed, et al., Mechanisms underlying the resistance to diet-induced obesity in germ-free mice, PNAS, Jan. 16, 2007, 104(3):979-84.

Backhed, et al., The gut microbiota as an environmentalfactor that regulates fat storage, PNAS, Nov. 2, 2004, 101(44):15718-23.

Baffoni, et al. Effect of dietary supplementation of Bifidobacterium and Lactobacillus strains in *Apis mellifera* L. against Nosema ceranae. Benef Microbes. Nov. 13, 2015:1-8. [Epub ahead of print].

Baker. The role of microorganisms in atopic dermatitis. Clin Exp Immunol. Apr. 2006;144(1):1-9.

Barcenilla, et al. Phylogenetic relationships of butyrate-producing bacteria from the human gut. Appl Environ Microbiol. Apr. 2000. 66(4):1654-61.

Baviera, et al. Microbiota in Healthy Skin and in Atopic Eczema. Hindawi Publishing Corporation, BioMed Research International, vol. 2014.

BD Diagnostics. Media Solutions for Microbial and Molecular Genetics Research Applications. Jul. 2009.

Belenguer, et al. Impact of pH on Lactate Formation and Utilization by Human Fecal Microbial Communities. Appl Environ Microbiol. Oct. 2007; 73(20): 6526-6533. Published online Aug. 31, 2007. doi: 10.1128/AEM.00508-07.

Belenguer, et al. Two routes of metabolic cross-feeding between Bifidobacterium adolescentis and butyrate-producing anaerobes from the human gut. Appl Environ Microbiol. May 2006;72(5):3593-3599. doi: 10.1128/AEM.72.5.3593-3599.2006.

(56) References Cited

OTHER PUBLICATIONS

Belzer, et al. (2012). Microbes inside-from diversity to function: the case of Akkermansia. ISME J. 6, 1449-1458. doi: 10.1038/ismej.2012.6.

Ben-Amor, et al. Genetic diversity of viable, injured, and dead fecal bacteria assessed by fluorescence-activated cell sorting and 16S rRNA gene analysis. Appl Environ Microbiol. Aug. 2005;71(8):4679-89. doi: 10.1128/AEM.71.8.4679-4689.2005.

Berridge. 'Liking' and 'wanting' food rewards: brain substrates and roles in eating disorders. Physiol Behav. Jul. 14, 2009;97(5):537-50. doi: 10.1016/j.physbeh.2009.02.044. Epub Mar. 29, 2009.

Berry, et al, Phylotype-level 16S rRNA analysis reveals new bacterial indicators of health state in acute murine colitis, ISME Journal 6.11 (Nov. 2012): 2091-2106.

Beye, et al. Careful use of 16S rRNA gene sequence similarity values for the identification of *Mycobacterium* species. New Microbes New Infect. Dec. 29, 2017;22:24-29. doi: 10.1016/j.nmni.2017.12.009. eCollection Mar. 2018.

Bick, et al.From research to clinical practice: implementation of functional magnetic imaging and white matter tractography in the clinical environment. J Neurol Sci. Jan. 15, 2012;312(1-2):158-65. doi: 10.1016/j.jns.2011.07.040. Epub Aug. 23, 2011.

Bjelland, et al. The validity of the Hospital Anxiety and Depression Scale. An updated literature review. J Psychosom Res. Feb. 2002;52(2):69-77.

BMS acquires Amylin Pharmaceuticals, expands diabetes alliance with AstraZeneca. Jul. 2, 2012. 4 pages. http://www.centerwatch.com/news-online/2012/07/02/bms-acquires-amylin-pharmaceuticals-expands-diabetes-alliance-with-astrazeneca/.

Bourassa, et al., Butyrate, neuroepigenetics and the gut microbiome: can a high fiber diet improve brain health, Neuroscience Letters, 2016, 625:56-63.

Bourhis, et al. Contribution of C. beijerinckii and C. sporogenes in association with C. tyrobutyricum to the butyric fermentation in Emmental type cheese. International Journal of Food Microbiology. 113 (2007) 154-163.

Bouter, et al. Differential metabolic effects of oral butyrate treatment in lean versus metabolic syndrome subjects. Clin Transl Gastroenterol. May 25, 2018. 9(5):155. doi: 10.1038/s41424-018-0025-4.

Bowman, et al. Analysis of Full-Length Metagenomic 16S Genes by SMRT Sequencing. American Society for Microbiology 2013 General Meeting May 19, 2013 Poster Session, pp. 116 Poster 390. Available on the internet: http://files.pacb.com/pdf/Analysis_of_Full_Length_Metagenomic_16S_Genes_by_SMRT_Sequencing.pdf.

Bravo, Ingestion of Lactobacillus strain regulates emotional behavior and central GABA receptor expression in a mouse via the vagus nerve. Proc Natl Acad Sci U S A. Sep. 20, 2011;108(38):16050-5. doi: 10.1073/pnas.1102999108. Epub Aug. 29, 2011.

Brown. "Akkermansia: new discoveries from the microbiome", Functional Medicine, Masterclass, Sep. 20, 2014, XP055327009.

Brown et al. Chemical synthesis and cloning of a tyrosine tRNA gene. Methods Enzymol. 68:109-51 (1979).

Brun, et al. (2013). Toll-like receptor 2 regulates intestinal inflammation by controlling integrity of the enteric nervous system. Gastroenterology 145, 1323-1333. doi: 10.1053/j.gastro.2013.08.047.

Bueter; et al, "Gastric Bypass Increases Energy Expenditure in Rats. Gastroenterology", Gastroenterology, Gastroenterology, 2010, 138(5), 1845-1853.

Buhwald et al. (2004), "Bariatric Surgery: A Systematic Review and Meta-Analysis", JAMA, 292 (14): 1724-1737.

Burger, et al. A functional neuroimaging review of obesity, appetitive hormones and ingestive behavior. Physiol Behav. Sep. 2014;136:121-7. doi: 10.1016/j.physbeh.2014.04.025. Epub Apr. 21, 2014.

Canani, et al. Potential beneficial effects of butyrate in intestinal and extraintestinal diseases. World J. Gastroenterol., Mar. 28, 2011; 17 (12): 1519-1528.

Candela, et al, Unbalance of intestinal microbiota in atopic children, BMC Microbiology 12 (Jun. 6, 2012).

Cani, et al. (2004). Inulin-type fructans modulate gastrointestinal peptides involved in appetite regulation (glucagon-like peptide-1 and ghrelin) in rats. Br. J. Nutr. 92, 521-526. doi: 10.1079/BJN20041225.

Cani, et al. (2006). Improvement of glucose tolerance and hepatic insulin sensitivity by oligofructose requires a functional glucagon-like peptide 1 receptor. Diabetes Metab. Res. Rev. 55, 1484-1490. doi: 10.2337/db05-1360.

Cani, et al. (2007). Metabolic endotoxemia initiates obesity and insulin resistance. Diabetes Metab. Res. Rev. 56, 1761-1772. doi: 10.2337/db06-1491.

Cani, et al. (2009). Changes in gut microbiota control inflammation in obese mice through a mechanism involving GLP-2-driven improvement of gut permeability. Gut 58, 1091-1103. doi: 10.1136/gut.2008.165886.

Cani, et al., Changes in Gut Microbia Control Metabolic Endotoxemia-Induced Inflammation in High-Fat Diet-Induced Obesity and Diabetes in Mice, Diabetes, 2008, 57(6):1470-81.

Cani, et al. Involvement of gut microbiota in the development of low-grade inflammation and type 2 diabetes associated with obesity. Gut Microbes. Jul.-Aug. 2012;3(4):279-288. doi: 10.4161/gmic.19625. Epub May 14, 2012.

Cani et al. Next-Generation Beneficial Microbes: The Case of Akkermansia muciniphila. Front Microbiol. Sep. 22, 2017;8:1765. doi: 10.3389/fmicb.2017.01765. eCollection 2017.

Cani. Gut microbiota, low grade inflammation and metabolism. Appetite, suppl. 1 59 Jul. 2012: e11.

Cappelleri, et al. Psychometric analysis of the Three-Factor Eating Questionnaire-R21: results from a large diverse sample of obese and non-obese participants. Int J Obes (Lond). Jun. 2009;33(6):611-20. doi: 10.1038/ijo.2009.74. Epub Apr. 28, 2009.

Caricilli, et al. (2011). Gut microbiota is a key modulator of insulin resistance in TLR 2 knockout mice. PLOS Biol. 9:e1001212. doi: 10.1371/journal.pbio.1001212.

Casellas, et al, Defective Akkermansia Muciniphila in Feces of Ulcerative Colitis Patients, Northern Light Life Sciences Conference Abstracts (Oct. 24, 2011).

Chao, et al. Food cravings, food intake, and weight status in a community-based sample. Eat Behav. Aug. 2014;15(3):478-82. doi: 10.1016/j.eatbeh.2014.06.003. Epub Jun. 18, 2014.

Chen, et al. Bifidobacterium adolescentis supplementation ameliorates visceral fat accumulation and insulin sensitivity in an experimental model of the metabolic syndrome. Br J Nutr. May 2012;107(10):1429-34. doi: 10.1017/S0007114511004491. Epub Sep. 14, 2011.

Chethankumar, et al. Butyric acid modulates activities of intestinal and renal disaccharidases in experimentally induced diabetic rats. Nahrung. Oct. 2002;46(5):345-8. doi: 10.1002/1521-3803(20020901)46:5 345::Aid-Food3453.0.CO;2-7.

Chia, et al. (2018) "Deciphering the trophic interaction between Akkermansia muciniphila and the butyrogenic gut commensal Anaerostipes caccae using a metatranscriptomic approach," Antonie Van Leeuwenhoek, vol. 111, No. 6, pp. 859-873.

Chin, et al. Nonhybrid, finished microbial genome assemblies from long-read SMRT sequencing data. Nat Methods. Jun. 2013;10(6):563-9. doi: 10.1038/nmeth.2474. Epub May 5, 2013.

Clayton. Metabolic differences underlying two distinct rat urinary phenotypes, a suggested role for gut microbial metabolism of phenylalanine and a possible connection to autism. FEBS Lett. Apr. 5, 2012;586(7):956-61. doi: 10.1016/j.febslet.2012.01.049. Epub Feb. 1, 2012.

Collado, et al. (2007). Intestinal integrity and Akkermansia muciniphila, a mucin-degrading member of the intestinal microbiota present in infants, adults, and the elderly. Appl. Environ. Microbiol. 73, 7767-7770. doi: 10.1128/AEM.01477-07.

Cork, et al. Epidermal Barrier Dysfunction in Atopic Dermatitis. J Invest Dermatol. Aug. 2009; 129(8):1892-908. doi: 10.1038/jid.2009.133. Epub Jun. 4, 2009.

Costello, et al. Postprandial remodeling of the gut microbiota in Burmese pythons. ISME J. Nov. 2010;4(11):1375-85. doi: 10.1038/ismej.2010.71. Epub Jun. 3, 2010.

(56) References Cited

OTHER PUBLICATIONS

Cryan, et al. Mind-altering microorganisms: the impact of the gut microbiota on brain and behaviour. Nat Rev Neurosci. Oct. 2012;13(10):701-12. doi: 10.1038/nrn3346. Epub Sep. 12, 2012.
Culligan, et al, Functional metagenomics reveals novel salt tolerance loci from the human gut microbiome. ISME Journal 6.10 (Oct. 2012): 1916-1925.
Dailey, et al. Glucagon-like peptide 1 and appetite. Trends Endocrinol Metab. Feb. 2013;24(2):85-91. doi: 10.1016/j.tem.2012.11.008. Epub Jan. 16, 2013.
Database GNPD [Online] Mintel; Feb. 2015, PharmXcross: "Triple Premium Alive Probiotics", XP002779023, Database accession No. 2898253.
Database WPI, Week 201371, Thomson Scientific, London, GB; AN 2013-R31140, XP002805741, and CN103131647A (Shanghai Shangyao Pharm Ind, Co, Ltd, Jun. 5, 2013.
De Filippo, et al., Impact of Diet in Shaping Gut Microbiota Revealed by a Comparative Study in Children From Europe and Rural Africa, PNAS, Aug. 2010, 107(33):14691-6.
De Leoz, et al., Human Milk Glycomics and Gut Microbial Genomics in Infant Feces Show a Correlation between Human Milk Oligosaccharides and Gut Microbiota: A Proof-of-Concept Study, J. Proteome Res., 2015, 14:491-502.
De Vadder, et al. Microbiota-generated metabolites promote metabolic benefits via gut-brain neural circuits. Cell. Jan. 16, 2014;156(1-2):84-96. doi: 10.1016/j.cell.2013.12.016. Epub Jan. 9, 2014.
Declaration of Interference, Patent Interference No. 106,130, filed Jan. 26, 2021, 9 pages.
Delahanty, et al. Psychological and behavioral correlates of baseline BMI in the diabetes prevention program (DPP). Diabetes Care. Nov. 2002;25(11):1992-8.
Derrien, et al. (2004). *Akkermansia muciniphila* gen. nov., sp. nov., a human intestinal mucin-degrading bacterium. Int. J. Syst. Evol. Microbiol. 54(Pt 5), 1469-1476. doi: 10.1099/ijs.0.02873-0.
Derrien, et al. (2008). The Mucin degrader Akkermansia muciniphila is an abundant resident of the human intestinal tract. Appl. Environ. Microbiol. 74, 1646-1648. doi: 10.1128/AEM.01226-07.
Derrien, et al. (2011). Modulation of mucosal immune response, tolerance, and proliferation in mice colonized by the mucin-degrader Akkermansia muciniphila. Front. Microbiol. 2:166. doi: 10.3389/fmicb.2011.00166.
Derrien, et al., *Akkermansia muciniphila*, gen. nov., sp. nov., a novel intestinal mucin-degrading bacterium, FEMS Congress of European Microbiologists Abstract Book 1 (2003): 237.
Derrien, et al. Mucin-bacterial interactions in the human oral cavity and digestive tract. Gut Microbes. Jul.-Aug. 2010; 1(4): 254-268.
Derrien. Mucin utilisation and host interactions of the novel intestinal microbe Akkermansia muciniphila. 2007.
Desbonnet, et al. Effects of the probiotic Bifidobacterium infantis in the maternal separation model of depression. Neuroscience. Nov. 10, 2010;170(4):1179-1188. doi: 10.1016/j.neuroscience.2010.08.005. Epub Aug. 6, 2010.
Detman, et al. Cell factories converting lactate and acetate to butyrate: Clostridium butyricum and microbial communities from dark fermentation bioreactors. Microb Cell Fact. Feb. 13, 2019;18(1):36. doi: 10.1186/s12934-019-1085-1.
Dewulf, et al. (2011). Inulin-type fructans with prebiotic properties counteract GPR43 overexpression and PPARgamma-related adipogenesis in the white adipose tissue of high-fat diet-fed mice. J. Nutr. Biochem. 22, 712-722. doi: 10.1016/j.jnutbio.2010.05.009.
Diamant, et al. Do nutrient-gut-microbiota interactions play a role in human obesity, insulin resistance and type 2 diabetes? Obesity reviews. 2011; 12:272-281.
Diaz Heijtz, et al. Normal gut microbiota modulates brain development and behavior. Proc Natl Acad Sci U S A. Feb. 15, 2011;108(7):3047-52. doi: 10.1073/pnas.1010529108. Epub Jan. 31, 2011.
Dolfing, et al. Acetate inhibition of methanogenic, syntrophic benzoate degradation. Appl Environ Microbiol. Jul. 1988;54(7):1871-3.
Donohoe, et al. A gnotobiotic mouse model demonstrates that dietary fiber protects against colorectal tumorigenesis in a microbiota- and butyrate-dependent manner. Cancer Discov. Dec. 2014;4(12):1387-97. doi: 10.1158/2159-8290.CD-14-0501. Epub Sep. 29, 2014.
Donohoe, et al. The microbiome and butyrate regulate energy metabolism and autophagy in the mammalian colon. Cell Metab. May 4, 2011;13(5):517-26. doi: 10.1016/j.cmet.2011.02.018.
Dray, et al. Co-inertia analysis and the linking of ecological data tables. Ecology. 2003; 84(11):3078-3089.
Dubourg, et al. (2013). High-level colonisation of the human gut by Verrucomicrobia following broad-spectrum antibiotic treatment. Int. J. Antimicrob. Agents 41, 149-155. doi: 10.1016/j.ijantimicag.2012.10.012.
Duncan, et al. Acetate Utilization and Butyryl Coenzyme A (CoA): Acetate-CoA Transferase in Butyrate-Producing Bacteria from the Human Large Intestine. Appl Environ Microbiol. Oct. 2002;68(10):5186-90.
Duncan et al. "Lactate-utilizing bacteria, isolated from human feces, that produce butyrate as a major fermentation product" Applied and environmental microbiology. 2004, vol. 70, No. 10, pp. 5810-5817.
Eckburg, PB. et al., Diversity of the human intestinal microbial flora, Science. Jun. 10, 2005;308(5728):1635-8. Epub Apr. 14, 2005.
Edgar, R.C. Updating the 97% identity threshold for 16S ribosomal RNA OTUs. Bioinformatics. Jul. 15, 2018;34(14):2371-2375. doi: 10.1093/bioinformatics/bty113.
Eid, et al. Real-time DNA sequencing from single polymerase molecules. Science. Jan. 2, 2009;323(5910):133-8. doi: 10.1126/science.1162986. Epub Nov. 20, 2008.
Endo, et al. Butyrate-producing probiotics reduce nonalcoholic fatty liver disease progression in rats: new insight into the probiotics for the gut-liver axis. PLoS One. May 16, 2013;8(5):e63388. doi: 10.1371/journal.pone.0063388. Print 2013.
Epel, et al. The reward-based eating drive scale: a self-report index of reward-based eating. PLoS One. Jun. 30, 2014;9(6):e101350. doi: 10.1371/journal.pone.0101350. eCollection 2014.
Erickson, et al. Integrated metagenomics/metaproteomics reveals human host-microbiota signatures of Crohn's disease. PLoS One. 2012;7(11):e49138. doi: 10.1371/journal.pone.0049138. Epub Nov. 28, 2012.
European search report and opinion dated Jun. 28, 2021 for EP Application No. 18850315.5.
European search report with written opinion dated Mar. 26, 2018 for EP Application No. 15853671.4.
European search report with written opinion dated Nov. 19, 2018 for EP Application No. 16765880.6.
Everard, et al. (2011). Responses of gut microbiota and glucose and lipid metabolism to prebiotics in genetic obese and diet-induced leptin-resistant mice. Diabetes Metab. Res. Rev. 60, 2775-2786. doi: 10.2337/db11-0227.
Everard, et al. Akkermansia muciniphila link gut barrier function with inflammation and metabolic disorders associated with obesity. Keystone Symposia: The Microbiome (Q8) (Keystone, USA, du Apr. 3, 2012 au Sep. 3, 2012). Accessed Nov. 8, 2021 online at https://dial.uclouvain.be/pr/boreal/object/boreal:138299 (1 page).
Everard, et al. PO9 «Akkermansia muciniphila» : Une nouvelle bactérie jouant un rôle clé dans la fonction barrière de l'intestin, l'inflammation et les désordres métaboliques associés à l'obésité? (English: PO9 "Akkermansia muciniphila": a new bacterium playing a key role in the barrier function of the intestine, inflammation and associated metabolic disorders associated with obesity?) Diabetes & Metabolism. vol. 38. Supplement 2. (2012) p. A24. https://doi.org/10.1016/S1262-3636(12)71071-6. (English Machine Translation).
Everard, et al. (2013). Cross-talk between Akkermansia muciniphila and intestinal epithelium controls diet-induced obesity. Proc. Natl. Acad. Sci. U.S.A. 110, 9066-9071. doi: 10.1073/pnas.1219451110.
Everard, et al. Gut microbiota and GLP-1. Rev Endocr Metab Disord. Sep. 2014;15(3):189-96. doi: 10.1007/s11154-014-9288-6.
Fabricius, et al. Quantitative investigations into the elimination of in vitro-obtained spores of the non-pathogenic Clostridium butyricum strain CNRZ 528, and their persistence in organs of different species

(56) References Cited

OTHER PUBLICATIONS following intravenous spore administration. Res Microbiol. Nov.-Dec. 1993 144(9):741-53. DOI: 10.1016/0923-2508(93)90038-4.
Falony et al. Cross-Feeding between Bifidobacterium longum BB536 and Acetate-Converting, Butyrate-Producing Colon Bacteria during Growth on Oligofructos. Appl. Environ. Microbiol. 72(12):7835-7841 (2006).
Flores, et al. Microbiome of Affected and Unaffected Skin of Patients with Atopic Dermatitis Before and After Emollient Treatment. Journal of Drugs in Dermatology, Nov. 2014, vol. 13, Issue 11, pp. 611-618.
Flores, et al. Skin Microbiome Diversity in Patients with Atopic Dermatitis Before and After Emollient Treatment.
Franks, et al. Variations of bacterial populations in human feces measured by fluorescent in situ hybridization with group-specific 16S rRNA-targeted oligonucleotide probes. Appl Environ Microbiol. Sep. 1998;64(9):3336-45.
Freshney. Culture of Animal Cells: A Manual of Basic Technique and Specialized Applications. 6th Edition. 2010.
Furet, et al., Differential Adaptation of Human Gut Microbiota to Bariatric Surgery-Induced Weight Loss: Links with Metabolic and Low-Grade Inflammation Markers, Diabetes, 2010, 59(12):3049-57.
Ganesh, et al. Enterococcus faecium NCIMB 10415 does not protect interleukin-10 knock-out mice from chronic gut inflammation. Beneficial Microbes 3.1 (Mar. 2012): 43-50.
Gao, et al. Butyrate improves insulin sensitivity and increases energy expenditure in mice. Diabetes. Jul. 2009. 58(7):1509-17. doi: 10.2337/db08-1637. Epub Apr. 14, 2009.
Gearhardt, et al. Preliminary validation of the Yale Food Addiction Scale. Appetite. Apr. 2009;52(2):430-6. doi: 10.1016/j.appet.2008.12.003. Epub Dec. 11, 2008.
Gennaro, A.R. Quality Assurance and Control. Remington: The Science and Practice of Pharmacy. 2000. Lippincott Williams & Wilkins, 20th ed. pp. 980-983.
Gibbs et al. Urocanic Acid in the Skin: A Mixed Blessing? Journal of Investigative Dermatology (2011) 131, 14-17.
Gibson, et al. (1995). Dietary modulation of the human colonic microbiota: introducing the concept of prebiotics. J. Nutr. 125, 1401-1412.
Gibson, et al. "Inulin and Oligofructose: New Scientific Developments", Nutrition Today, Mar. 1, 2008, pp. 54-59, XP055327770.
Gomez-Gallego, et al. Akkermansia muciniphila: a novel functional microbe with probiotic properties. Benef Microbes. Jun. 13, 2016:1-14. doi:10.3920/BM2016.0009.
Gomez-Gallego, et al. Infant formula supplemented with polyamines alters the intestinal microbiota in neonatal BALB/cOlaHsd mice. J Nutr Biochem. Nov. 2012;23(11):1508-13. doi: 10.1016/j.jnutbio.2011.10.003. Epub Mar. 7, 2012.
Grasset, et al. A Specific Gut Microbiota Dysbiosis of Type 2 Diabetic Mice Induces GLP-1 Resistance through an Enteric No-Dependent and Gut-Brain Axis Mechanism. Cell Metab. May 2, 2017;25(5):1075-1090.e5. doi: 10.1016/j.cmet.2017.04.013.
Gregoriadis. Chapter 14: Liposomes. Drug Carriers in Biology and Medicine (57 pgs) (Academic Press, 1979).
Grice, E. The Skin Microbiome: Potential for Novel Diagnostic and Therapeutic Approaches to Cutaneous Disease. Semin Cutan Med Surg, 2014, 33:98-103.
Grzeskowiak, et al, The impact of perinatal probiotic intervention on gut microbiota: Double-blind placebo-controlled trials in Finland and Germany, Anaerobe 18.1 (Feb. 2012): 7-13.
Gupta, et al. Patterns of brain structural connectivity differentiate normal weight from overweight subjects. Neuroimage Clin. Jan. 13, 2015;7:506-17. doi: 10.1016/j.nicl.2015.01.005. eCollection 2015.
Gurry, (2017) "Synbiotic approaches to human health and well-being." Microbial Biotechnology, vol. 10, No. 5, pp. 1070-1073.
Hai Suisan Shigen Oyobi Shokuhin Kako Zansa o Genryo to suru Kokinosei Hakko Shiryo Seizo Gijutsu no Kaihatsu. Heisei 22 Nendo Senryakuteki Kiban Gijutsu Kodoka Shien Jigyo Kenkyu Seika Hokokusho. Kanto Bureau of Economy, Trade and Industry. 2011, pp. 1-26.
Hakansson, et al. Gut microbiota and inflammation. Nutrients. Jun. 2011;3(6):637-82. doi: 10.3390/nu3060637. Epub Jun. 3, 2011.
Hamer, et al. Review article: the role of butyrate on colonic function. Aliment Pharmacol Ther. Jan. 15, 2008;27(2):104-19. Epub Oct. 25, 2007.
Hansen, et al., Early life treatment with vancomycin propagates Akkermansia muciniphila and reduces diabetes incidence in the NOD mouse, Diabetologia (2012), 55:2285-2294.
Harmsen, et al. Extensive Set of 16S rRNA-Based Probes for Detection of Bacteria in Human Feces. Applied and Environmental Microbiology Jun. 2002, 68 (6) 2982-2990; DOI: 10.1128/AEM.68.6.2982-2990.2002.
Hendrickson et al., Remington: The Science and Practice of Pharmacy, 21st Edition; Lippincott Williams & Wilkins: Philadelphia, PA, 2005; pp. 889-938.
Henry Ford Health Clinic, Endocrinology, Diabetes and Bone Mineral Disorders webcite information. 2016. 2 pages. http://www.henryford.com/body_academic.cfm?id=52450.
Hildebrand, et al, A comparative analysis of the intestinal metagenomes present in guinea pigs (Cavia porcellus) and humans (Homo sapiens, BMC Genomics 13 (Sep. 28, 2012).
Hildebrandt, et al., High-Fat Diet Determines the Composition of the Murine Gut Microbiome Independently of Obesity, Gastroenterology, 2009, 137(5):1716-24 el-2.
HiVeg Peptone, Technical Data Sheet, 2019 (Year: 2019).
Hjorth, et al. Pre-treatment microbial Prevotella-to-Bacteroides ratio, determines body fat loss success during a 6-month randomized controlled diet intervention, International Journal of Obesity accepted article preview Sep. 8, 2017; doi: 10.1038/ijo.2017.220.
Hold, et al. Assessment of microbial diversity in human colonic samples by 16S rDNA sequence analysis. FEMS Microbiol Ecol. Jan. 1, 2002. 39(1):33-9. doi: 10.1111/j.1574-6941.2002.tb00904.x.
Hold et al. 'Oligonucleotide probes that detect quantitatively significant groups of butyrate-producing bacteria in human feces.' Applied and environmental microbiology. 2003, vol. 69, No. 7, pp. 4320-4324.
Hosseini et al. Propionate as a Health-Promoting Microbial Metabolite in the Human Gut. Nutrition Reviews 69:245-258 (2010).
Hu, et al. Type 1 Diabetes and Gut Microbiota: Friend or Foe? Pharmacological Research 98 (2015): 9-15.
International search report and written opinion dated Jan. 27, 2016 for PCT Application No. US2015/058511.
International search report and written opinion dated Jun. 17, 2016 for PCT/US2016/023311.
International search report with written opinion dated Nov. 23, 2018 for PCT/US18/48955.
Ismail, et al. Frequency of Firmicutes and Bacteroidetes in gut microbiota in obese and normal weight Egyptian children and adults. Arch Med Sci. Jun. 2011;7(3):501-7. doi: 10.5114/aoms.2011.23418. Epub Jul. 11, 2011.
Isolauri, et al. Probiotics in the management of atopic eczema. Clin Exp Allergy. Nov. 2000;30(11):1604-10.
Jeurink, et al. (2013). Human milk: a source of more life than we imagine. Benef. Microbes 4, 17-30. doi: 10.3920/BM2012. 0040.
Johnson, et al. Is primary prevention of Clostridium difficile infection possible with specific probiotics? Int J Infect Dis. Nov. 2012;16(11):e786-92. doi: 10.1016/j.ijid.2012.06.005. Epub Aug. 3, 2012.
Kadooka, et al. Regulation of abdominal adiposity by probiotics (Lactobacillus gasseri SBT2055) in adults with obese tendencies in a randomized controlled trial. Eur J Clin Nutr. Jun. 2010;64(6):636-43. doi: 10.1038/ejcn.2010.19. Epub Mar. 10, 2010.
Kalliomaki, et al. Probiotics in primary prevention of atopic disease: a randomised placebo-controlled trial. Lancet. Apr. 7, 2001;357(9262):1076-9.
Kallus, et al., the Intestinal Microbiota and Obesity, J. Clin. Gastroenterol, Jan. 2012, 46(1):16-24.
Kamneva, et al, Analysis of Genome Content Evolution in PVC Bacterial Super-Phylum: Assessment of Candidate Genes Associ-

(56) References Cited

OTHER PUBLICATIONS ated with Cellular Organization and Lifestyle, Genome Biology and Evolution 4.12 (2012): 1375-1390.

Karlsson, et al. Gut metagenome in European women with normal, impaired and diabetic glucose control. Nature. Jun. 6, 2013;498(7452):99-103. doi: 10.1038/nature12198. Epub May 29, 2013.

Karlsson, et al, The Microbiota of the Gut in Preschool Children With Normal and Excessive Body Weight, Obesity 20.11 (Nov. 2012): 2257-2261.

Khan, et al. Antioxidants keep the potentially probiotic but highly oxygen-sensitive human gut bacterium Faecalibacterium prausnitzii alive at ambient air. PLoS One. May 5, 2014;9(5):e96097. doi: 10.1371/journal.pone.0096097. eCollection 2014.

Khan, et al., Pathophysiology and Treatment of Type 2 Diabetes: Perspectives on the Past, Present and Future, Lancet, Mar. 22, 2014, 383(9922):1068-1083.

Kilpatrick, et al. Influence of sucrose ingestion on brainstem and hypothalamic intrinsic oscillations in lean and obese women. Gastroenterology. May 2014;146(5):1212-21. doi: 10.1053/j.gastro.2014.01.023. Epub Jan. 28, 2014.

Kim, et al. Effects of Probiotics for the Treatment of Atopic Dermatitis: A Meta-Analysis of Randomized Controlled Trials. Ann. Allergy Asthma Immunol 113 (2014): 217-226.

Kinumaki, et al. Longitudinal analysis of gut flora in Kawasaki disease patients using next-generation DNA sequencing. Pediatrics International, suppl. 1 54 (Feb. 2012): 81.

Knip, et al. The role of the intestinal microbiota in type 1 diabetes mellitus. Nat Rev Endocrinol. Mar. 2016;12(3):154-67. doi: 10.1038/nrendo.2015.218. Epub Jan. 4, 2016.

Kober, et al. The effect of probiotics on immune regulation, acne, and photoaging. Int J Womens Dermatol. Apr. 6, 2015;1(2):85-89. doi: 10.1016/j.ijwd.2015.02.001. eCollection Jun. 2015.

Komaroff. How the Microbiome Might Promote Metabolic Syndrome and Obesity. Anthony L. Komaroff, MD reviewing Perry RJ et al. Nature Jun. 9, 2016. Trajkovski M and Wollheim CB. Nature Jun. 9, 2016. Published Jul. 14, 2016.

Kong et al. Temporal shifts in the skin microbiome associated with disease flares and treatment in children with atopic dermatitis. Genome Res 22(5):850-859 (2012).

Kootte, et al., the Therapeutic Potential of Manipulating Gut Microbiota in Obesity and Type 2 Diabetes Mellitus, Diabetes, Obesity and Metabolism, Epub 2011, 14:112-120.

Kuhn, et al. Applied predictive modeling. Springer, 2013. 595 pages.

Lamont. Infection in the prediction and antibiotics in the prevention of spontaneous preterm labour and preterm birth. BJOG: an International Journal of Obstetrics and Gynaecology. 2003; 110(Suppl 20):71-75.

Lange, Vinzenz et al. Selected reaction monitoring for quantitative proteomics: a tutorial. Molecular Systems Biology 4(222):1-14 (Oct. 14, 2008).

Larsen, et al. Gut Microbiota in Human Adults with Type 2 Diabetes Differs from Non-Diabetic Adults. PLoS One. Feb. 5, 2010;5(2):e9085. doi: 10.1371/journal.pone.0009085.

Le Barz, et al. Probiotics as Complementary Treatment for Metabolic Disorders. Diabetes Metab J. Aug. 2015; 39(4): 291-303. doi:10.4093/dmj.2015.39.4.291.

Lebourhis et al. Development and Validation of PCR Primers to Assess the Diversity of Clostridium spp. in Cheese by Temporal Temperature Gradient Gel Electrophoresis. Applied and Environmental Microbiology, Jan. 2005, p. 29-38 vol. 71.

Lefebvre, et al., Role of Bile Acids and Bile Acid Receptors in Metabolic Regulation, Physiol Rev, 2009, 89(1):147-91.

Leung. New Insights into Atopic Dermatitis: Role of Skin Barrier and Immune Dysregulation. Allergol Int. Jun. 2013;62(2):151-61. doi: 10.2332/allergolint.13-RAI-0564.

Levinson et al., Acute Gastrointestinal Graft-vs-Host Disease Is Associated With Increased Enteric Bacterial Bloodstream Infection Density in Pediatric Allogeneic Hematopoietic Cell Transplant Recipients, Clinical Infectious Diseases, May 5, 2015,61(3):350-357.

Levkovich, et al. Probiotic Bacteria Induce a 'Glow of Health'. PLoS One. 2013;8(1):e53867. doi: 10.1371/journal.pone.0053867. Epub Jan. 16, 2013.

Ley, et al., Microbial Ecology: Human Gut Microbes Associated With Obesity, Nature, Dec. 21, 2006, 444:1022-3.

Li, et al. Akkermansia Muciniphila Protects Against Atherosclerosis by Preventing Metabolic Endotoxemia-Induced Inflammation in Apoe-/- Mice. Circulation. Jun. 14, 2016;133(24):2434-46. doi: 10.1161/CIRCULATIONAHA.115.019645. Epub Apr. 25, 2016.

Li et al., Metabolic Surgery Profoundly Influences Gut Microbial-Host Metabolic Cross-Talk, Gut, 2011; 60(9):1214-23.

Liou, et al. Conserved shifts in the gut microbiota due to gastric bypass reduce host weight and adiposity. Sci Transl Med. Mar. 27, 2013;5(178):178ra41. doi: 10.1126/scitranslmed.3005687.

Liu, et al. Butyrate protects rat liver against total hepatic ischemia reperfusion injury with bowel congestion. PLoS One. Aug. 29, 2014;9(8):e106184. doi: 10.1371/journal.pone.0106184. eCollection 2014.

Liu, et al. Neuroprotective Effects of Clostridium butyricum against Vascular Dementia in Mice via Metabolic Butyrate. Biomed Res Int. 2015;2015:412946. doi: 10.1155/2015/412946. Epub Oct. 7, 2015.

Lopez-Siles et al., Cultured Representatives of Two Major Phylogroups of Human Colonic Faecalibacterium prausnitzii Can Utilize Pectin, Uronic Acids, and Host-Derived Substrates for Growth, Applied and Environmental Microbiology, 420-428.

Louis et al. Diversity, metabolism and microbial ecology of butyrate-producing bacteria from the human large intestine. FEMS Microbiol Lett. 2009, vol. 294(1), p. 1-8.

Lukovac, et al. Differential Modulation by Akkermansia muciniphila and Faecalibacterium prausnitzii of Host Peripheral Lipid Metabolism and Histone Acetylation in Mouse Gut Organoids. mBio. Jul.-Aug. 2014; 5(4): e01438-14. Published online Aug. 12, 2014. doi: 10.1128/mBio.01438-14.

Lyra, et al. Comparison of bacterial quantities in left and right colon biopsies and faeces. World J Gastroenterol. Aug. 28, 2012; 18(32): 4404-4411.

Lyra, et al. Quantities of Commensal and Pathogenic Bacteria in Mucosal Biopsies of the Left and Right Colon and Feces. Gastroenterology 142.5, Suppl. 1 (May 2012): S542.

Macfarland, et al. Pharmaceutical probiotics for the treatment of anaerobic and other infections. Anaerobe. Apr.-Jun. 1997;3(2-3):73-8.

Maldonado-Gomez, et al. Stable Engraftment of Bifidobacterium longum AH1206 in the Human Gut Depends on Individualized Features of the Resident Microbiome. Cell Host Microbe. Sep. 28, 2016. pii: S1931-3128(16)30378-X. doi: 10.1016/j.chom.2016.09.001.

Man et al. The Internal Transcribed Spacer Region, a New Tool for Use in Species Differentiation and Delineation of Systematic Relationships within the Campylobacter Genus. Applied and Environmental Microbiology, May 2010, vol. 76, No. 10, p. 3071-3081. (Year: 2010).

Maslowski, et al. Regulation of inflammatory responses by gut microbiota and chemoattractant receptor GPR43. Nature. Oct. 29, 2009;461(7268):1282-6. doi: 10.1038/nature08530.

Maurer, et al. (2010). Consumption of diets high in prebiotic fiber or protein during growth influences the response to a high fat and sucrose diet in adulthood in rats. Nutr.Metab. (Lond) 7:77. doi: 10.1186/1743-7075-7-77.

Mayer, et al. Gut microbes and the brain: paradigm shift in neuroscience. J Neurosci. Nov. 12, 2014;34(46):15490-6. doi: 10.1523/JNEUROSCI.3299-14.2014.

Mayer, et al. Gut/brain axis and the microbiota. J Clin Invest. Mar. 2, 2015;125(3):926-38. doi: 10.1172/JCI76304. Epub Feb. 17, 2015.

McLean et al. Characterisation and selection of a Lactobacillus species to re-colonise the vagina of women with recurrent bacterial vaginosis. J. Med. Microbiol., 2000, vol. 49, pp. 543-552.

McPherson, M. J. et al (Eds.) PCR 2: A Practical Approach. Practical approach series. IRL Press. 1995. (Table of Contents).

(56) References Cited

OTHER PUBLICATIONS

Mekkes, et al. The development of probiotic treatment in obesity: a review. Beneficial MICR, Wageningen Academic Publishes, NL, vol. 5, No. 1, Mar. 1, 2014, pp. 19-28.
Meneghin, et al. Probiotics and atopic dermatitis in children. Pharmaceuticals (Basel). Jul. 6, 2012;5(7):727-44. doi: 10.3390/ph5070727.
Messaoudi, et al. Assessment of psychotropic-like properties of a probiotic formulation (Lactobacillus helveticus R0052 and Bifidobacterium longum R0175) in rats and human subjects. Br J Nutr. Mar. 2011;105(5):755-64. doi: 10.1017/S0007114510004319. Epub Oct. 26, 2010.
Millon, et al. Comparative meta-analysis of the effect of *Lactobacillus* species on weight gain in humans and animals. Microb Pathog. Aug. 2012;53(2):100-8. doi: 10.1016/j.micpath.2012.05.007. Epub May 24, 2012.
Molloy et al. The Potential Link between Gut Microbiota and IgE-Mediated Food Allergy in Early Life. Int. J. Environ. Res. Public Health 2013, 10, 7235-7256.
Muller, et al., The dynamics of genome replication using deep sequencing, Nucleic Acids Research, 2014, 42(1), e3, 11 pages. Epub Oct. 1, 2013.
Munoz-Tamayo, et al. Kinetic modelling of lactate utilization and butyrate production by key human colonic bacterial species. FEMS Microbiol. Ecol., 76 (2011), 615-624 DOI:10.1111/j.1574-6941. 2011.01085.x.
Murphy, et al. Gut hormones and the regulation of energy homeostasis. Nature. Dec. 14, 2006;444(7121):854-9.
Naito, et al., Beneficial Effect of Oral Administration of Lactobacillus Casei Strain Shirota on Insulin Resistance in Diet-Induced Obesity Mice, J. appl. microbial., Mar. 2011, 110(3):650-7.
Narang, et al. Improved phosphotriester method for the synthesis of gene fragments. Methods Enzymol. 1979;68:90-8.
Naruszewicz, et al. Effect of Lactobacillus plantarum 299v on cardiovascular disease risk factors in smokers. Am J Clin Nutr. Dec. 2002;76(6):1249-55.
Navarro-Noya, et al., Bacterial Communities Associated With the Rhizosphere of Pioneer Plants (*Bahia xylopoda* and *Viguiera linearis*) Growing on Heavy Metals-Contaminated Soils, Antonievan Leeuwenhoek, 2010, 97:335-49.
Netherlands Trial Register (NTR): "Dosefinding trial studying effect of 4 weeks Intervention on safety and efficacy in males with Metabolic syndrome with oral Eubacterium hallii" dated Nov. 22, 2014, https://www.trialregister.nl/trial/4775. Retrieved online Nov. 9, 2020. (2 pages).
Nilsson, et al. A Cereal-Based Evening Meal Rich in Indigestible Carbohydrates Increases Plasma Butyrate the Next Morning. J Nutr. Nov. 2010;140(11):1932-6. doi: 10.3945/jn.110.123604. Epub Sep. 1, 2010.
Notice of Allowance dated Jan. 13, 2020 for U.S. Appl. No. 15/271,672.
Notice of Allowance dated Feb. 19, 2020 for U.S. Appl. No. 15/271,672.
Notice of Allowance dated Feb. 21, 2020 for U.S. Appl. No. 16/159,536.
Notice of Allowance dated Jul. 17, 2020 for U.S. Appl. No. 16/159,532.
Notice of Allowance dated Jul. 23, 2020 for U.S. Appl. No. 16/159,537.
Notice of Allowance dated Sep. 2, 2016 for U.S. Appl. No. 15/139,097.
Notice of Allowance dated Oct. 13, 2021 for U.S. Appl. No. 16/830,995.
Notice of Allowance dated Nov. 17, 2021 for U.S. Appl. No. 16/830,995.
Notice of Allowance dated Nov. 24, 2021 for U.S. Appl. No. 16/830,972.
Nohr, et al. GPR41/FFAR3 and GPR43/FFAR2 as cosensors for short-chain fatty acids in enteroendocrine cells vs FFAR3 in enteric neurons and FFAR2 in enteric leukocytes. Endocrinology. Oct. 2013;154(10):3552-64. doi: 10.1210/en.2013-1142. Epub Jul. 24, 2013.
Nylund, et al. Severity of atopic disease inversely correlates with intestinal microbiota diversity and butyrate-producing bacteria. Allergy. Feb. 2015;70(2):241-4. doi: 10.1111/all.12549.
Office action dated Jan. 11, 2019 for U.S. Appl. No. 15/286,218.
Office action dated Feb. 7, 2017 for U.S. Appl. No. 15/286,218.
Office action dated Feb. 21, 2020 for U.S. Appl. No. 15/286,218.
Office action dated Mar. 4, 2021 for U.S. Appl. No. 16/830,972.
Office action dated Mar. 5, 2020 for U.S. Appl. No. 16/159,524.
Office action dated Apr. 4, 2019 for U.S. Appl. No. 16/159,524.
Office action dated Apr. 16, 2020 for U.S. Appl. No. 16/159,532.
Office action dated Apr. 29, 2020 for U.S. Appl. No. 16/159,537.
Office action dated May 10, 2019 for U.S. Appl. No. 15/271,672.
Office action dated May 10, 2019 for U.S. Appl. No. 16/159,532.
Office action dated May 27, 2021 for U.S. Appl. No. 16/830,995.
Office action dated May 31, 2019 for U.S. Appl. No. 16/159,536.
Office action dated Jun. 5, 2019 for U.S. Appl. No. 16/159,537.
Office action dated Jun. 11, 2018 for U.S. Appl. No. 15/074,923.
Office action dated Jun. 16, 2017 for U.S. Appl. No. 15/286,218.
Office action dated Aug. 28, 2018 for U.S. Appl. No. 15/271,672.
Office action dated Sep. 18, 2019 for U.S. Appl. No. 16/159,524.
Office action dated Sep. 30, 2021 for U.S. Appl. No. 16/830,972.
Office action dated Oct. 16, 2019 for U.S. Appl. No. 15/286,218.
Office action dated Oct. 30, 2019 for U.S. Appl. No. 16/159,532.
Office action dated Oct. 31, 2019 for U.S. Appl. No. 15/271,672.
Office action dated Oct. 31, 2019 for U.S. Appl. No. 16/159,536.
Office action dated Oct. 31, 2019 for U.S. Appl. No. 16/159,537.
Office action dated Nov. 13, 2020 for U.S. Appl. No. 16/830,972.
Office action dated Nov. 13, 2020 for U.S. Appl. No. 16/830,995.
Office action dated Nov. 27, 2017 for U.S. Appl. No. 15/286,218.
Office action dated Dec. 13, 2018 for U.S. Appl. No. 16/159,536.
Office action dated Dec. 13, 2018 for U.S. Appl. No. 16/159,537.
Office action dated Dec. 20, 2017 for U.S. Appl. No. 15/074,923.
Oh, et al. Shifts in Human Skin and Nares Microbiota of Healthy Children and Adults. Genome Medicine 2012, 4:77.
O'Keefe, et al. Fat, fibre and cancer risk in African Americans and rural Africans. Nat Commun. Apr. 28, 2015;6:6342. doi: 10.1038/ncomms7342.
Ong, et al. Endogenous antimicrobial peptides and skin infections in atopic dermatitis. N Engl J Med. Oct. 10, 2002;347(15):1151-60.
Ouwehand, et al. (2005). Prebiotics and other microbial substrates for gut functionality. Curr. Opin. Biotechnol. 16, 212-217. doi: 10.1016/j.copbio.2005. 01.007.
Ouwerkerk, et al. *Akkermansia glycaniphila* sp. nov., an anaerobic mucin-degrading bacterium isolated from reticulated python faeces. Int J Syst Evol Microbiol. Nov. 2016;66(11):4614-4620. doi: 10.1099/ijsem.0.001399. Epub Aug. 5, 2016.
Ouwerkerk, et al. *Akkermansia glycaniphila* sp. nov., an anaerobic mucin-degrading bacterium isolated from reticulated python faeces. Int J Syst Evol Microbiol. Nov. 2016;66(11):4614-4620. doi: 10.1099/ijsem.0.001399. Epub Aug. 5, 2016. (Manuscript Draft—21 pages).
Pachikian, et al. (2012). Prebiotic approach alleviates hepatic steatosis: implication of fatty acid oxidative and cholesterol synthesis pathways. Mol. Nutr. Food Res. 57, 347-359. doi: 10.1002/mnfr. 201200364.
Panther, et al. The Importance of Acidification in Atopic Eczema: An Underexplored Avenue for Treatment. J Clin Med. May 18, 2015;4(5):970-8. doi: 10.3390/jcm4050970.
Parnell, et al. Weight loss during oligofructose supplementation is associated with decreased ghrelin and increased peptide YY in overweight and obese adults. Am J Clin Nutr. Jun. 2009;89(6):1751-9. doi: 10.3945/ajcn.2009.27465. Epub Apr. 22, 2009.
Patti, et al., Serum Bile Acids Are Higher in Humans with Prior Gastric Bypass: Potential Contribution to Improved Glucose and Lipid Metabolism, Obesity (silver spring), 2009, 17(9):1671-7.
Peng, et al. Butyrate enhances the intestinal barrier by facilitating tight junction assembly via activation of AMP-activated protein kinase in Caco-2 cell monolayers. J Nutr. Sep. 2009;139(9):1619-1625. doi: 10.3945/jn.109.104638. Epub Jul. 22, 2009.

(56) References Cited

OTHER PUBLICATIONS

Perez, et al. Surface Properties of Bifidobacterial Strains of Human Origin. Applied and Environmental Microbiology. vol. 64. No. 1. pp. 21-26. Jan. 1998.
Perry, et al. Acetate mediates a microbiome-brain-β-cell axis to promote metabolic syndrome. Nature. Jun. 8, 2016;534(7606):213-7. doi: 10.1038/nature18309.
Petrof et al. Stool substitute transplant therapy for the eradication of Clostridium difficile infection: "RePOOPulating" the gut. Microbiome 1(1):3 (2013).
Plovier, et al. A purified membrane protein from Akkermansia muciniphila or the pasteurized bacterium improves metabolism in obese and diabetic mice. Nature Medicine, Jan. 2017, 23(1):107-16.
Png, et al. (2010). Mucolytic bacteria with increased prevalence in IBD mucosa augment in vitro utilization of mucin by other bacteria. Am. J. Gastroenterol. 105, 2420-2428. doi: 10.1038/ajg.2010.281.
Poul, et al. Functional characterization of human receptors for short chain fatty acids and their role in polymorphonuclear cell activation. J Biol Chem. Jul. 11, 2003;278(28):25481-9. Epub Apr. 23, 2003.
Psichas, et al. The short chain fatty acid propionate stimulates GLP-1 and PYY secretion via free fatty acid receptor 2 in rodents. Int J Obes (Lond). Mar. 2015;39(3):424-9. doi: 10.1038/ijo.2014.153. Epub Aug. 11, 2014.
Puddu et al. Evidence for the Gut Microbiota Short-Chain Fatty Acids as Key Pathophysiological Molecules Improving Diabetes. Mediators Inflamm. vol. 2014;2014:162021. Epub Aug. 17, 2014.
Queipo-Ortuno, et al. Gut microbiota composition in male rat models under different nutritional status and physical activity and its association with serum leptin and ghrelin levels. PLoS One. May 28, 2013;8(5):e65465. doi: 10.1371/journal.pone.0065465. Print 2013.
Rajilic-Stojanovic, et al. Development and application of the human intestinal tract chip, a phylogenetic microarray: analysis of universally conserved phylotypes in the abundant microbiota of young and elderly adults. Environ Microbiol. Jul. 2009. 11(7):1736-51. doi: 10.1111/j.1462-2920.2009.01900.x. Epub Mar. 11, 2009.
Rajilic-Stojanovic, et al. Diversity of the human gastrointestinal tract microbiota revisited. Environ Microbiol. Sep. 2007;9(9):2125-36. doi: 10.1111/j.1462-2920.2007.01369.x.
Rao, et al. A randomized, double-blind, placebo-controlled pilot study of a probiotic in emotional symptoms of chronic fatigue syndrome. Gut Pathog. Mar. 19, 2009;1(1):6. doi: 10.1186/1757-4749-1-6.
Rautava, et al., New therapeutic strategy for combating the increasing burden of allergic disease: Probiotics—A Nutrition, Allergy, Mucosal Immunology and Intestinal Microbiota (NAMI) Research Group report, J Allergy Clin Immunol, 16(1) 31-37.
Ravussin, et al. Responses of gut microbiota to diet composition and weight loss in lean and obese mice. Obesity (Silver Spring). Apr. 2012;20(4):738-47. doi: 10.1038/oby.2011.111. Epub May 19, 2011.
Ravussin. Molecular and Physiological Adaptations to Weight Perturbation in Mice. Columbia University, 2012. ProQuest Dissertations Publishing, (2012). 3475216.
Redeclaration, Patent Interference No. 106,130, filed Feb. 24, 2021, 3 pages.
Registad, et al. Gut microbes promote colonic serotonin production through an effect of short-chain fatty acids on enterochromaffin cells. Faseb J. Apr. 2015;29(4):1395-403. doi: 10.1096/fj.14-259598. Epub Dec. 30, 2014.
Remington: The Science and Practice of Pharmacy, Nineteenth Ed (Easton, Pa.: Mack Publishing Company, 1995.
RIDACOM. "Plant Based Media." RIDACOM—Comprehensive Bioscience Supplier—Plant Based Media, 2019, ridacom.com/en/product-list/353/Plant-based-media.
Rippke, et al. Stratum Corneum pH in Atopic Dermatitis: Impact on Skin Barrier Function and Colonization with *Staphylococcus aureus*. Am J Clin Dermatol. 2004;5(4):217-23.
Roberfroid, et al. (2010). Prebiotic effects: metabolic and health benefits. Br. J. Nutr. 104, S1-S63. doi: 10.1017/S0007114510003363.
Roelofsen, et al. The interaction of short-chain fatty acids with adipose tissue: relevance for prevention of type 2 diabetes. Benef Microbes. Nov. 2010;1(4):433-7. doi: 10.3920/BM2010.0028.
Rogers, et al., From gut dysbiosis to altered brain function and mental illness: mechanisms and pathways, Molecular Psychiatry (2016), 21, 738-48.
Rosenfeldt et al. Effect of probiotic Lactobacillus strains in children with atopic dermatitis. J Allergy Clin Immunol 111(2):389-395 (2003).
Roshchina, V. Evolutionary Considerations of Neurotransmitters in Microbial, Plant, and Animal Cells. In: Lyte M, Fitzgerald P (eds). Microbial Endocrinology: Interkingdom Signaling in Infectious Disease and Health. New York: Springer, Feb. 2010, pp. 17-52.
Rossi-Tamisier, et al. Cautionary tale of using 16S rRNA gene sequence similarity values in identification of human-associated bacterial species. Int J Syst Evol Microbiol. Jun. 2015;65(Pt 6):1929-34. doi: 10.1099/ijs.0.000161. Epub Mar. 3, 2015.
Roudsari, et al. Health Effects of Probiotics on the Skin. Crit Rev Food Sci Nutr. 2015;55(9):1219-40. doi: 10.1080/10408398.2012.680078.
Roy, et al., Gut Microbiota Transplantation Demonstrates Its Causal Role in the Development of Type 2 Diabetes and Fatty Liver, Oral Presentations, Journal of Hepatology, 2012, vol. 56, S23.
Rubino, et al., Metabolic Surgery to Treat Type 2 Diabetes: Clinical Outcomes and Mechanisms of Action, Annu. rev. med., 2010, 61:393-411.
Sáez-Lara, et al., Effects of Probiotics and Synbiotics on Obesity, Insulin Resistance Syndrome, Type 2 diabetes and Non-alcoholic Fatty Liver Disease: a Review of Human Clinical Trials, Int. J. Mol. Sci. 2016, 17, 928; doi:10.3390/ijms17060928.
Sahoo, et al a. Boolean implication networks derived from large scale, whole genome microarray datasets. Genome Biol. Oct. 30, 2008;9(10):R157. doi: 10.1186/GB-2008-9-10-r157.
Saleem, et al. Screening of Various Plant Based Extracts for Their Suitability to Be Used as Growth Promoting Substances in the Preparation of Culture Media for Fungi. 114th General Meeting of the American Society for Microbiology. Conference abstracts. 2014.
Sambrook, et al. Molecular Cloning: A Laboratory Manual. 4th Edition, 2012.
Samuel, et al., a Humanized Gnotobiotic Mouse Model of Host-Archaeal-Bacterial Mutualism, PNAS, Jun. 27, 2006, 103(26):10011-16.
Sanmiguel, et al. Interactions between Host Factors and the Skin Microbiome. Cell. Mol. Life Sci., Dec. 2014.
Santacruz, et al. Gut microbiota composition is associated with body weight, weight gain and biochemical parameters in pregnant women. Br J Nutr. Jul. 2010;104(1):83-92. doi: 10.1017/S0007114510000176. Epub Mar. 8, 2010.
Sanz, et al. Gut microbiota and weight gain in overweight and normal weight pregnant women. Journal of Pediatric Gastroenterology and Nutrition, suppl. 3 48 (May 2009): E74.
Sanz, et al. Insights into the roles of gut microbes in obesity. Interdisciplinary perspectives on infectious diseases. vol. 2008 (2008): 829101. doi:10.1155/2008/829101.
Scheuermayer, et al. *Rubritalea marina* gen. nov., sp nov., a marine representative of the phylum 'Verrucomicrobia', isolated from a sponge (*Porifera*). Int J Syst Evol Microbiol. Sep. 2006;56(Pt 9):2119-24.
Schink, B. Energetics of syntrophic cooperation in methanogenic degradation. Microbiol Mol Biol Rev. Jun. 1997;61(2):262-80.
Second Redeclaration, Patent Interference No. 106, 130, filed Apr. 12, 2021, 4 pages.
Segain, et al. Butyrate inhibits inflammatory responses through NFkappaB inhibition: implications for Crohn's disease. Gut. Sep. 2000;47(3):397-403.
Seki, et al. Prevention of antibiotic-associated diarrhea in children by Clostridium butyricum Miyairi. Pediatr Int. Feb. 2003;45(1):86-90.
Senevirathne. Effect of Resistant Starch on Microbial Content of the Intestinal Tract. LSU Doctoral Dissertations. 2717. digitalcommons.lsu.edu/gradschool_dissertations/2717.
Sharma, et al. Glucagon-like peptide-1 (GLP-1) receptor agonist prevents development of tolerance to anti-anxiety effect of ethanol

(56) References Cited

OTHER PUBLICATIONS and withdrawal-induced anxiety in rats. Metab Brain Dis. Jun. 2015;30(3):719-30. doi: 10.1007/s11011-014-9627-z. Epub Nov. 8, 2014.
Simakachorn et al., Tolerance, Safety, and Effect on the Faecal Microbiota of an Enteral Formula Supplemented With Pre- and Probiotics in Critically Ill Children, J. of Ped. Gastroenterology and Nutrition, Aug. 2011, 53(2):174-181.
Sinha, et al. Mutant WT1 is associated with DNA hypermethylation of PRC2 targets in AML and responds to EZH2 inhibition. Blood. Jan. 8, 2015;125(2):316-26. doi: 10.1182/blood-2014-03-566018. Epub Nov. 14, 2014.
Sokol, et al. Faecalibacterium prausnitzii is an anti-inflammatory commensal bacterium identified by gut microbiota analysis of Crohn disease patients. Proc Natl Acad Sci U S A. Oct. 28, 2008;105(43):16731-6. doi: 10.1073/pnas.0804812105. Epub Oct. 20, 2008.
Sonoyama, et al, Comparison of gut microbiota and allergic reactions in BALB/c mice fed different cultivars of rice, British Journal of Nutrition 103.2 (Jan. 28, 2010): 218-226.
Sonoyama, et al, Response of Gut Microbiota to Fasting and Hibernation in Syrian Hamsters, Applied and Environmental Microbiology 75.20 (Oct. 15, 2009): 6451-6456.
Speakman, et al., Revised Equations for Calculating C02 Production From Doubly Labeled Water in Humans, Am J. physiol., Jun. 1993, pp. e912-e917.
Stevenson, et al., New strategies for cultivation and detection of previously uncultured microbes. Appl Environ Microbiol. Aug. 2004;70(8):4748-55.
Stilling, et al. The neuropharmacology of butyrate: The bread and butter of the microbiota-gut-brain axis? Neurochem Int. Oct. 2016;99:110-132. doi: 10.1016/j.neuint.2016.06.011. Epub Jun. 23, 2016.
Stylopoulos, et al., Roux-En-Y Gastric Bypass Enhances Energy Expenditure and Extends Lifespan in Diet-Induced Obese Rats, Obesity, Oct. 17, 2009,(10):1839-47.
Swann, et al., Systemic Gut Microbial Modulation of Bile Acid Metabolism in Host Tissue Compartments, PNAC, Mar. 15, 2011, 108(11):4523-30.
Swidsinki, et al. Acute appendicitis is characterised by local invasion with Fusobacterium nucleatum/necrophorum. Gut. Jan. 2011;60(1):34-40. doi: 10.1136/gut.2009.191320. Epub Nov. 18, 2009.
Takahashi, et al. Reduced Abundance of Butyrate-Producing Bacteria Species in the Fecal Microbial Community in Crohn's Disease. Digestion. 2016;93(1):59-65. doi: 10.1159/000441768. Epub Jan. 14, 2016.
Takaishi, et al. Imbalance in intestinal microflora constitution could be involved in the pathogenesis of inflammatory bowel disease. Int J Med Microbiol. Jul. 2008;298(5-6):463-72. Epub Sep. 25, 2007.
Tang, et al., Endothelial TLR4 and the microbiome drive cerebral cavernous malformations cerebral cavernous malformations, Nature, May 18, 2017, 545:305-10.
Te Biesebeke, et al. Microbial Functionality in the Human Gastrointestinal Tract. Microbes and Environments 19.4:276. Japan Science and Technology Agency. (2004).
Texas Diabetes and Endocrinology Center, website information. 2016. 4 pages. http://www.texasdiabetes.com/.
Thaler, at al., Minireview: Hormonal And Metabolic Mechanisms of Diabetes Remission After Gastrointestinal Surgery, Endocrinology, 2009, 150(6):2518-25.
The Benefits of Butyrate: More than just your average short chain fatty acid. Mar. 9, 2015. 6 pages. http://fionamilne.tumblr.com/post/113178890752/the-benefits-of-butyrate-more-than-just-your.
Thioulouse. Simultaneous analysis of a sequence of paired ecological tables: A comparison of several methods. The Annals of Applied Statistics. 2011; 2300-2325.
Third Party Submission received for EP Application No. 13754666. 9, mailed on Aug. 26, 2021, 11 pages.

Thomas, et al., Tgr5-Mediated Bile Acid Sensing Controls Glucose Homeostasis, Cell Metab, 2009, 10(3):167-77.
Thompson-Chagoyan, et al., Faecal Microbiota and Short-Chain Fatty Acid Levels in Faeces from Infants with Cow's Milk Protein Allergy, Int Arch Allergy Immunol 2011, 156:325-32. Epub Jun. 29, 2011.
Tolhurst, et al. Short-chain fatty acids stimulate glucagon-like peptide-1 secretion via the G-protein-coupled receptor FFAR2. Diabetes. Feb. 2012;61(2):364-71. doi: 10.2337/db11-1019. Epub Dec. 21, 2011.
Tollefson, et al. Atopic Dermatitis: Skin-Directed Management. Pediatrics vol. 134, No. 6, Dec. 2014, pp. e1735-e1744.
Trajkovski, et al. Physiology: Microbial signals to the brain control weight. Nature. Jun. 8, 2016;534(7606):185-7. doi: 10.1038/534185a.
Tremaroli, et al. Functional interactions between the gut microbiota and host metabolism. Nature. Sep. 13, 2012;489(7415):242-249. doi: 10.1038/nature11552.
Turnbaugh, et al., a Core Gut Microbiome in Obese and Lean Twins, Nature, 2009, 457(7228):480-4.
Turnbaugh, et al., an Obesity-Associated Gut Microbiome with Increased Capacity for Energy Harvest, Nature, Dec. 2006, 444:1027-31.
Turnbaugh, et al., The Effect of Diet on The Human Gut Microbiome: A Metagenomic Analysisin Humanized Gnotobiotic Mice, Sci. Transl. Med, 2009, 1(6):6ra14.
Tvede, et al. Bacteriotherapy for chronic relapsing Clostridium difficile diarrhoea in six patients. Lancet. May 27, 1989;1(8648):1156-60.
UCLA Neurobiology of Stress and Resilience Multisite Imaging, website information. 2016. 2 pages. http://uclacns.org/cores/data-core/multisite-neuroimaging/.
Udayappan, et al. Oral treatment with Eubacterium hallii improves insulin sensitivity in db/db mice. NPJ Biofilms Microbiomes. Jul. 6, 2016;2:16009. doi: 10.1038/npjbiofilms.2016.9. eCollection 2016.
Underwood et al., (2014) "Intestinal dysbiosis: Novel mechanisms by which gut microbes trigger and prevent disease." Preventive Medicine, vol. 65, pp. 133-137.
Val-Laillet, et al. Neuroimaging and neuromodulation approaches to study eating behavior and prevent and treat eating disorders and obesity. Neuroimage Clin. Mar. 24, 2015;8:1-31. doi: 10.1016/j.nicl.2015.03.016. eCollection 2015.
Van Baarlen, et al. Differential NF-κB pathways induction by Lactobacillus plantarum in the duodenum of healthy humans correlating with immune tolerance. Proc Natl Acad Sci U S A. Feb. 17, 2009. 106(7):2371-6. doi: 10.1073/pnas.0809919106. Epub Feb. 3, 2009.
Van Den Abbeele, et al, Arabinoxylans and inulin differentially modulate the mucosal and luminal gut microbiota and mucindegradation in humanized rats, Environmental Microbiology 13.10 (Oct. 2011): 2667-2680.
Van Den Abbeele, et al. Microbial Community Development in a Dynamic Gut Model Is Reproducible, Colon Region Specific, and Selective for Bacteroidetes and Clostridium Cluster IX. Appl Environ Microbiol. Aug. 2010;76(15):5237-46. doi: 10.1128/AEM.00759-10. Epub Jun. 18, 2010.
Van Der Ark. Metabolic characterization and viable delivery of Akkermansia muciniphila for its future application. PhD Thesis. Wageningen University. 2018.
Van Passe, et al., The Genome of Akkermansia muciniphila, a Dedicated Intestinal Mucin Degrader, and Its Use in Exploring Intestinal Metagenomes, PLoS One, Mar. 2011, 6(3):e16876, 8 pages.
Van Passel, et al, MetaMining of Metagenomes: Uncovering Akkermansia Diversity and Distribution, Abstracts of the General Meeting of the American Society for Microbiology 110 (2010): N-2237.
Vigsnaes, et al. Gram-negative bacteria account for main differences between faecal microbiota from patients with ulcerative colitis and healthy controls. Benef Microbes. Dec. 1, 2012;3(4):287-97. doi: 10.3920/BM2012.0018.

(56) References Cited

OTHER PUBLICATIONS

Vipperla, et al. Diet, microbiota, and dysbiosis: a 'recipe' for colorectal cancer. Food Funct. Apr. 20, 2016;7(4):1731-40. doi: 10.1039/c5fo01276g.

Vital et al. Revealing the bacterial butyrate synthesis pathways by analyzing (meta)genomic data. mBIO 5(2):e00889-14.

Vol. 104 Chounai saikin No. midare ni yotte okoru kabinsei chou shoukougun [*Irritable bowel syndrome caused by disturbance of intestinal bacteria*], [online], (Jan. 25, 2012), Omron Healthcare Co., Ltd., [retrieved on May 26, 2022], Internet, <https://www.healthcare.omron.co.jp/resource/column/topics/104.html (document showing a well-known technique).

Volkow, et al. Obesity and addiction: neurobiological overlaps. Obes Rev. Jan. 2013;14(1):2-18. doi: 10.1111/j.1467-789X.2012.01031.x. Epub Sep. 27, 2012.

Vrieze, et al. Metabolic effects of transplanting gut microbiota from lean donors to subjects with metabolic syndrome. Diabetologia (2010) 53:[Suppll] p. S44.

Vrieze, et al. The environment within: how gut microbiota may influence metabolism and body composition. Diabetologia. Apr. 2010. 53(4):606-13. doi: 10.1007/s00125-010-1662-7. Epub Jan. 26, 2010.

Vrieze, et al. Transfer of intestinal microbiota from lean donors increases insulin sensitivity in individuals with metabolic syndrome. Gastroenterology. Oct. 2012;143(4):913-6.e7. doi: 10.1053/j.gastro.2012.06.031. Epub Jun. 20, 2012.

Vuong, et al., How the Microbiome Affects Cognition, Mood and Behavior, Abstract, Available at http://www.prohealth.com/library/showarticle.cfm?libid=30495, Accessed on Jul. 13, 2017.

Wang, et al., Low Relative Abundances of the Mucolytic Bacterium Akkermansia muciniphila and *Bifidobacterium* Spp. in Feces of Children with Austism, Applied and Environmental Microbiology, Sep. 2011, vol. 77(18):6718-6721.

Wang, et al. *Staphylococcus epidermidisin* the human skin microbiome mediates fermentation to inhibit the growth of Propionibacterium acnes: implications of probiotics in acne vulgaris. Appl Microbiol Biotechnol. Jan. 2014;98(1):411-24. doi: 10.1007/s00253-013-5394-8. Epub Nov. 22, 2013.

Ward, et al. (2013). Human milk metagenome: a functional capacity analysis. BMC Microbiol. 13:116. doi: 10.1186/1471-2180-13-116.

Watanabe, et al., Bile acids induce energy expenditure by promoting intracellular thyroid hormone activation, Nature, Jan. 26, 2006, 439:484-9.

Wedlake, et al. Fiber in the treatment and maintenance of inflammatory bowel disease: a systematic review of randomized controlled trials. Inflamm Bowel Dis. Mar. 2014;20(3):576-86. doi: 10.1097/01.MIB.0000437984.92565.31.

Wikoffa, et al., Metabolomics analysis reveals large effects of gut microflora on mammalian blood metabolites, PNAS, Mar. 10, 2009, 106(10):3698-3703.

Williams, et al. Discovery and characterization of gut microbiota decarboxylases that can produce the neurotransmitter tryptamine. Cell Host Microbe. Oct. 8, 2014;16(4):495-503. doi: 10.1016/j.chom.2014.09.001. Epub Sep. 25, 2014.

Williams, et al. Evidence that Human Skin Microbiome Dysbiosis Promotes Atopic Dermatitis. J Invest Dermatol. Dec. 2017;137(12):2460-2461. doi: 10.1016/j.jid.2017.09.010.

Williams, et al. The Role of the Skin Microbiome in Atopic Dermatitis. Curr Allergy Asthma Rep. Nov. 2015;15(11):65. doi: 10.1007/s11882-015-0567-4.

Wolever, et al. Do colonic short-chain fatty acids contribute to the long-term adaptation of blood lipids in subjects with type 2 diabetes consuming a high-fiber diet?. Am J Clin Nutr. Jun. 2002;75(6):1023-30. DOI: 10.1093/ajcn/75.6.1023.

Woodard, et al., Probiotics Improve Outcomes After Roux-En-Y Gastric Bypass Surgery: A Prospective Randomized Trial, J Gastrointest Surg, Jul. 2009, 13:1198-1204.

Yabe, et al. Two incretin hormones GLP-1 and GIP: comparison of their actions in insulin secretion and β cell preservation. Prog Biophys Mol Biol. Nov. 2011;107(2):248-56. doi: 10.1016/j.pbiomolbio.2011.07.010. Epub Jul. 28, 2011.

Yadav, et al. Beneficial metabolic effects of a probiotic via butyrate-induced GLP-1 hormone secretion. J Biol Chem. Aug. 30, 2013;288(35):25088-97. doi: 10.1074/jbc.M113.452516. Epub Jul. 8, 2013.

Ye. Intestinal bacteria associated with colitis and inflammatory bowel disease. University of California, Riverside, 2009. ProQuest Dissertations Publishing, (2009). 3389696.

Youssef, et al. Plant-based culture media: Efficiently support culturing rhizobacteria and correctly mirror their in-situ diversity. J Adv Res. Mar. 2016;7(2):305-16. doi: 10.1016/j.jare.2015.07.005. Epub Aug. 29, 2015.

Zeevi, et al. Personalized Nutrition by Prediction of Glycemic Responses. Cell. Nov. 19, 2015;163(5):1079-94. doi: 10.1016/j.cell.2015.11.001.

Zeng, et al. Mechanisms linking dietary fiber, gut microbiota and colon cancer prevention. World J Gastrointest Oncol. Feb. 15, 2014;6(2):41-51. doi: 10.4251/wjgo.v6.i2.41.

Zhang, et al. (2013). Human gut microbiota changes reveal the progression of glucose intolerance. PLOS One 8:e71108. doi: 10.1371/journal.pone.0071108.

Zhang, et al., Human gut microbiota in obesity and after gastric bypass, PNAS, Feb. 17, 2009, 106(7):2365-70.

Zhu, et al. Constructing a Boolean implication network to study the interactions between environmental factors and OTUs. Quantitative Biology. 2014; 2(4):127-141.

Zhu, et al. Gut microbiome and nonalcoholic fatty liver diseases. Pediatr Res. Jan. 2015;77(1-2):245-51. doi: 10.1038/pr.2014.157. Epub Oct. 13, 2014.

Zoetendal, et al. Temperature Gradient Gel Electrophoresis Analysis of 16S rRNA from Human Fecal Samples Reveals Stable and Host-Specific Communities of Active Bacteria. Appl Environ Microbiol. Oct. 1998; 64(10): 3854-3859.

Belzer et al., (2017) "Microbial Metabolic Networks at the Mucus Layer Lead to Diet-Independent Butyrate and Vitamin B12 Production by Intestinal Symbionts", mBIO, 8(5):1-14.

Ottman, N. et al. (2017) "Action and function of Akkermansia muciniphila in microbiome ecology, health and disease", Baillieres best practice research. Clinical gastroenterology, 31(6), pp. 637-642.

Clarke, G. Society for Neuroscience (SfN) 2015 Annual Meeting. Abstract 162.04. Presented Oct. 18, 2015.

European search report and search opinion dated Nov. 12, 2015 for EP Application No. 13754666.9.

Goderska, Different Methods of Probiotics Stabilization, Published Oct. 3, 2012 Agricultural and Food Sciences, DOI: 10.5772/50313 (Year: 2012).

International search report and written opinion dated May 13, 2013 for PCT Application PCT/US2013/028271, Ethicon-Endo-Surgery, Inc. 10 pgs.

International Search Report and Written Opinion, Application No. PCT/US2024/032000 Pendulum Therapeutics, Inc., Date of Mailing Aug. 26, 2024, 10 pgs.

Lambers; et al., "Natural Skin Surface pH is on Average Below 5, Which is Beneficial for Its Resident Flora", International Journal of Cosmetic Science, 2006, 359-370.

Loman et al. High-throughput bacterial genome sequencing: an embarrassment of choice, a world of opportunity. Nature Reviews, Sep. 2012, vol. 10, p. 599-606 (Year: 2012).

Shah, N.P., Ding, W.K., Fallourd, M.J. and Leyer, G (2010), Improving the Stability of Probiotic Bacteria in Model Fruit Juices Using Vitamins and Antioxidants. Journal of Food Scienc, 75: M278-M282. https://doi.org/10.1111/j.1750-3841.2010.01628.x (Year: 2010).

Zhang et al., (2023) "Akkermansia muciniphila Inhibits tryptophan metabolism via the AhR/B-catenin signaling pathway to counter the progression of colorectal cancer." Int. J. Biol. Sci. 2023 vol. 19; Aug. 21, 2023, 4393-4410.

International Search Report and Written Opinion, Application No. PCT/US2024/050356 Pendulum Therapeutics, Inc., Date of Mailing Nov. 26, 2024, 10 pgs.

(56) References Cited

OTHER PUBLICATIONS

Yang, Meng, et al., (2020) Beneficial Effects of Newly Isolated Akkermansia muciniphila Strains from the Human Gut on Obesity and Metabolic Dysregulation, Microorganisms. Sep. 14, 2020; 8, 1413, pp. 1-26.

SEQUENCE LISTING

```
<160> NUMBER OF SEQ ID NOS: 6

<210> SEQ ID NO 1
<211> LENGTH: 1523
<212> TYPE: DNA
<213> ORGANISM: Akkermansia muciniphila

<400> SEQUENCE: 1
aaaattaatt tgatggagag tttgattctg gctcagaacg aacgctggcg gcgtggataa      60
gacatgcaag tcgaacgaga gaattgctag cttgctaata attctctagt ggcgcacggg     120
tgagtaacac gtgagtaacc tgcccccgag agcgggatag ccctgggaaa ctgggattaa     180
taccgcatag tatcgaaaga ttaaagcagc aatgcgcttg gggatgggct cgcggcctat     240
tagttagttg gtgaggtaac ggctcaccaa ggcgatgacg ggtagccggt ctgagaggat     300
gtccggccac actggaactg agacacggtc cagacaccta cgggtggcag cagtcgagaa     360
tcattcacaa tgggggaaac cctgatggtg tgacgccgcg tgggggaatg aaggtcttcg     420
gattgtaaac ccctgtcatg tgggagcaaa ttaaaaagat agtaccacaa gaggaagaga     480
cggctaactc tgtgccagca gccgcggtaa tacagaggtc tcaagcgttg ttcggaatca     540
ctgggcgtaa agcgtgcgta ggctgtttcg taagtcgtgt gtgaaaggcg cgggctcaac     600
ccgcggacgg cacatgatac tgcgagacta gagtaatgga gggggaaccg gaattctcgg     660
```

```
tgtagcagtg aaatgcgtag atatcgagag gaacactcgt ggcgaaggcg ggttcctgga        720
cattaactga cgctgaggca cgaaggccag gggagcgaaa gggattagat accccctgtag       780 tcctggcagt aaacggtgca cgcttggtgt gcggggaatc gaccccctgc gtgccggagc        840
taacgcgtta agcgtgccgc ctggggagta cggtcgcaag attaaaactc aaagaaattg        900
acggggaccc gcacaagcgg tggagtatgt ggcttaattc gatgcaacgc gaagaacctt        960
acctgggctt gacatgtaat gaacaacatg tgaaagcatg cgactcttcg gaggcgttac       1020
acaggtgctg catggccgtc gtcagctcgt gtcgtgagat gtttggttaa gtccagcaac      1080
gagcgcaacc cctgttgcca gttaccagca cgtgaaggtg gggactctgg cgagactgcc      1140
cagatcaact gggaggaagg tggggacgac gtcaggtcag tatggcccct atgcccaggg      1200
ctgcacacgt actacaatgc ccagtacaga ggggccgaa gccgcgaggc ggaggaaatc       1260
ctgaaaactg gcccagttc ggactgtagg ctgcaacccg cctacacgaa gccggaatcg       1320
ctagtaatgg cgcatcagct acggcgccgt gaatacgttc ccgggtcttg tacacaccgc      1380
ccgtcacatc atggaagccg gtcgcacccg aagtatctga agccaaccgc aaggaggcag      1440
ggtcctaagg tgagactggt aactgggatg aagtcgtaac aaggtagccg tagggaacc       1500 tgcggctgga tcacctcctt tct                                               1523

<210> SEQ ID NO 2
<211> LENGTH: 1507
<212> TYPE: DNA
<213> ORGANISM: Akkermansia muciniphila

<400> SEQUENCE: 2
agagtttgat tctggctcag aacgaacgct ggcggcgtgg ataagacatg caagtcgaac         60
gagagaattg ctagcttgct aataattctc tagtggcgca cgggtgagta acacgtgagt        120
aacctgcccc cgagagcggg atagccctgg gaaactggga ttaataccgc atagtatcgc        180
aagattaaag cagcaatgcg cttggggatg ggctcgcggc ctattagtta gttggtgagg        240
taacggctca ccaaggcgat gacgggtagc cggtctgaga ggatgtccgg ccacactgga        300
actgagacac ggtccagaca cctacgggtg gcagcagtcg agaatcattc acaatggggg        360
aaaccctgat ggtgcgacgc cgcgtggggg aatgaaggtc ttcggattgt aaaccctgt        420 catgtgggag caaattaaaa agatagtacc acaagaggag gagacggcta actctgtgcc        480
agcagccgcg gtaatacaga ggtctcaagc gttgttcgga atcactgggc gtaaagcgtg        540
cgtaggctgt ttcgtaagtc gtgtgtgaaa ggcgcgggct caacccgcgg acggcacatg        600
atactgcgag actagagtaa tggaggggga accggaattc tcggtgtagc agtgaaatgc        660
gtagatatcg agaggaacac tcgtggcgaa ggcgggttcc tggacattaa ctgacgctga        720
ggcacgaagg ccaggggagc gaaagggatt agataccct gtagtcctgg cagtaaacgg        780
tgcacgcttg gtgtgcgggg aatcgacccc ctgcgtccg gagctaacgc gttaagcgtg        840
ccgcctgggg agtacggtcg caagattaaa actcaaagaa attgacgggg acccgcacaa        900
gcggtggagt atgtggctta attcgatgca acgcgaagaa ccttacctgg cttgacatg         960 taatgaacaa catgtgaaag catgcgactc ttcggaggcg ttacacaggt gctgcatggc       1020
cgtcgtcagc tcgtgtcgtg agatgtttgg ttaagtccag caacgagcgc aaccccctgtt      1080 gccagttacc agcacgtgaa ggtggggact ctggcgagac tgcccagatc aactgggagg      1140
aaggtgggga cgacgtcagg tcagtatggc ccttatgccc agggctgcac acgtactaca       1200
```

| | |
|---|---|
| atgcccagta cagagggggc cgaagccgcg aggcggagga aatcctaaaa actgggccca | 1260 |
| gttcggactg taggctgcaa cccgcctaca cgaagccgga atcgctagta atggcgcatc | 1320 |
| agctacggcg ccgtgaatac gttcccgggt cttgtacaca ccgcccgtca catcatggaa | 1380 |
| gccggtcgca cccgaagtat ctgaagccaa ccgcaaggag gcagggtcct aaggtgagac | 1440 |
| tggtaactgg gatgaagtcg taacaaggta gccgtagggg aacctgcggc tggatcacct | 1500 |
| cctttct | 1507 |

<210> SEQ ID NO 3
<211> LENGTH: 1504
<212> TYPE: DNA
<213> ORGANISM: Akkermansia muciniphila

<400> SEQUENCE: 3

| | |
|---|---|
| ctggcggcgt ggataagaca tgcaagtcga acgagagaat tgctagcttg ctaataattc | 60 |
| tctagtggcg cacgggtgag taacacgtga gtaacctgcc cccgagagcg ggatagccct | 120 |
| gggaaactgg gattaatacc gcatagtatc gaaagattaa agcagcaatg cgcttgggga | 180 |
| tgggctcgcg gcctattagt tagttggtga ggtaacggct caccaaggcg atgacgggta | 240 |
| gccggtctga gaggatgtcc ggccacactg gaactgagac acggtccaga cacctacggg | 300 |
| tggcagcagt cgagaatcat tcacaatggg ggaaaccctg atggtgcgac gccgcgtggg | 360 |
| ggaatgaagg tcttcggatt gtaaaccct gtcatgtggg agcaaattaa aaagatagta | 420 |
| ccacaagagg aagagacggc taactctgtg ccagcagccg cggtaataca gaggtctcaa | 480 |
| gcgttgttcg gaatcactgg gcgtaaagcg tgcgtaggct gtttcgtaag tcgtgtgtga | 540 |
| aaggcgcggg ctcaacccgc ggacggcaca tgatactgcg agactagagt aatggagggg | 600 |
| gaaccggaat tctcggtgta gcagtgaaat gcgtagatat cgagaggaac actcgtggcg | 660 |
| aaggcgggtt cctggacatt aactgacgct gaggcacgaa ggccagggga gcgaaaggga | 720 |
| ttagataccc ctgtagtcct ggcagtaaac ggtgcacgct tggtgtgcgg ggaatcgacc | 780 |
| ccctgcgtgc cggagctaac gcgttaagcg tgccgcctgg ggagtacggt cgcaagatta | 840 |
| aaactcaaag aaattgacgg ggacccgcac aagcggtgga gtatgtggct taattcgatg | 900 |
| caacgcgaag aaccttacct gggcttgaca tgtaatgaac aacatgtgaa agcatgcgac | 960 |
| tcttcggagg cgttacacag gtgctgcatg gccgtcgtca gctcgtgtcg tgagatgttt | 1020 |
| ggttaagtcc agcaacgagc gcaacccctg ttgccagtta ccagcacgtg aaggtgggga | 1080 |
| ctctggcgag actgcccaga tcaactggga ggaaggtggg gacgacgtca ggtcagtatg | 1140 |
| gcccttatgc ccagggctgc acacgtacta caatgcccag tacagagggg gccgaagccg | 1200 |
| cgaggcggag gaaatcctaa aaactgggcc cagttcggac tgtaggctgc aacccgccta | 1260 |
| cacgaagccg gaatcgctag taatggcgca tcagctacgg cgccgtgaat acgttcccgg | 1320 |
| gtcttgtaca caccgcccgt cacatcatgg aagccggtcg cacccgaagt atctgaagcc | 1380 |
| aaccgcaagg aggcagggtc ctaaggtgag actggtaact gggatgaagt cgtaacaagg | 1440 |
| tagccgtagg ggaacctgcg gctggatcac ctcctttcta tggagcaagt gcacggaagt | 1500 |
| gcac | 1504 |

<210> SEQ ID NO 4
<211> LENGTH: 1438
<212> TYPE: DNA
<213> ORGANISM: Akkermansia muciniphila

<400> SEQUENCE: 4

```
tgctagcttg ctaataattc tctagtggcg cacgggtgag taacacgtga gtaacctgcc      60
cccgagagcg ggatagccct gggaaactgg gattaatacc gcatagtatc gcaagattaa     120
agcagcaatg cgcttgggga tgggctcgcg gcctattagt tagttggtga ggtaacggct     180
caccaaggcg atgacgggta gccggtctga gaggatgtcc ggccacactg gaactgagac     240
acggtccaga cacctacggg tggcagcagt cgagaatcat tcacaatggg ggaaaccctg     300
atggtgcgac gccgcgtggg ggaatgaagg tcttcggatt gtaaacccct gtcatgtggg     360
agcaaattaa aaagatagta ccacaagagg aagagacggc taactctgtg ccagcagccg     420
cggtaataca gaggtctcaa gcgttgttcg gaatcactgg gcgtaaagcg tgcgtaggct     480
gtttcgtaag tcgtgtgtga aggcgcggg ctcaacccgc ggacggcaca tgatactgcg     540
agactagagt aatggagggg gaaccggaat tctcggtgta gcagtgaaat gcgtagatat     600
cgagaggaac actcgtggcg aaggcgggtt cctggacatt aactgacgct gaggcacgaa     660
ggccagggga gcgaaaggga ttagataccc ctgtagtcct ggcagtaaac ggtgcacgct     720
tggtgtgcgg ggaatcgacc ccctgcgtgc cggagctaac gcgttaagcg tgccgcctgg     780
ggagtacggt cgcaagatta aaactcaaag aaattgacgg gacccgcac aagcggtgga     840 gtatgtggct taattcgatg caacgcgaag aaccttacct gggcttgaca tgtaatgaac     900
aacatgtgaa agcatgcgac tcttcggagg cgttacacag gtgctgcatg gccgtcgtca     960
gctcgtgtcg tgagatgttt ggttaagtcc agcaacgagc gcaacccctg ttgccagtta    1020
ccagcacgtg aaggtgggga ctctggcgag actgcccaga tcaactggga ggaaggtggg    1080
gacgacgtca ggtcagtatg gcccttatgc ccagggctgc acacgtacta caatgcccag    1140
tacagagggg gccgaagccg cgaggcgag gaaatcctaa aaactgggcc cagttcggac    1200
tgtaggctgc aacccgccta cacgaagccg gaatcgctag taatggcgca tcagctacgg    1260
cgccgtgaat acgttcccgg gtcttgtaca caccgcccgt cacatcatgg aagccggtcg    1320 caccccgaagt atctgaagcc aaccgcaagg aggcagggtc ctaaggtgag actggtaact    1380
gggatgaagt cgtaacaagg tagccgtagg ggaacctgcg gctggatcac ctccttttc    1438
```

<210> SEQ ID NO 5
<211> LENGTH: 1554
<212> TYPE: DNA
<213> ORGANISM: Akkermansia muciniphila
<220> FEATURE:
<221> NAME/KEY: modified_base
<222> LOCATION: (1537)..(1542)
<223> OTHER INFORMATION: a, c, t, g, unknown or other

<400> SEQUENCE: 5

```
tccagcaatt tcaaaaatta atttgatgga gagtttgatt ctggctcaga acgaacgctg      60
gcggcgtgga taagacatgc aagtcgaacg agagaattgc tagcttgcta ataattctct     120
agtggcgcac gggtgagtaa cacgtgagta acctgccccc gagagcggga tagccctggg     180
aaactgggat taataccgca tagtatcgca agattaaagc agcaatgcgc ttggggatgg     240
gctcgcggcc tattagttag ttggtgaggt aacggctcac caaggcgatg acgggtagcc     300
ggtctgagag gatgtccggc cacactggaa ctgagcacg tccagacac ctacgggtgg     360 cagcagtcga gaatcattca caatggggga accctgatg gtgcgacgcc gcgtggggga     420
atgaaggtct tcggattgta aaccctgtc atgtgggagc aaattaaaaa gatagtacca     480
caagaggaag agacggctaa ctctgtgcca gcagccgcgg taatacagag gtctcaagcg     540
```

```
ttgttcggaa tcactgggcg taaagcgtgc gtaggctgtt tcgtaagtcg tgtgtgaaag      600
gcgcgggctc aacccgcgga cggcacatga tactgcgaga ctagagtaat ggagggggaa      660
ccggaattct cggtgtagca gtgaaatgcg tagatatcga gaggaacact cgtggcgaag      720
gcgggttcct ggacattaac tgacgctgag gcacgaaggc caggggagcg aaagggatta      780
gatacccctg tagtcctggc agtaaacggt gcacgcttgg tgtgcgggga atcgaccccc      840
tgcgtgccgg agctaacgcg ttaagcgtgc cgcctgggga gtacggtcgc aagattaaaa      900
ctcaaagaaa ttgacgggga cccgcacaag cggtggagta tgtggcttaa ttcgatgcaa      960
cgcgaagaac cttacctggg cttgacatgt aatgaacaac atgtgaaagc atgcgactct     1020
tcggaggcgt tacacaggtg ctgcatggcc gtcgtcagct cgtgtcgtga gatgtttggt     1080
taagtccagc aacgagcgca acccctgttg ccagttacca gcacgtgaag gtggggactc     1140
tggcgagact gcccagatca actgggagga aggtgggggac gacgtcaggt cagtatggcc     1200
cttatgccca gggctgcaca cgtactacaa tgcccagtac agaggggggcc gaagccgcga     1260
ggcggaggaa atcctaaaaa ctgggcccag ttcggactgt aggctgcaac ccgcctacac     1320
gaagccggaa tcgctagtaa tggcgcatca gctacggcgc cgtgaatacg ttcccgggtc     1380
ttgtacacac cgcccgtcac atcatggaag ccggtcgcac ccgaagtatc tgaagccaac     1440
cgcaaggagg cagggtccta aggtgagact ggtaactggg atgaagtcgt aacaaggtag     1500
ccgtagggga acctgcggct ggatcacctc ctttctnnnn nnatggagca agta            1554

<210> SEQ ID NO 6
<211> LENGTH: 1507
<212> TYPE: DNA
<213> ORGANISM: Akkermansia muciniphila

<400> SEQUENCE: 6
gagtttgatt ctggctcaga acgaacgctg gcggcgtgga taagacatgc aagtcgaacg       60
agagaattgc tagcttgcta ataattctct agtggcgcac gggtgagtaa cacgtgagta      120
acctgccccc gagagcggga tagccctggg aaactgggat taataccgca tagtatcgaa      180
agattaaagc agcaatgcgc ttggggatgg gctcgcggcc tattagttag ttggtgaggt      240
aacggctcac caaggcgatg acgggtagcc ggtctgagag gatgtccggc cacactggaa      300
ctgagacacg gtccagacac ctacgggtgg cagcagtcga gaatcattca caatggggga      360
aaccctgatg gtgtgacgcc gcgtgggggga atgaaggtct tcggattgta aacccctgtc      420
atgtgggagc aaattaaaaa gatagtacca caagaggaag agacggctaa ctctgtgcca      480
gcagccgcgg taatacagag gtctcaagcg ttgttcggaa tcactgggcg taaagcgtgc      540
gtaggctgtt tcgtaagtcg tgtgtgaaag gcgcgggctc aacccgcgga cggcacatga      600
tactgcgaga ctagagtaat ggagggggaa ccggaattct cggtgtagca gtgaaatgcg      660
tagatatcga gaggaacact cgtggcgaag gcgggttcct ggacattaac tgacgctgag      720
gcacgaaggc caggggagcg aaagggatta gatacccctg tagtcctggc agtaaacggt      780
gcacgcttgg tgtgcgggga atcgaccccc tgcgtgccgg agctaacgcg ttaagcgtgc      840
cgcctgggga gtacggtcgc aagattaaaa ctcaaagaaa ttgacgggga cccgcacaag      900
cggtggagta tgtggcttaa ttcgatgcaa cgcgaagaac cttacctggg cttgacatgt      960
aatgaacaac atgtgaaagc atgcgactct tcggaggcgt tacacaggtg ctgcatggcc     1020
gtcgtcagct cgtgtcgtga gatgtttggt taagtccagc aacgagcgca acccctgttg     1080
ccagttacca gcacgtgaag gtggggactc tggcgagact gcccagatca actgggagga     1140
```

```
aggtggggac gacgtcaggt cagtatggcc cttatgccca gggctgcaca cgtactacaa    1200
tgcccagtac agaggggggcc gaagccgcga ggcggaggaa atcctgaaaa ctgggcccag    1260
ttcggactgt aggctgcaac ccgcctacac gaagccggaa tcgctagtaa tggcgcatca    1320
gctacggcgc cgtgaatacg ttcccgggtc ttgtacacac cgcccgtcac atcatggaag    1380
ccggtcgcac ccgaagtatc tgaagccaac cgcaaggagg cagggtccta aggtgagact    1440
ggtaactggg atgaagtcgt aacaaggtag ccgtagggga acctgcggct ggatcacctc    1500
ctttcta                                                              1507
```

METHODS AND COMPOSITIONS FOR MICROBIAL ENGRAFTMENT

CROSS REFERENCE

This application is a continuation of International Application No. PCT/US2019/042670, filed Jul. 19, 2019, which claims benefit of U.S. Provisional Application No. 62/700,682, filed Jul. 19, 2018, each of which is entirely incorporated herein by reference in its entirety.

SEQUENCE LISTING STATEMENT

The instant application contains a Sequence Listing which has been submitted electronically in ASCII format and is hereby incorporated by reference in its entirety. Said ASCII copy, created on Jan. 15, 2021, is named 46790-732_301_SL.txt and is 12,887 bytes in size.

BACKGROUND

The microbiome can play an important role in maintaining physiological functions of the body. Dysbiosis of the microbiome can lead to various disorders. Microbe-based therapies can be used for maintenance of gut health and treatment of microbiome-related disorders.

BIOLOGICAL DEPOSITS

This application contains a reference to a deposit of biological material. The following biological materials have been deposited with the American Type Culture Collection (ATCC), in Manassas, VA, and bear the following designations, accession numbers and dates of deposit: *Clostridium beijerinckii* (PTA-123634, deposited Dec. 14, 2016); and *Clostridium butyricum* (PTA-123635, deposited Dec. 14, 2016).

SUMMARY

In some aspects, the present disclosure provides a composition comprising a therapeutically-effective amount of an isolated and purified butyrate-producing microbe, wherein engraftment of the butyrate-producing microbe in a subject increases in a presence of a mucin-degrading microbe in the subject.

In some embodiments, the engraftment is indicated by an increased relative abundance of the butyrate-producing microbe in the subject. In some embodiments, the increase in the engraftment of the butyrate-producing microbe is shown by at least about one order of magnitude increase in an amount of a nucleic acid of the butyrate-producing microbe in the subject as measured by qPCR or sequencing relative to a subject lacking the mucin-degrading microbe. In some embodiments, the measuring comprises use of strain-specific primers. In some embodiments, the measuring is performed on a stool sample of the subject after administration of the composition. In some embodiments, the stool sample is collected at least 12 hours after administration of the composition. In some embodiments, the stool sample is collected at least 7 days after administration of the composition. In some embodiments, the composition is formulated for engraftment of the butyrate-producing microbe in a gastrointestinal tract of the subject. In some embodiments, the butyrate-producing microbe and the mucin-degrading microbe co-localize to a region of a gastrointestinal tract of the subject. In some embodiments, the region of the gastrointestinal tract is an ileum region, a colon region, or both. In some embodiments, the subject lacks the butyrate-producing microbe before the engraftment. In some embodiments, the composition further comprises the mucin-degrading microbe. In some embodiments, the subject lacks the mucin-degrading microbe in an absence of the composition. In some embodiments, the butyrate-producing microbe only engrafts in a presence of the mucin-degrading microbe in the composition. In some embodiments, the engraftment of the butyrate-producing microbe occurs after engraftment of the mucin-degrading microbe in the subject. In some embodiments, the butyrate-producing microbe does not engraft in an absence of the mucin-degrading microbe in the subject. In some embodiments, the engraftment of the butyrate-producing microbe increases by at least about 5% in the subject in the presence of the mucin-degrading microbe. In some embodiments, the butyrate-producing microbe comprises a 16S rRNA sequence comprising at least about 95% sequence identity to a 16S rRNA sequence of *Clostridium beijerenckii*. In some embodiments, the butyrate-producing microbe is *Clostridium beijerenckii*. In some embodiments, the butyrate-producing microbe comprises a 16S rRNA sequence comprising at least about 95% sequence identity to a 16S rRNA sequence of *Eubacterium hallii*. In some embodiments, the butyrate-producing microbe is *Eubacterium hallii*. In some embodiments, the butyrate-producing microbe comprises a 16S rRNA sequence comprising at least about 95% sequence identity to a 16S rRNA sequence of *Clostridium butyricum*. In some embodiments, the butyrate-producing microbe is *Clostridium butyricum*. In some embodiments, the butyrate-producing microbe comprises a 16S rRNA sequence comprising at least about 95% sequence identity to a 16S rRNA sequence of *Bifidobacterium infantis*. In some embodiments, butyrate-producing microbe is *Bifidobacterium infantis*. In some embodiments, the mucin-degrading microbe is capable of growth in a culture medium comprising mucin as a primary energy source. In some embodiments, the mucin-degrading microbe comprises a 16S rRNA sequence comprising at least about 95% sequence identity to a 16S rRNA sequence of *Akkermansia muciniphila*. In some embodiments, the mucin-degrading microbe comprises a 16S rRNA sequence comprising at least about 85% identity to a sequence selected from the group consisting of SEQ ID NOS. 1-6. In some embodiments, the mucin-degrading microbe is *Akkermansia muciniphila*. In some embodiments, the composition is formulated for oral delivery. In some embodiments, the composition is formulated as a capsule comprising an enteric coating, and wherein the capsule does not substantially release the butyrate-producing microbe prior to reaching an intestinal region of the subject. In some embodiments, the butyrate-producing microbe and the mucin-degrading microbe are strict anaerobes. In some embodiments, the composition further comprises a prebiotic. In some embodiments, the prebiotic is inulin. In some embodiments, the composition is substantially free of peanut, wheat, soy, shellfish, or a combination thereof. In some embodiments, the composition is formulated as a substantially dry powder. In some embodiments, the butyrate-producing microbe is derived from a non-animal source. In some embodiments, the composition comprises milk. In some embodiments, the composition does not comprise milk.

In some aspects, the present disclosure provides a composition comprising a therapeutically-effective amount of a population of isolated and purified microbes comprising a first microbe and a second microbe, wherein engraftment of the second microbe in a subject requires engraftment of the first microbe in the subject.

In some embodiments, the first microbe engrafts before the second microbe in the subject. In some embodiments, the subject lacks the first microbe, the second microbe, or both, prior to the engraftment of the first microbe, the engraftment of the second microbe, or both. In some embodiments, the engraftment occurs in a gastrointestinal tract of the subject. In some embodiments, the first microbe does not engraft in an absence of the second microbe in the composition. In some embodiments, the engraftment of the first microbe is indicated by an increased relative abundance of the first microbe in the subject. In some embodiments, the engraftment of the second microbe is indicated by an increased relative abundance of the second microbe in the subject. In some embodiments, the engraftment of the second microbe is shown by at least about one order of magnitude increase in an amount of a nucleic acid of the second microbe in the subject as measured by qPCR or sequencing relative to a comparable subject not administered the composition or administered a composition lacking the first microbe. In some embodiments, the measuring comprises use of strain-specific primers. In some embodiments, the measuring is performed on a stool sample of the subject after administration of the composition. In some embodiments, the stool sample is collected at least 12 hours after administration of the composition. In some embodiments, the stool sample is collected at least 7 days after administration of the composition. In some embodiments, the composition is formulated for engraftment of the first or second microbe in a gastrointestinal tract of the subject. In some embodiments, the first and second microbe co-localize to a region of a gastrointestinal tract of the subject. In some embodiments, the region of the gastrointestinal tract is an ileum region, a colon region, or both. In some embodiments, the first microbe is a mucin-degrading microbe. In some embodiments, the mucin-degrading microbe is capable of growth in a culture medium comprising mucin as a primary energy source. In some embodiments, the first microbe comprises a 16S rRNA sequence comprising at least about 95% sequence identity to a 16S rRNA sequence of *Akkermansia muciniphila*. In some embodiments, the first microbe comprises a 16S rRNA sequence comprising at least about 85% identity to a sequence selected from the group consisting of SEQ ID NO. 1-6. In some embodiments, the first microbe is *Akkermansia muciniphila*. In some embodiments, the second microbe is a butyrate-producing microbe. In some embodiments, the second microbe comprises a 16S rRNA sequence comprising at least about 95% sequence identity to a 16S rRNA sequence of *Clostridium beijerenckii*. In some embodiments, the second microbe is *Clostridium beijerenckii*. In some embodiments, the second microbe comprises a 16S rRNA sequence comprising at least about 95% sequence identity to a 16S rRNA sequence of *Eubacterium hallii*. In some embodiments, the second microbe is *Eubacterium hallii*. In some embodiments, the second microbe comprises a 16S rRNA sequence comprising at least about 95% sequence identity to a 16S rRNA sequence of *Clostridium butyricum*. In some embodiments, the second microbe is *Clostridium butyricum*. In some embodiments, the second microbe comprises a 16S rRNA sequence comprising at least about 95% sequence identity to a 16S rRNA sequence of *Bifidobacterium infantis*. In some embodiments, the composition is formulated for oral delivery. In some embodiments, the composition is formulated as a capsule comprising an enteric coating, and wherein the capsule does not substantially release the butyrate-producing microbe prior to reaching an intestine region of the subject. In some embodiments, the first and second microbes are strict anaerobes. In some embodiments, the composition further comprises a prebiotic. In some embodiments, the prebiotic is inulin. In some embodiments, the composition is substantially free of peanut, wheat, soy, shellfish, or a combination thereof. In some embodiments, the first and second microbes are formulated as a substantially dry powder in the composition. In some embodiments, the first and second microbes are derived from a non-animal source. In some embodiments, the composition further comprises milk. In some embodiments, the composition does not comprise milk.

In some aspects, the present disclosure provides a composition comprising a therapeutically-effective amount of a population of isolated and purified microbes comprising a first microbe and a second microbe, wherein engraftment of the second microbe in a subject occurs after engraftment of the first microbe in the subject.

In some embodiments, the engraftment of the first or second microbe is indicated by an increased relative abundance in the subject. In some embodiments, the engraftment of the second microbe is shown by at least about one order of magnitude increase in an amount of a nucleic acid of the second microbe in the subject as measured by qPCR or sequencing relative to a comparable subject not administered the composition or administered a composition lacking the first microbe. In some embodiments, the measuring comprises use of strain-specific primers. In some embodiments, the measuring is performed on a stool sample of the subject after administration of the composition. In some embodiments, the stool sample is collected at least 12 hours after administration of the composition. In some embodiments, the stool sample is collected at least 7 days after administration of the composition. In some embodiments, the engraftment occurs in a gastrointestinal tract of the subject. In some embodiments, the second microbe does not engraft in an absence of the first microbe in the composition. In some embodiments, the first microbe is a mucin-degrading microbe. In some embodiments, the mucin-degrading microbe is capable of growth in a culture medium comprising mucin as a primary energy source. In some embodiments, the first microbe comprises a 16S rRNA sequence comprising at least about 95% sequence identity to a 16S rRNA sequence of *Akkermansia muciniphila*. In some embodiments, the first microbe comprises a 16S rRNA sequence comprising at least about 85% identity to a sequence selected from the group consisting of SEQ ID NO. 1-6. In some embodiments, the first microbe is *Akkermansia muciniphila*. In some embodiments, the second microbe is a butyrate-producing microbe. In some embodiments, the second microbe comprises a 16S rRNA sequence comprising at least about 95% sequence identity to a 16S rRNA sequence of *Clostridium beijerenckii*. In some embodiments, the second microbe is *Clostridium beijerenckii*. In some embodiments, the second microbe comprises a 16S rRNA sequence comprising at least about 95% sequence identity to a 16S rRNA sequence of *Eubacterium hallii*. In some embodiments, the second microbe is *Eubacterium hallii*. In some embodiments, the second microbe comprises a 16S rRNA sequence comprising at least about 95% sequence identity to a 16S rRNA sequence of *Clostridium butyricum*. In some embodiments, the second microbe is *Clostridium butyricum*. In some embodiments, the second microbe comprises a 16S rRNA sequence comprising at least about 95% sequence identity to a 16S rRNA sequence of *Bifidobacterium infantis*. In some embodiments, the second microbe is *Bifidobac-*

*terium infantis.* In some embodiments, the composition is formulated for oral delivery. In some embodiments, the composition is formulated as a capsule comprising an enteric coating, and wherein the capsule does not substantially release the butyrate-producing microbe prior to an intestine of the subject. In some embodiments, the first and second microbes are strict anaerobes. In some embodiments, the composition further comprises a prebiotic. In some embodiments, the prebiotic is inulin. In some embodiments, the composition is substantially free of peanut, wheat, soy, shellfish, or a combination thereof. In some embodiments, the first and second microbes are formulated as a substantially dry powder in the composition. In some embodiments, the first and second microbes are derived from a non-animal source. In some embodiments, the composition further comprises milk. In some embodiments, the composition does not comprise milk.

In some aspects, the present disclosure provides a composition comprising a therapeutically-effective amount of a population of isolated and purified microbes comprising a first microbe, wherein the first microbe does not engraft in a subject in an absence of a second microbe in the subject.

In some embodiments, the composition further comprises the second microbe, wherein the second microbe is isolated and purified. In some embodiments, the second microbe is a mucin-degrading microbe. In some embodiments, the second microbe is capable of growth in a culture medium comprising mucin as a primary energy source. In some embodiments, the second microbe comprises a 16S rRNA sequence comprising at least about 95% sequence identity to a 16S rRNA sequence of *Akkermansia muciniphila*. In some embodiments, the second microbe comprises a 16S rRNA sequence comprising at least about 85% identity to a sequence selected from the group consisting of SEQ ID NO. 1-6. In some embodiments, the second microbe is *Akkermansia muciniphila*. In some embodiments, the first microbe is a butyrate-producing microbe. In some embodiments, the first microbe comprises a 16S rRNA sequence comprising at least about 95% sequence identity to a 16S rRNA sequence of *Clostridium beijerenckii*. In some embodiments, the first microbe is *Clostridium beijerenckii*. In some embodiments, the first microbe comprises a 16S rRNA sequence comprising at least about 95% sequence identity to a 16S rRNA sequence of *Eubacterium hallii*. In some embodiments, the first microbe is *Eubacterium hallii*. In some embodiments, the first microbe comprises a 16S rRNA sequence comprising at least about 95% sequence identity to a 16S rRNA sequence of *Clostridium butyricum*. In some embodiments, the first microbe is *Clostridium butyricum*. In some embodiments, the first microbe comprises a 16S rRNA sequence comprising at least about 95% sequence identity to a 16S rRNA sequence of *Bifidobacterium infantis*. In some embodiments, the first microbe is *Bifidobacterium infantis*. In some embodiments, the engraftment of the first microbe is indicated by an increased relative abundance of the first microbe in the subject. In some embodiments, the engraftment of the first microbe is shown by at least about one order of magnitude increase in an amount of a nucleic acid of the first microbe in the subject as measured by qPCR or sequencing relative to a comparable subject not administered the composition or administered a composition lacking the second microbe. In some embodiments, the measuring comprises use of strain-specific primers. In some embodiments, the measuring is performed on a stool sample of the subject after administration of the composition. In some embodiments, the stool sample is collected at least 12 hours after the administration of the composition. In some embodiments, the stool sample is collected at least 7 days after the administration of the composition. In some embodiments, the composition is formulated for oral delivery. In some embodiments, the composition is formulated as a capsule comprising an enteric coating, and wherein the capsule does not substantially release the butyrate-producing microbe prior to an intestine of the subject. In some embodiments, the first and second microbes are strict anaerobes. In some embodiments, the composition further comprises a prebiotic. In some embodiments, the prebiotic is inulin. In some embodiments, the composition is substantially free of peanut, wheat, soy, shellfish, or a combination thereof. In some embodiments, the first and second microbes are formulated as a substantially dry powder in the composition. In some embodiments, the first and second microbes are derived from a non-animal source. In some embodiments, the composition further comprises milk. In some embodiments, the composition does not comprise milk.

In some aspects, the present disclosure provides a therapeutic composition for administration to a human subject, the therapeutic composition comprising a therapeutically effective amount of an isolated and purified population of substantially dry microbes comprising a first microbe and a second microbe, wherein the population, when administered daily for 28 days to a wild-type rat lacking the first microbe and the second microbe, results in engraftment of the first microbe after one day of administration and engraftment of the second microbe after 7 days of administration in the wild-type rat.

In some embodiments, the engraftment is measured by performing an assay on a stool sample of the wild-type rat. In some embodiments, the assay comprises detecting a nucleic acid of the first microbe and the second microbe in the stool sample. In some embodiments, the population of substantially dry microbes is derived from a non-animal source. In some embodiments, the population of substantially dry microbes is viable in the human subject. In some embodiments, the therapeutic composition is substantially free of peanut, wheat, soy, shellfish, or any combination thereof. In some embodiments, the therapeutic composition comprises milk. In some embodiments, the therapeutic composition does not comprise milk. In some embodiments, the engraftment occurs in a gastrointestinal tract. In some embodiments, the first microbe is a mucin-degrading microbe. In some embodiments, the mucin-degrading microbe is capable of growth in a culture medium comprising mucin as a primary energy source. In some embodiments, the first microbe comprises a 16S rRNA sequence comprising at least about 95% sequence identity to a 16S rRNA sequence of *Akkermansia muciniphila*. In some embodiments, the first microbe comprises a 16S rRNA sequence comprising at least about 85% identity to a sequence selected from the group consisting of SEQ ID NOS. 1-6. In some embodiments, the first microbe is *Akkermansia muciniphila*. In some embodiments, the second microbe is a butyrate-producing microbe. In some embodiments, the second microbe comprises a 16S rRNA sequence comprising at least about 95% sequence identity to a 16S rRNA sequence of *Clostridium beijerenckii*. In some embodiments, the second microbe is *Clostridium beijerenckii*. In some embodiments, the second microbe comprises a 16S rRNA sequence comprising at least about 95% sequence identity to a 16S rRNA sequence of *Eubacterium hallii*. In some embodiments, the second microbe is *Eubacterium hallii*. In some embodiments, the second microbe comprises a 16S rRNA sequence comprising at least about 95% sequence identity to a 16S rRNA sequence of

*Clostridium butyricum*. In some embodiments, the second microbe is *Clostridium butyricum*. In some embodiments, the second microbe comprises a 16S rRNA sequence comprising at least about 95% sequence identity to a 16S rRNA sequence of *Bifidobacterium infantis*. In some embodiments, the second microbe is *Bifidobacterium infantis*. In some embodiments, the composition is formulated for oral delivery. In some embodiments, the composition is formulated as a capsule comprising an enteric coating, and wherein the capsule does not substantially release the butyrate-producing microbe prior to an intestine of the subject. In some embodiments, the first and second microbes are strict anaerobes. In some embodiments, the composition further comprises a prebiotic. In some embodiments, the prebiotic is inulin.

In some aspects, the present disclosure provides a therapeutic composition for administration to a human subject, the therapeutic composition comprising a therapeutically effective amount of an isolated and purified population of substantially dry microbes comprising a first microbe and a second microbe, wherein the population when administered daily for 28 days to a wild-type rat that lacks the first microbe and the second microbe results in an engraftment of the first microbe and the second microbe in a gastrointestinal tract of the wild-type rat, and wherein the second microbe does not engraft in the wild-type rat when administered as a population of microbes lacking the first microbe.

In some embodiments, the engraftment is measured by performing an assay on a stool sample of the wild-type rat. In some embodiments, the assay comprises detecting a nucleic acid of the first microbe and the second microbe in the stool sample. In some embodiments, the population of substantially dry microbes is derived from a non-animal source. In some embodiments, the population of substantially dry microbes is viable in the human subject. In some embodiments, the therapeutic composition is substantially free of peanut, wheat, soy, shellfish, or any combination thereof. In some embodiments, the therapeutic composition comprises milk. In some embodiments, the therapeutic composition does not comprise milk. In some embodiments, the first microbe is a mucin-degrading microbe. In some embodiments, the mucin-degrading microbe is capable of growth in a culture medium comprising mucin as a primary energy source. In some embodiments, the first microbe comprises a 16S rRNA sequence comprising at least about 95% sequence identity to a 16S rRNA sequence of *Akkermansia muciniphila*. In some embodiments, the first microbe comprises a 16S rRNA sequence comprising at least about 85% identity to a sequence selected from the group consisting of SEQ ID NO. 1-6. In some embodiments, the first microbe is *Akkermansia muciniphila*. In some embodiments, the second microbe is a butyrate-producing microbe. In some embodiments, the second microbe comprises a 16S rRNA sequence comprising at least about 95% sequence identity to a 16S rRNA sequence of *Clostridium beijerenckii*. In some embodiments, the second microbe is *Clostridium beijerenckii*. In some embodiments, the second microbe comprises a 16S rRNA sequence comprising at least about 95% sequence identity to a 16S rRNA sequence of *Eubacterium hallii*. In some embodiments, the second microbe is *Eubacterium hallii*. In some embodiments, the second microbe comprises a 16S rRNA sequence comprising at least about 95% sequence identity to a 16S rRNA sequence of *Clostridium butyricum*. In some embodiments, the second microbe is *Clostridium butyricum*. In some embodiments, the second microbe comprises a 16S rRNA sequence comprising at least about 95% sequence identity to a 16S rRNA sequence of *Bifidobacterium infantis*. In some embodiments, the second microbe is *Bifidobacterium infantis*. In some embodiments, the composition is formulated for oral delivery. In some embodiments, the composition is formulated as a capsule comprising an enteric coating, and wherein the capsule does not substantially release the butyrate-producing microbe prior to an intestine of the subject. In some embodiments, the first and second microbes are strict anaerobes. In some embodiments, the composition further comprises a prebiotic. In some embodiments, the prebiotic is inulin.

In some aspects, the present disclosure provides an isolated and purified mucin-degrading microbe comprising a 16S rRNA sequence comprising at least about 85% sequence identity to a sequence selected from the group consisting of SEQ ID NO. 1-6. In some embodiments, the mucin-degrading microbe is capable of growth in a culture medium comprising mucin as a primary energy source. In some embodiments, the microbe comprises a 16S rRNA sequence comprising at least about 95% identity to a sequence selected from the group consisting of SEQ ID NO. 1-6. In some embodiments, the microbe comprises a 16S rRNA sequence comprising at least about 99% identity to a sequence selected from the group consisting of SEQ ID NO. 1-6. In some embodiments, the microbe comprises a 16S rRNA sequence comprising a sequence selected from the group consisting of SEQ ID NO. 1-6.

In some aspects, the present disclosure provides a method for altering a microbiome in a subject in need thereof, the method comprising administering to the subject a composition of the disclosure, thereby altering the microbiome. In some embodiments, the administering treats a disorder in the subject. In some embodiments, the disorder is a metabolic disorder. In some embodiments, the disorder is Type II diabetes. In some embodiments, the disorder is irritable bowel syndrome (IBS). In some embodiments, the disorder is selected from the group consisting of: a metabolic disorder, a skin disorder, a neurological disorder, a dysbiosis, inflammation, or any combination thereof. In some embodiments, the microbiome is a gut microbiome. In some embodiments, the administering is performed after completion of an antibiotic regimen.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 15A indicates the fraction qPCR reactions in which the indicated strains were detected at baseline (week 0), week 4 of administration, week 12 of administration, following a 4 week washout period (week 16). FIG. 15B indicates the fraction qPCR reactions in which the indicated strains were detected at baseline (week 0), and following the washout period (week 16).

DETAILED DESCRIPTION

Figure 1:
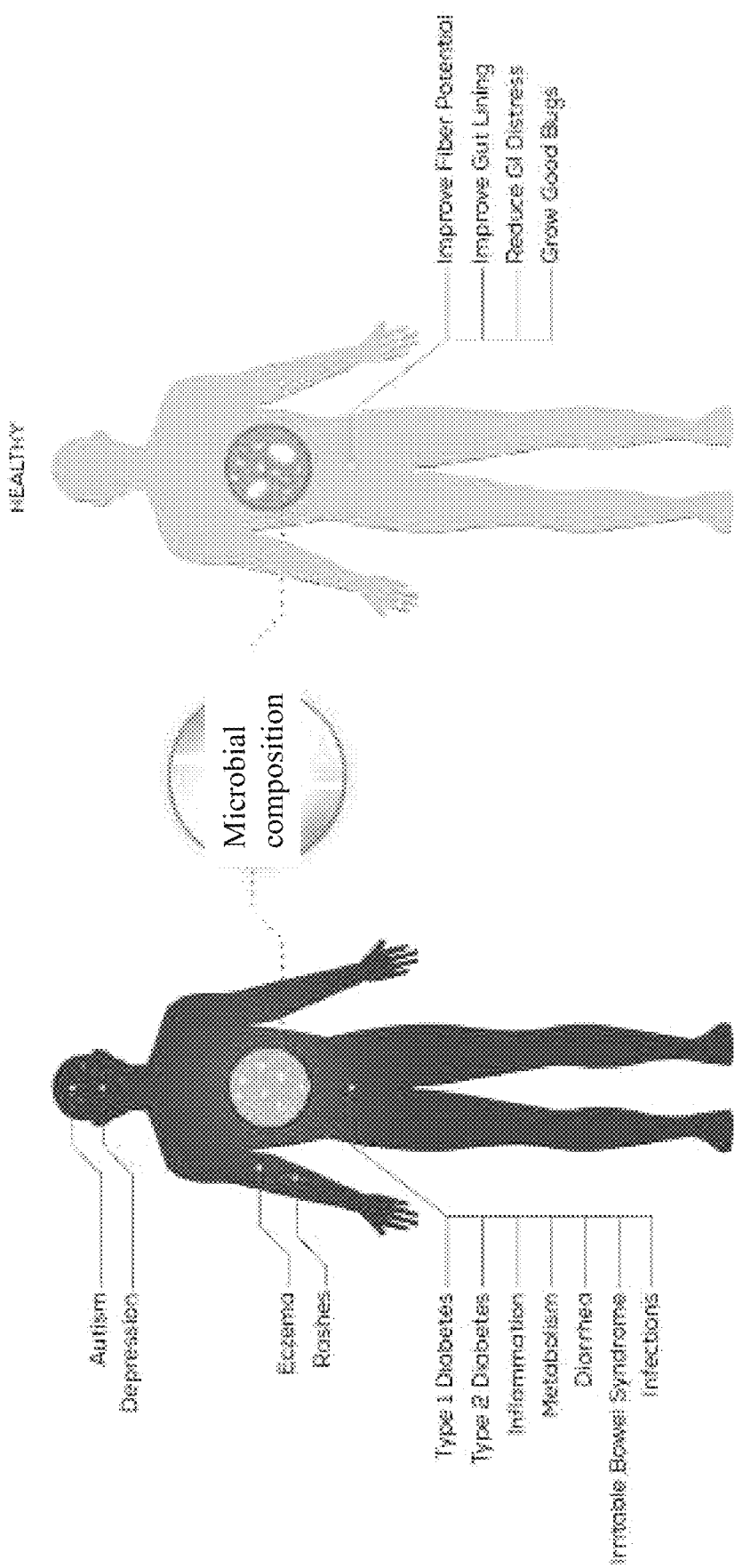
FIG. 1 depicts illustrative microbiome-related health conditions.

As used in the specification and claims, the singular forms "a," "an," and "the" include plural references unless the context clearly dictates otherwise. For example, "a microbe" can include a plurality of microbes.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The terms "microbes" and "microorganisms" can be used interchangeably herein and can refer to bacteria, archaea, eukaryotes (e.g. protozoa, fungi, yeast), and viruses, including bacterial viruses (i.e. phage). A microbe of the disclosure can be an exogenous microbe or an endogenous microbe. An exogenous microbe can be a microbe not found in a host microbiome. An endogenous microbe can be a microbe that is present in a host microbiome.

The term "microbiome," "microbiota," and "microbial habitat" can be used interchangeably herein and can refer to the ecological community of microorganisms that live on or in a subject's body. The microbiome can be comprised of commensal, symbiotic, and/or pathogenic microorganisms. Microbiomes can exist on or in many, if not most parts of the subject. Non-limiting examples of habitats of microbiome can include: body surfaces, body cavities, body fluids, the gut, the colon, skin, skin surfaces, skin pores, vaginal cavity, umbilical regions, conjunctival regions, intestinal regions, the stomach, the nasal cavities and passages, the gastrointestinal tract, the urogenital tracts, saliva, mucus, and feces.

The terms "subject," "individual," "host," and "patient" can be used interchangeably herein and refer to any animal subject, including: humans, laboratory animals, livestock, and household pets. The subject can host a variety of microorganisms. The subject can have different microbiomes in various habitats on and in their body. The subject may be diagnosed or suspected of being at high risk for a disease. The subject may have a microbiome state that is contributing to a disease (i.e. dysbiosis). In some cases, the subject is not necessarily diagnosed or suspected of being at high risk for the disease. In some instances a subject may be suffering from an infection or at risk of developing or transmitting to others an infection.

The terms "treatment" and "treating," as used herein, refer to an approach for obtaining beneficial or desired results including but not limited to a therapeutic benefit and/or a prophylactic benefit. For example, a treatment can comprise administering a system or cell population disclosed herein. By therapeutic benefit is meant any therapeutically relevant improvement in or effect on one or more diseases, conditions, or symptoms under treatment. For prophylactic benefit, a composition can be administered to a subject at risk of developing a particular disease, condition, or symptom, or to a subject reporting one or more of the physiological symptoms of a disease, even though the disease, condition, or symptom may not have yet been manifested.

As used herein, "administer," "administering," "administration," and derivatives thereof refer to the methods that may be used to enable delivery of agents or compositions to the desired site of biological action. These methods include, but are not limited to, parenteral administration (e.g., intravenous, subcutaneous, intraperitoneal, intramuscular, intravascular, intrathecal, intranasal, intravitreal, infusion and local injection), transmucosal injection, oral administration, administration as a suppository, and topical administration.

The term "effective amount" or "therapeutically effective amount" refers to the quantity of a composition, for example a composition comprising microbes of the present disclosure, that is sufficient to result in a desired activity upon administration to a subject in need thereof. Within the context of the present disclosure, the term "therapeutically effective" refers to that quantity of a composition that is sufficient to delay the manifestation, arrest the progression, relieve or alleviate at least one symptom of a disorder treated by the methods of the present disclosure.

The terms "16S", "16S ribosomal subunit", and "16S ribosomal RNA (rRNA)" can be used interchangeably herein and can refer to a component of a small subunit (e.g., 30S) of a prokaryotic (e.g., bacteria, archaea) ribosome. The 16S rRNA is highly conserved evolutionarily among species of microorganisms. Consequently, sequencing of the 16S ribosomal subunit can be used to identify and/or compare microorganisms present in a sample (e.g., a microbiome).

The terms "23S", "23S ribosomal subunit", and "23S ribosomal RNA (rRNA)" can be used interchangeably herein and can refer to a component of a large subunit (e.g., 50S) of a prokaryotic (e.g., bacteria, archaea) ribosome. Sequencing of the 23S ribosomal subunit can be used to identify and/or compare microorganisms present in a sample (e.g., a microbiome).

The term "percent (%) identity," as used herein, refers to the percentage of amino acid or nucleic acid residues of a candidate sequence that are identical to the amino acid or nucleic acid residues of a reference sequence after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment, for purposes of determining percent identity, can be achieved in various ways that are within the skill in the art, for instance, using publicly available computer software such as BLAST, ALIGN, or Megalign (DNASTAR) software. Percent identity of two sequences can be calculated by aligning a test sequence with a comparison sequence using BLAST, determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence.

The term "engraftment", also known as colonization, can occur when a microbe becomes a part of a host's microbiome. Engraftment can lead to an increase in a relative abundance of a microbe in a subject, for example, upon administration of the microbe. A microbe to be engrafted in a subject can be an exogenous microbe (e.g., a microbe that the host lacks prior to administration of the microbe). Alternatively, a microbe to be engrafted in a subject can be an endogenous microbe (e.g., a microbe that is already present in the host but may be administered to increase concentration or enhance engraftment of other microbes in a composition).

Disclosed herein are compositions and methods to enhance engraftment of microbes (e.g., exogenous microbes). As illustrated in FIG. 1, the microbial compositions can be administered for maintenance of gastrointestinal health, treatment of dysbiosis, treatment of a health condition, or any combination thereof.

Figure 2:
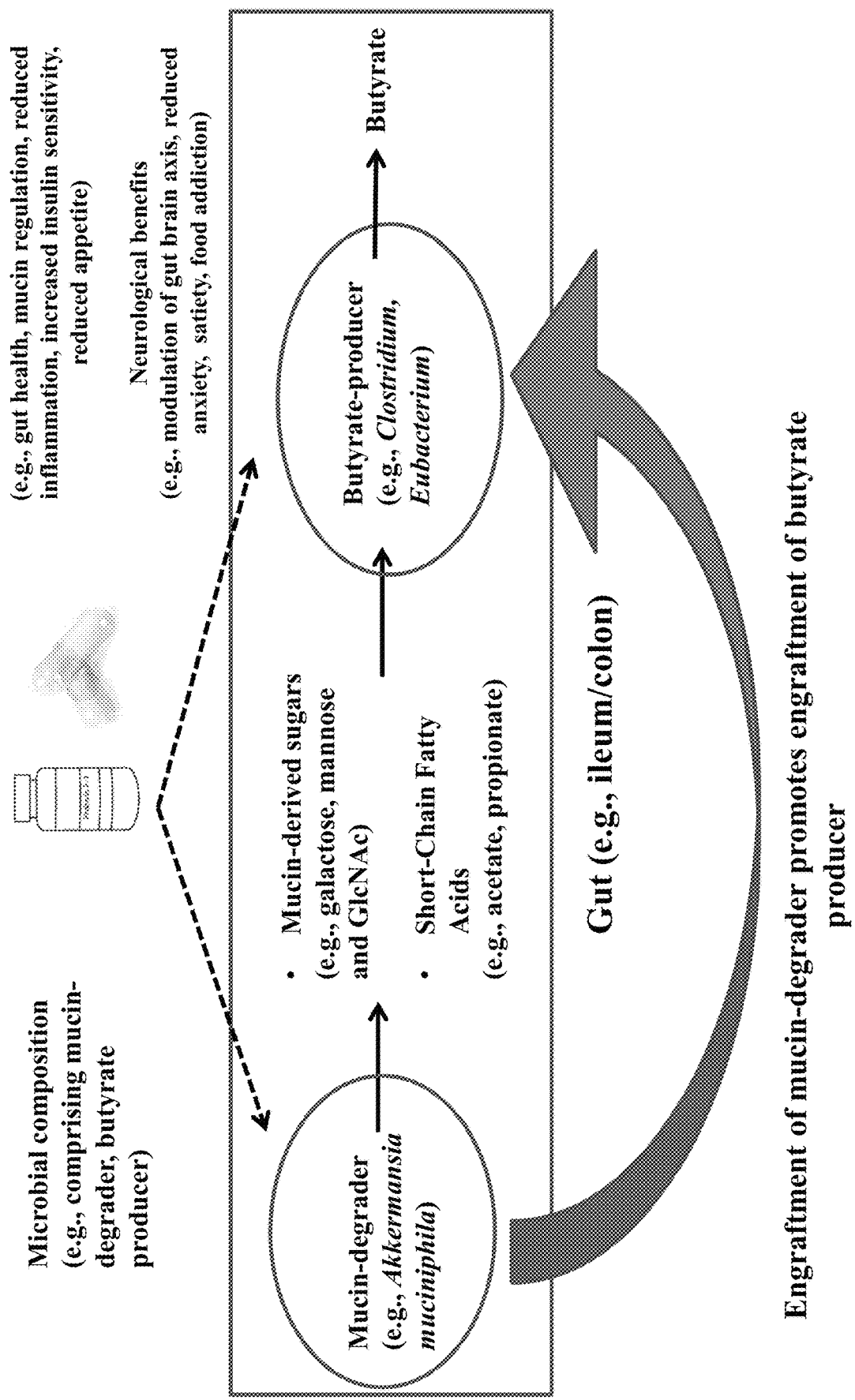
FIG. 2 depicts an illustrative role of a mucin-degrading microbe in enhancing engraftment of a butyrate-producing microbe. A mucin-degrading microbe such as *Akkermansia muciniphila* can degrade host mucin to produce sugars that can be utilized as an energy source by a butyrate-producing microbe. Additionally, the mucin-degrader can produce short-chain fatty acids that can be used as a substrate for butyrate-production by the butyrate producer. Engraftment of exogenous microbes (e.g. microbes administered to a subject, distinguishable from endogenous microbes in a microbiome of a subject) can result in health benefits.

Engraftment of microbes such as those administered in a microbial composition can be enhanced by an engraftment-enhancing microbe, for example, a mucin-degrading microbe. The engraftment-enhancing microbe can be present in the composition, in the subject (e.g., endogenous), or both. FIG. 2 depicts an illustrative role of a mucin-degrading microbe in enhancing engraftment of a butyrate-producing microbe. A mucin-degrading microbe such as *Akkermansia muciniphila* can degrade host mucin to produce sugars that can be utilized as an energy source by a butyrate-producing microbe. Additionally, the mucin-degrader can produce short-chain fatty acids that can be used as a substrate for butyrate-production by the butyrate producer. Engraftment of the administered microbes can then result in butyrate-associated health benefits in the subject.

An illustrative engraftment-enhancing composition of the disclosure can comprise an isolated and purified first microbe, and an isolated and purified second microbe, wherein engraftment of the second microbe in a subject requires engraftment of the first microbe, for example, prior to engraftment of the second microbe. The first microbe can be a mucin-degrading microbe. The second microbe can be a butyrate-producing microbe.

Another illustrative engraftment-enhancing composition of the disclosure can comprise an isolated and purified first microbe, and an isolated and purified second microbe, wherein engraftment of the second microbe occurs after engraftment of the first microbe. The first microbe can be a mucin-degrading microbe. The second microbe can be a butyrate-producing microbe.

Another illustrative engraftment-enhancing composition of the disclosure can comprise an isolated and purified first microbe, and an isolated and purified second microbe, wherein the second microbe does not engraft in the absence of the first microbe. The first microbe can be a mucin-degrading microbe. The second microbe can be a butyrate-producing microbe.

The disclosure also provides compositions and methods to enhance engraftment of a butyrate-producing microbe. An illustrative composition comprises an isolated and purified butyrate-producing microbe, wherein engraftment of the butyrate-producing microbe increases in the presence of a mucin-degrading microbe. The mucin-degrading microbe can be co-administered with the butyrate-producing microbe. The mucin-degrading microbe can be administered prior to administering the butyrate-producing microbe. The mucin-degrading microbe can be present in the subject prior to administration of the butyrate-producing microbe.

The disclosure also provides methods for isolating mucin-degrading microbes. An illustrative method comprises using a selective growth media, e.g., media comprising mucin as an energy source.

The disclosure also provides methods for stool sample collection. In some cases, the stool sample can be collected outside of a human body with the aid of mechanical tools or toilet seat sampling device attachments. In some cases, the stool sample can be collected in situ (i.e. inside the human body), for example, by a remotely controlled preservation apparatus.

The disclosure also provides methods for microbiome profiling to assess engraftment of the microbes. Non-limiting exemplary methods include qPCR, sequencing, mass spectrometry, and metabolite profiling. Different methods of microbiome profiling can be used in parallel to assess sample aliquots from the same biological sample (e.g. entire stool sample) for more accurate evaluation.

A composition of the disclosure can comprise a mucin-degrading microbe. A mucin-degrading microbe can be a microbe that can degrade mucin. A mucin-degrading microbe can be a microbe that can grow on a selective growth medium comprising mucin as the primary energy source. A mucin-degrading microbe can be *Akkermansia muciniphila*. A mucin-degrading microbe can be a microbe with a 16S rRNA sequence comprising at least about 85%, 90%, 91%, 92%, 93%, 94%, 95%, 96%, 97%, 98, 99%, or 99.5% sequence identity to a 16S rRNA sequence selected from the group consisting of SEQ ID NOS: 1-6. A mucin-degrading microbe can be a microbe comprising a 16S rRNA sequence selected from the group consisting of SEQ ID NOS: 1-6.

A composition of the disclosure can comprise a butyrate-producing microbe. A butyrate-producing microbe can be a microbe that can produce butyrate. Non-limiting examples of butyrate-producing microbes include *Clostridium beijerinckii, Clostridium butyricum, Clostridium indolis, Eubacterium hallii, Bifidobacterium adolescentis, Bifidobacterium infantis, Bifidobacterium longum,* and *Faecalibacterium prausnitzii*.

A composition of the disclosure can comprise a microbe encoding a gene involved in butyrate production, for example, butyryl-CoA dehydrogenase, beta-hydroxybutyryl-CoA dehydrogenase or 3-hydroxybutyryl-CoA dehydrogenase, crotonase, electron transfer protein a, electron transfer protein b, or thiolase. A composition of the disclosure can comprise a microbe comprising a gene with at least about 85%, 87%, 90%, 92%, 95%, 96%, 97%, 98%, 99%, or 99.5%, or with 100% sequence identity to a gene selected from the group consisting of butyryl-CoA dehydrogenase, beta-hydroxybutyryl-CoA dehydrogenase or 3-hydroxybutyryl-CoA dehydrogenase, crotonase, electron transfer protein a, electron transfer protein b, and thiolase.

A composition of the disclosure can comprise a combination of microbes for producing butyrate in a subject. For example, the combination can comprise a first microbe and a second microbe. The first microbe can produce intermediate molecules (e.g. lactate, acetate, mucin-derived sugars) when given an energy source (e.g. fiber). The second microbe can convert the intermediate molecules produced by the first microbe into butyrate. Non-limiting examples of a microbe that can produce intermediate molecules for butyrate production include *Akkermansia muciniphila, Bifidobacterium adolescentis, Bifidobacterium infantis* and *Bifidobacterium longum*. Non-limiting examples of a microbe that can use the intermediate molecules to produce butyrate include *Clostridium beijerinckii, Clostridium butyricum, Clostridium indolis, Eubacterium hallii,* and *Faecalibacterium prausnitzii*. A composition can comprise at least one microbe for production of butyrate-intermediate molecules and at least one microbe for conversion of the butyrate intermediate to butyrate. The composition can additionally comprise a substrate for the first microbe that produces the butyrate intermediate. In one non-limiting example, a composition can comprise *Akkermansia muciniphila, Bifidobacterium infantis, Clostridium beijerinckii, Clostridium butyricum,* and *Eubacterium hallii*. In another illustrative example, a composition can comprise *Akkermansia muciniphila,* and *Clostridium indolis*. In another illustrative example, a composition can comprise *Akkermansia muciniphila,* and any one or more of *Bifidobacterium adolescentis, Bifidobacterium infantis, Bifidobacterium longum, Faecalibacterium prausnitzii, Clostridium beijerinckii, Clostridium butyricum, Clostridium indolis,* and *Eubacterium hallii*. In another illustrative example, a composition can comprise *Akkermansia muciniphila,* and *Bifidobacterium infantis*. In another non-limiting example, a composition can comprise *Akkermansia muciniphila* and *Clostridium beijerinckii*. In another non-limiting example, a composition can comprise *Akkermansia muciniphila* and *Clostridium butyricum*. In another non-limiting example, a composition can comprise *Akkermansia muciniphila* and *Bifidobacterium adolescentis*. In another non-limiting example, a composition can comprise *Akkermansia muciniphila* and *Bifidobacterium longum*. In another non-limiting example, a composition can comprise *Akkermansia muciniphila* and *Faecalibacterium prausnitzii*. In another non-limiting example, a composition can comprise *Bifidobacterium adolescentis* and *Clostridium indolis*. In another illustrative example, a composition can comprise *Akkermansia muciniphila, Bifidobacterium infantis, Clostridium beijerinckii, Clostridium butyricum,* and, *Eubacterium hallii*. In another non-limiting example, a composition can comprise *Bifidobacterium longum,* and *Faecalibacterium prausnitzii*. In another non-limiting example, a composition can comprise *Bifidobacterium infantis, Clostridium beijerinckii,* and *Clostridium butyricum*. In another non-limiting example, a composition can comprise *Bifidobacterium infantis, Clostridium beijerinckii, Clostridium butyricum,* and *Akkermansia muciniphila*. In another non-limiting example, a composition can comprise *Clostridium beijerinckii, Clostridium butyricum,* and *Akkermansia muciniphila*. In another non-limiting example, a composition can comprise *Bifidobacterium infantis, Clostridium beijerinckii, Clostridium butyricum,* and *Akkermansia muciniphila*. In another non-limiting example, a composition can comprise *Akkermansia muciniphila* and *Eubacterium hallii*.

A composition of the disclosure can comprise at least 1, 2, 3, 4, 5, 6, 7, 8, 9, or 10 microorganisms, wherein the microorganisms can comprise a rRNA sequence (e.g., 16S rRNA, 23S rRNA, and/or internal transcribed spacer) comprising at least about 85%, 90%, 91%, 92%, 93%, 94%, 95%, 96%, 97%, 98, 99%, or 99.5% sequence identity to a rRNA (e.g., 16S rRNA, 23S rRNA, and/or internal transcribed spacer) sequence of a microorganism selected from the group consisting of *Akkermansia muciniphila, Anaerostipes caccae, Bacteroides* stercoris, *Bifidobacterium adolescentis, Bifidobacterium bifidum, Bifidobacterium infantis, Bifidobacterium longum, Butyrivibrio fibrisolvens, Clostridium acetobutylicum, Clostridium aminophilum, Clostridium beijerinckii, Clostridium butyricum, Clostridium colinum, Clostridium coccoides, Clostridium indolis, Clostridium nexile, Clostridium orbiscindens, Clostridium propionicum, Clostridium xylanolyticum, Collinsella aerofaciens, Enterococcus faecium, Eubacterium hallii, Eubacterium rectale, Faecalibacterium prausnitzii, Fibrobacter succinogenes, Lactobacillus acidophilus, Lactobacillus brevis, Lactobacillus bulgaricus, Lactobacillus casei, Lactobacillus caucasicus, Lactobacillus fermentum, Lactobacillus helveticus, Lactobacillus lactis, Lactobacillus plantarum, Lactobacillus reuteri, Lactobacillus rhamnosus, Oscillospira guilliermondii, Roseburia cecicola, Roseburia inulinivorans, Ruminococcus faecis, Ruminococcus flavefaciens, Ruminococcus gnavus, Ruminococcus obeum, Stenotrophomonas nitritireducens, Streptococcus cremoris, Streptococcus faecium, Streptococcus infantis, Streptococcus mutans, Streptococcus thermophilus, Anaerofustis stercorihominis, Anaerostipes hadrus, Anaerotruncus colihominis, Clostridium sporogenes, Clostridium tetani, Coprococcus, Coprococcus eutactus, Eubacterium cylindroides, Eubacterium dolichum, Eubacterium ventriosum, Roseburia faeccis, Roseburia hominis, Roseburia intestinalis, Lacatobacillus bifidus, Lactobacillus johnsonii, Lactobacilli, Acidaminococcus fermentans, Acidaminococcus intestine, Blautia hydrogenotrophica, Citrobacter amalonaticus, Citrobacter freundii, Clostridium aminobutyricum Clostridium bartlettii, Clostridium cochlearium, Clostridium kluyveri, Clostridium limosum, Clostridium malenominatum, Clostridium pasteurianum, Clostridium peptidivorans, Clostridium saccharobutylicum, Clostridium sporosphaeroides, Clostridium sticklandii, Clostridium subterminale, Clostridium symbiosum, Clostridium tetanomorphum, Eubacterium oxidoreducens, Eubacterium pyruvativorans, Methanobrevibacter smithii, Morganella morganii, Peptoniphilus asaccharolyticus,* and *Peptostreptococcus.*

A composition of the disclosure can comprise one or more isolated and purified microorganisms selected from the group consisting of *Akkermansia muciniphila, Anaerostipes*

*caccae, Bacteroides stercoris, Bifidobacterium adolescentis, Bifidobacterium bifidum, Bifidobacterium infantis, Bifidobacterium longum, Butyrivibrio fibrisolvens, Clostridium acetobutylicum, Clostridium aminophilum, Clostridium beijerinckii, Clostridium butyricum, Clostridium colinum, Clostridium coccoides, Clostridium indolis, Clostridium nexile, Clostridium orbiscindens, Clostridium propionicum, Clostridium xylanolyticum, Collinsella aerofaciens, Enterococcus faecium, Eubacterium hallii, Eubacterium rectale, Faecalibacterium prausnitzii, Fibrobacter succinogenes, Lactobacillus acidophilus, Lactobacillus brevis, Lactobacillus bulgaricus, Lactobacillus casei, Lactobacillus caucasicus, Lactobacillus fermentum, Lactobacillus helveticus, Lactobacillus lactis, Lactobacillus plantarum, Lactobacillus reuteri, Lactobacillus rhamnosus, Oscillospira guilliermondii, Roseburia cecicola, Roseburia inulinivorans, Ruminococcus faecis, Ruminococcus flavefaciens, Ruminococcus gnavus, Ruminococcus obeum, Stenotrophomonas nitritireducens, Streptococcus cremoris, Streptococcus faecium, Streptococcus infantis, Streptococcus mutans, Streptococcus thermophilus, Anaerofustis stercorihominis, Anaerostipes hadrus, Anaerotruncus colihominis, Clostridium sporogenes, Clostridium tetani, Coprococcus, Coprococcus eutactus, Eubacterium cylindroides, Eubacterium dolichum, Eubacterium ventriosum, Roseburia faeccis, Roseburia hominis, Roseburia intestinalis, Lacatobacillus bifidus, Lactobacillus johnsonii, Lactobacilli, Acidaminococcus fermentans, Acidaminococcus intestine, Blautia hydrogenotrophica, Citrobacter amalonaticus, Citrobacter freundii, Clostridium aminobutyricum Clostridium bartlettii, Clostridium cochlearium, Clostridium kluyveri, Clostridium limosum, Clostridium malenominatum, Clostridium pasteurianum, Clostridium peptidivorans, Clostridium saccharobutylicum, Clostridium sporosphaeroides, Clostridium sticklandii, Clostridium subterminale, Clostridium symbiosum, Clostridium tetanomorphum, Eubacterium oxidoreducens, Eubacterium pyruvativorans, Methanobrevibacter smithii, Morganella morganii, Peptoniphilus asaccharolyticus,* and *Peptostreptococcus.*

A composition of the disclosure can comprise one or more microorganisms from a genus selected from the group consisting of *Akkermansia, Clostridium, Eubacterium, Bifidobacterium,* and *Faecalibacterium.*

A composition of the disclosure can comprise one or more microorganisms from a family selected from the group consisting of Alcaligenaceae, Bifidobacteriaceae, Bacteroidaceae, Clostridiaceae, Coriobacteriaceae, Enterobacteriaceae, Enterococcaceae, Erysipelotricaceae, Eubacteriaceae, Incertae-Cedis-XIII, Incertae-Sedis-XIV, Lachnospiraceae, Lactobacilluseae, Pasturellaceae, Peptostreptococcaceae, Porphyromonadaceae, Prevotellaceae, Rikenellaceae, Ruminococcaceae, Streptococcaceae, Veillonellaceae, and Verrucomicrobiaceae.

A composition of the disclosure can comprise one or more microorganisms from a phylum selected from the group consisting of Actinobacteria, Bacteroidetes, Cyanobacteria, Firmicutes, Fusobacteria, Proteobacteria, Spirochaetes, Tenericutes, and Verrucomicrobia.

A composition can comprise a therapeutically-effective amount of an isolated and purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from an *Akkermansia.*

A composition can comprise a therapeutically-effective amount of an isolated and purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from a *Bifidobacterium.*

A composition can comprise a therapeutically-effective amount of an isolated and purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from a *Clostridium.*

A composition can comprise a therapeutically-effective amount of an isolated and purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from a *Eubacterium.*

A composition can comprise a therapeutically-effective amount of an isolated and purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from a *Verrucomicrobium.*

A composition can comprise a therapeutically-effective amount of an isolated and purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from a Firmicute.

A composition can comprise a therapeutically-effective amount of an isolated and purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from a *Lactobacillus* species. In some cases, a composition does not comprise a *Lactobacillus* species.

A composition can comprise a therapeutically-effective amount of a population of isolated and purified microbes, wherein the population of isolated and purified microbes comprises one or more microbes with a rRNA (e.g., 16S rRNA, 23S rRNA, and/or internal transcribed spacer) sequence comprising at least about: 70%, 75%, 80%, 85%, 87%, 90%, 91%, 92%, 93%, 94%, 95%, 96%, 97%, 98%, 99%, 99.5%, or 100% sequence identity to a rRNA sequence from a microbe selected from the group consisting of: *Lactobacillus reuteri* (e.g., *Lactobacillus reuteri* RC-14, *Lactobacillus reuteri* L22), *Streptococcus mutans, Stenotrophomonas nitritireducens,* and any combination thereof. A composition can comprise a therapeutically-effective amount of a population of isolated and purified microbes-selected from the group consisting of: *Lactobacillus reuteri* (e.g., *Lactobacillus reuteri* RC-14, *Lactobacillus reuteri* L22), *Streptococcus mutans, Stenotrophomonas nitritireducens,* and any combination thereof.

A composition can comprise a therapeutically-effective amount of a population of isolated and purified microbes, wherein the population of isolated and purified microbes comprises one or more microbes with a rRNA (e.g., 16S rRNA, 23S rRNA, and/or internal transcribed spacer) sequence comprising at least about: 70%, 75%, 80%, 85%, 87%, 90%, 91%, 92%, 93%, 94%, 95%, 96%, 97%, 98%, 99%, 99.5%, or 100% sequence identity to a rRNA sequence from a microbe selected from the group consisting of: *Lactobacillus rhamnosus, Faecalibacterium prausnitzii, Oscillospira guilliermondii, Clostridium orbiscindens, Clostridium colinum, Clostridium aminophilum, Ruminococcus obeum,* and any combination thereof. A composition can comprise a therapeutically-effective amount of a population of isolated and purified microbes selected from the group consisting of: *Lactobacillus rhamnosus, Faecalibacterium prausnitzii, Oscillospira guilliermondii, Clostridium orbiscindens, Clostridium colinum, Clostridium aminophilum, Ruminococcus obeum*, and any combination thereof.

A composition can comprise a therapeutically-effective amount of a population of isolated and purified microbes, wherein the population of isolated and purified microbes comprises one or more microbes with a rRNA (e.g., 16S rRNA, 23S rRNA, and/or internal transcribed spacer) sequence comprising at least about: 70%, 75%, 80%, 85%, 87%, 90%, 91%, 92%, 93%, 94%, 95%, 96%, 97%, 98%, 99%, 99.5%, or 100% sequence identity to a rRNA sequence from a microbe selected from the group consisting of: *Akkermansia muciniphila, Bifidobacterium adolescentis, Bifidobacterium infantis, Bifidobacterium longum, Clostridium beijerinckii, Clostridium butyricum, Clostridium indolis, Eubacterium hallii*, and any combination thereof. A composition can comprise a therapeutically-effective amount of a population of isolated and purified microbes selected from the group consisting of: *Akkermansia muciniphila, Bifidobacterium adolescentis, Bifidobacterium infantis, Bifidobacterium longum, Clostridium beijerinckii, Clostridium butyricum, Clostridium indolis, Eubacterium hallii*, and any combination thereof.

A composition can comprise a therapeutically-effective amount of a population of isolated and purified microbes, wherein the population of isolated and purified microbes comprises a microbe with a rRNA (e.g., 16S rRNA, 23S rRNA, and/or internal transcribed spacer) sequence comprising at least about: 70%, 75%, 80%, 85%, 87%, 90%, 91%, 92%, 93%, 94%, 95%, 96%, 97%, 98%, 99%, 99.5%, or 100% sequence identity to a rRNA sequence from a microbe selected from the group consisting of: *Akkermansia muciniphila, Clostridium beijerinckii, Clostridium butyricum, Eubacterium hallii*, and any combination thereof. A composition can comprise a therapeutically-effective amount of a population of isolated and purified microbes selected from the group consisting of: *Akkermansia muciniphila, Clostridium beijerinckii, Clostridium butyricum, Eubacterium hallii*, and any combination thereof.

A composition can comprise a therapeutically-effective amount of a population of isolated and purified microbes, wherein the population of isolated and purified microbes comprises a microbe with a rRNA (e.g., 16S rRNA, 23S rRNA, and/or internal transcribed spacer) sequence comprising at least about: 70%, 75%, 80%, 85%, 87%, 90%, 91%, 92%, 93%, 94%, 95%, 96%, 97%, 98%, 99%, 99.5%, or 100% sequence identity to a rRNA sequence from a microbe selected from the group consisting of: *Clostridium beijerinckii, Clostridium butyricum, Bifidobacterium infantis*, or any combination thereof. A composition can comprise a therapeutically-effective amount of a population of isolated and purified microbes selected from the group consisting of: *Clostridium beijerinckii, Clostridium butyricum, Bifidobacterium infantis*, and any combination thereof.

A composition can comprise a therapeutically-effective amount of a population of isolated and purified microbes, wherein the population of isolated and purified microbes comprises a microbe with a rRNA (e.g., 16S rRNA, 23S rRNA, and/or internal transcribed spacer) sequence comprising at least about: 70%, 75%, 80%, 85%, 87%, 90%, 91%, 92%, 93%, 94%, 95%, 96%, 97%, 98%, 99%, 99.5%, or 100% sequence identity to a rRNA sequence from a microbe selected from the group consisting of: *Clostridium beijerinckii, Clostridium butyricum, Bifidobacterium infantis, Eubacterium hallii, Akkermansia muciniphila*, or any combination thereof. A composition can comprise a population of isolated and purified microbes selected from the group consisting of *Clostridium beijerinckii, Clostridium butyricum, Bifidobacterium infantis, Eubacterium hallii, Akkermansia muciniphila*, and any combination thereof.

A composition can comprise a therapeutically-effective amount of a population of isolated and purified microbes, wherein the population of isolated and purified microbes comprises one or more microbes with a rRNA (e.g., 16S rRNA, 23S rRNA, and/or internal transcribed spacer) sequence comprising at least about: 70%, 75%, 80%, 85%, 87%, 90%, 91%, 92%, 93%, 94%, 95%, 96%, 97%, 98%, 99%, 99.5%, or 100% sequence identity to a rRNA sequence from a microbe selected from the group consisting of: *Akkermansia muciniphila, Bifidobacterium adolescentis, Bifidobacterium infantis, Bifidobacterium longum, Clostridium beijerinckii, Clostridium butyricum, Clostridium indolis, Eubacterium hallii, Faecalibacterium prausnitzii*, and any combination thereof. A composition can comprise a population of isolated and purified microbes selected from the group consisting of *Akkermansia muciniphila, Bifidobacterium adolescentis, Bifidobacterium infantis, Bifidobacterium longum, Clostridium beijerinckii, Clostridium butyricum, Clostridium indolis, Eubacterium hallii, Faecalibacterium prausnitzii*, and any combination thereof.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Akkermansia muciniphila*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Anaerostipes caccae*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Bifidobacterium adolescentis*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Bifidobacterium bifidum*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Bifidobacterium infantis*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Bifidobacterium longum*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Butyrivibrio fibrisolvens*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Clostridium acetobutylicum*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Clostridium aminophilum*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Clostridium beijerinckii*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Clostridium butyricum*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Clostridium colinum*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Clostridium coccoides*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Clostridium indolis*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Clostridium nexile*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Clostridium orbiscindens*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Clostridium propionicum*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Clostridium xylanolyticum*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Enterococcus faecium*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Eubacterium hallii*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Eubacterium rectale*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Faecalibacterium prausnitzii*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Fibrobacter succinogenes*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Lactobacillus acidophilus*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Lactobacillus brevis*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Lactobacillus bulgaricus*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Lactobacillus casei*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Lactobacillus caucasicus*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Lactobacillus fermentum.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Lactobacillus helveticus.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Lactobacillus lactis.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Lactobacillus plantarum*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Lactobacillus reuteri.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Lactobacillus rhamnosus.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Oscillospira guilliermondii.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Roseburia cecicola.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Roseburia inulinivorans.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Ruminococcus flavefaciens.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Ruminococcus gnavus.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Ruminococcus obeum.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Stenotrophomonas nitritireducens.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Streptococcus cremoris.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Streptococcus faecium.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Streptococcus infantis.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Streptococcus mutans.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Streptococcus thermophilus.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Anaerofustis stercorihominis.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Anaerostipes hadrus.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Anaerotruncus colihominis.*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Clostridium sporogenes*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Clostridium tetani*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Coprococcus*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Coprococcus eutactus*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Eubacterium cylindroides*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Eubacterium dolichum*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Eubacterium ventriosum*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Roseburia faeccis*

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Roseburia hominis*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Roseburia intestinalis*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from a vinegar-producing microbe.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Lactobacillus bifidus*.

A composition can comprise a therapeutically-effective amount of an isolated and/or purified microbe with a rRNA (e.g., 16S rRNA, 23S rRNA, and/or internal transcribed spacer) sequence comprising at least about: 85%, 87%, 90%, 92%, 95%, 96%, 97%, 98%, 99%, 99.5%, or 100% sequence identity to a rRNA sequence from *Lactobacillus johnsonii*

A composition can comprise a microbe encoding a butyrate kinase enzyme (e.g., EC 2.7.2.7; MetaCyc Reaction ID R11-RXN). Butyrate kinase is an enzyme belonging to a family of transferases, for example those transferring phosphorus-containing groups (e.g., phosphotransferases) with a carboxy group as acceptor. The systematic name of this enzyme class can be ATP: butanoate 1-phosphotransferase. Butyrate kinase can participate in butyrate metabolism. Butyrate kinase can catalyze the following reaction:

$$\text{ADP+butyryl-phosphate} \rightleftharpoons \text{ATP+butyrate}$$

A composition of the disclosure can comprise a microbe with a butyrate-Coenzyme A. Butyrate-Coenzyme A, also butyryl-coenzyme A, can be a coenzyme A-activated form of butyric acid. It can be acted upon by butyryl-CoA dehydrogenase and can be an intermediary compound in acetone-butanol-ethanol fermentation. Butyrate-Coenzyme A can be involved in butyrate metabolism.

A composition of the disclosure can comprise a microbe encoding a butyrate-Coenzyme A transferase enzyme. Butyrate-Coenzyme A transferase, also known as butyrate-acetoacetate CoA-transferase, can belong to a family of transferases, for example, the CoA-transferases. The systematic name of this enzyme class can be butanoyl-CoA: acetoacetate CoA-transferase. Other names in common use can include butyryl coenzyme A-acetoacetate coenzyme A-transferase (e.g., EC 2.8.3.9; MetaCyc Reaction ID 2.8.3.9-RXN), and butyryl-CoA-acetoacetate CoA-transferase. Butyrate-Coenzyme A transferase can catalyze the following chemical reaction:

$$\text{butanoyl-CoA+acetoacetate} \rightleftharpoons \text{butanoate+acetoacetyl-CoA}$$

A composition of the disclosure can comprise a microbe encoding an acetate Coenzyme A transferase (e.g., EC 2.8.3.1/2.8.3.8; MetaCyc Reaction ID BUTYRATE-KINASE-RXN).

A composition of the disclosure can comprise a microbe encoding a Butyryl-Coenzyme A dehydrogenase. Butyryl-CoA dehydrogenase can belong to the family of oxidoreductases, for example, those acting on the CH—CH group of donor with other acceptors. The systematic name of this enzyme class can be butanoyl-CoA: acceptor 2,3-oxidoreductase. Other names in common use can include butyryl dehydrogenase, unsaturated acyl-CoA reductase, ethylene reductase, enoyl-coenzyme A reductase, unsaturated acyl coenzyme A reductase, butyryl coenzyme A dehydrogenase, short-chain acyl CoA dehydrogenase, short-chain acyl-coenzyme A dehydrogenase, 3-hydroxyacyl CoA reductase, and butanoyl-CoA: (acceptor) 2,3-oxidoreductase. Non-limiting examples of metabolic pathways that butyryl-CoA dehydrogenase can participate in include: fatty acid metabolism; valine, leucine and isoleucine degradation; and butanoate metabolism. Butyryl-CoA dehydrogenase can employ one cofactor, FAD. Butyryl-CoA dehydrogenase can catalyze the following reaction:

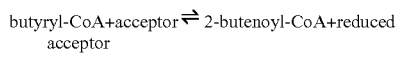

A composition of the disclosure can comprise a microbe encoding a beta-hydroxybutyryl-CoA dehydrogenase. Beta-hydroxybutyryl-CoA dehydrogenase or 3-hydroxybutyryl-CoA dehydrogenase can belong to a family of oxidoreductases, for example, those acting on the CH—OH group of donor with NAD+ or NADP+ as acceptor. The systematic name of the enzyme class can be (S)-3-hydroxybutanoyl-CoA:NADP+ oxidoreductase. Other names in common use can include beta-hydroxybutyryl coenzyme A dehydrogenase, L(+)-3-hydroxybutyryl-CoA dehydrogenase, BHBD, dehydrogenase, L-3-hydroxybutyryl coenzyme A (nicotinamide adenine, dinucleotide phosphate), L-(+)-3-hydroxybutyryl-CoA dehydrogenase, and 3-hydroxybutyryl-CoA dehydrogenase. Beta-hydroxybutyryl-CoA dehydrogenase enzyme can participate in benzoate degradation via co-ligation. Beta-hydroxybutyryl-CoA dehydrogenase enzyme can participate in butanoate metabolism. Beta-hydroxybutyryl-CoA dehydrogenase can catalyze the following reaction:

A composition of the disclosure can comprise a microbe encoding a crotonase. Crotonase can comprise enzymes with, for example, dehalogenase, hydratase, isomerase activities. Crotonase can be implicated in carbon-carbon bond formation, cleavage, and hydrolysis of thioesters. Enzymes in the crotonase superfamily can include, for example, enoyl-CoA hydratase which can catalyse the hydratation of 2-trans-enoyl-CoA into 3-hydroxyacyl-CoA; 3-2trans-enoyl-CoA isomerase or dodecenoyl-CoA isomerise (e.g., EC 5.3.3.8), which can shift the 3-double bond of the intermediates of unsaturated fatty acid oxidation to the 2-trans position; 3-hydroxbutyryl-CoA dehydratase (e.g., crotonase; EC 4.2.1.55), which can be involved in the butyrate/butanol-producing pathway; 4-Chlorobenzoyl-CoA dehalogenase (e.g., EC 3.8.1.6) which can catalyze the conversion of 4-chlorobenzoate-CoA to 4-hydroxybenzoate-CoA; dienoyl-CoA isomerase, which can catalyze the isomerisation of 3-trans,5-cis-dienoyl-CoA to 2-trans,4-trans-dienoyl-CoA; naphthoate synthase (e.g., MenB, or DHNA synthetase; EC 4.1.3.36), which can be involved in the biosynthesis of menaquinone (e.g., vitamin K2); carnitine racemase (e.g., gene caiD), which can catalyze the reversible conversion of crotonobetaine to L-carnitine in *Escherichia coli*; Methylmalonyl CoA decarboxylase (e.g., MMCD; EC 4.1.1.41); carboxymethylproline synthase (e.g., CarB), which can be involved in carbapenem biosynthesis; 6-oxo camphor hydrolase, which can catalyze the desymmetrization of bicyclic beta-diketones to optically active keto acids; the alpha subunit of fatty acid oxidation complex, a multienzyme complex that can catalyze the last three reactions in the fatty acid beta-oxidation cycle; and AUH protein, which can be a bifunctional RNA-binding homologue of enoyl-CoA hydratase.

A composition of the disclosure can comprise a microbe encoding a thiolase. Thiolases, also known as acetyl-coenzyme A acetyltransferases (ACAT), can convert two units of acetyl-CoA to acetoacetyl COA, for example, in the mevalonate pathway. Thiolases can include, for example, degradative thiolases (e.g., EC 2.3.1.16) and biosynthetic thiolases (e.g., EC 2.3.1.9). 3-ketoacyl-CoA thiolase, also called thiolase I, can be involved in degradative pathways such as fatty acid beta-oxidation. Acetoacetyl-CoA thiolase, also called thiolase II, can be specific for the thiolysis of acetoacetyl-CoA and can be involved in biosynthetic pathways such as poly beta-hydroxybutyric acid synthesis or steroid biogenesis. A thiolase can catalyze the following reaction:

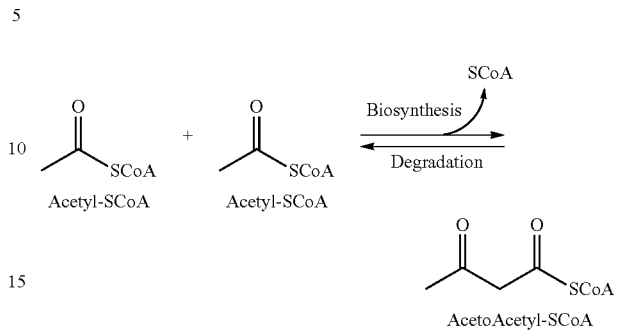

A composition of the disclosure can comprise one or more obligate anaerobes. A microbe can be an obligate anaerobe that is oxygen stable.

A microbe of the disclosure, such as an oxygen stable microbe, can be stable under atmospheric conditions, for example, atmosphere containing at least about 10%, 11%, 12%, 13%, 14%, 15%, 16%, 17%, 18%, 19%, 20%, 21%, 22%, 23%, 24%, or 25% oxygen. The stability and viability of the microbes may be monitored for at least about 7 days, 14 days, 28 days, 30 days, 60 days, 84 days, 90 days, 120 days, 150 days, 180 days, 192 days, 365 days, or 730 days. The microbes may be stable at a temperature of at least about 0° C., 5° C., 10° C., 15° C., 20° C., 25° C., or 30° C. . . . One or more oxygen stable microbes can be viable from 0 parts per million (ppm) of oxygen to 100 ppm of oxygen. Oxygen stable microbes may be viable in at most 0.1 ppm, 0.2 ppm, 0.3 ppm, 0.4 ppm, 0.5 ppm, 0.6 ppm, 0.7 ppm, 0.8 ppm, 0.9 ppm, 1 ppm, 1.2 ppm, 1.4 ppm, 1.6 ppm, 1.8 ppm, 2 ppm, 2.2 ppm, 2.4 ppm, 2.6 ppm, 2.8 ppm, 3 ppm, 3.2 ppm, 3.4 ppm, 3.6 ppm, 3.8 ppm, 4 ppm, 4.2 ppm, 4.4 ppm, 4.6 ppm, 4.8 ppm, 5 ppm, 10 ppm, or 100 ppm of oxygen. Oxygen stable microbes may be viable in 0%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% of dissolved oxygen (DO).

A composition can comprise more than one microbial population. For example, a composition can comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, or at least 50, or at least 75, or at least 100 different microbial populations (e.g, strains, species, phyla, classes, orders, families, or genus). A composition can comprise at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, at most 20, at most 21, at most 22, at most 23, at most 24, at most 25, at most 26, at most 27, at most 28, at most 29, at most 30, at most 31, at most 32, at most 33, at most 34, at most 35, at most 36, at most 37, at most 38, at most 39, at most 40, at most 45, or at most 50, or at most 75, or at most 100 different microbial populations (e.g., strains, species, phyla, classes, orders, families, or genus).

A composition can comprise a synergistic population of microbes. Combining different microbes in a composition can increase or help maintain the stability of the microbes in the composition compared with the stability of the microbes alone. For example, administration of a first microbe may be beneficial to a subject and administration of a second microbe may be beneficial to a subject but when the two microbes are administered together to a subject, the benefit is greater than the either benefit alone.

Microbes in a composition can be present in the same amount or in different amounts. For example, the ratio of two microbes in a composition can be about 1.5:1, 1:1, 1:1.5, 1:2, 1:3, 1:4, 1:5, 1:10, 1:25, 1:50, 1:100, 1:1000, 1:10,000, or 1:100,000.

Compositions and methods of the disclosure can be used to treat a disorder. The disorder can be a microbiome-associated disorder. The disorder can be a comorbidity associated with a dysbiosis (e.g., gut dysbiosis).

The disorder can be associated with or caused by an altered production of a short-chain fatty acid (SCFA). SCFAs can be a subgroup of fatty acids with 6 or less carbons in their aliphatic tails. Non-limiting examples of SCFAs include acetate, propionate, isobutyrate, isovaleric acid, 3-methylbutanoic acid, valeric acid, pentanoic acid, delphinic acid, isopentanoic acid, and butyrate. Altered SCFA production can be caused by, for example, an alteration of a microbiome of the subject such as a reduced SCFA-producing microbial population in the gut, altered SCFA-production pathway, alteration of a substrate, cofactor, or prebiotic needed for SCFA production, or any combination thereof. Alterations in the relative abundance of SCFAs relative to each other can lead to a disorder. For example, an altered fiber to acetate production pathway or an altered acetate to butyrate production pathway can lead to a disorder.

A disorder can be associated with a reduced production of butyrate in a subject. Butyrate can be produced by butyrate-producing microbes in the gut using, for example, dietary fiber. Butyrate production in the gut can involve a combination of microbes, for example, a first microbe producing a butyrate-intermediate (e.g., acetate or lactate) and a second microbe converting the butyrate-intermediate to butyrate. Butyrate can be absorbed by intestinal cells and initiate G-protein coupled receptor (GPCR) signaling, leading to glucagon-like peptide-1 (GLP-1) secretion. Due to their central role, SCFAs such as butyrate can be implicated in numerous body functions. For example, reduce inflammation, regulate gut permeability, improve glucose control, improve insulin insensitivity, immune system regulation, promote satiety, reduce dietary intake, activation of free fatty acid receptors, leptin production, regulation (e.g., inhibit) of NF-kappa B pathway, improve ion retention, and improve resilience of the gut to pathogenic bacteria and their toxins, and modulation of gut-brain axis.

A disorder can be a metabolic or gastrointestinal disorder. Non-limiting examples of metabolic disorders include prediabetes, insulin resistance, diabetes, Type I diabetes mellitus, Type II diabetes mellitus, gestational diabetes, juvenile diabetes, metabolic syndrome, inflammatory bowel disease (IBD), irritable bowel syndrome (IBS), obesity, overweight condition, ischemia-reperfusion injury such as hepatic ischemia-reperfusion injury, fatty liver disease, non-alcoholic fatty liver disease (NAFLD), alcoholic steatohepatitis (ASH), non-alcoholic steatohepatitis (NASH), NAFLD in a non-obese subject (e.g., NAFLD not caused by or related to obesity or excess weight problems), NASH in a non-obese subject (e.g., NASH not caused or related to obesity or excess weight problems), Crohn's disease, colitis, ulcerative colitis, pseudomembranous colitis, renal dysfunction, nephrological pathology, glomerular disease, lactose intolerance, insulin insensitivity, insulin deficiency, insulin resistance, glucose intolerance, diarrhea, allergic diarrhea, dextran sodium sulfate-induced colitis, celiac disease, and gastroparesis. In some cases, the disorder can be type I diabetes. In some cases, the disorder can be type 2 diabetes. In some cases, the disorder can be prediabetes. In some cases, the disorder can be irritable bowel syndrome (IBS). In some cases, the disorder can be diarrhea.

A disorder can be a neurological or behavioral disorder. Non-limiting examples or neurological disorders include neural activity disorders, anxiety, depression, food addiction, chronic fatigue syndrome, autism, autistic spectrum disorder, Asperger syndrome, Pervasive Developmental Disorder, Parkinson's disease, Alzheimer's disease, dementia, amyotrophic lateral sclerosis (ALS), bulbar palsy, pseudobulbar palsy, primary lateral sclerosis, motor neuron dysfunction (MND), mild cognitive impairment (MCI), Huntington's disease, ocular diseases, age-related macular degeneration, glaucoma, vision loss, presbyopia, cataracts, progressive muscular atrophy, lower motor neuron disease, spinal muscular atrophy (SMA), Werdnig-Hoffman Disease (SMA1), SMA2, Kugelberg-Welander Disease (SM3), Kennedy's disease, post-polio syndrome, and hereditary spastic paraplegia. Methods and compositions of the disclosure can be used, for example, for stabilizing mood, improving mood, modulating excessive emotional distress, reducing anxiety, reducing stress, and combinations thereof. In some cases, the disorder can be autism. In some cases, the disorder can be depression.

A disorder can be an immunological disorder or an immune system-associated condition. Non-limiting examples of immune system-related conditions include allergies, inflammation, inflammatory disorder, anaphylactic shock, autoimmune diseases, rheumatoid arthritis, systemic lupus erythematosus (SLE), scleroderma, diabetes, Autoimmune enteropathy, Coeliac (celiac) disease, Crohn's disease, Microscopic colitis, ulcerative colitis, osteoarthritis, osteoporosis, oral mucositis, inflammatory bowel disease, kyphosis, herniated intervertebral disc, ulcerative asthma, renal fibrosis, liver fibrosis, pancreatic fibrosis, cardiac fibrosis, skin wound healing, and oral submucous fibrosis. In some cases, the disorder can be inflammation.

A disorder can be a skin or dermatological disorder. Non-limiting examples of such disorders include skin health conditions, acne, psoriasis, eczema, rashes, rhytides, pruritis, dysesthesia, papulosquamous disorders, erythroderma, lichen planus, lichenoid dermatosis, atopic dermatitis, eczematous eruptions, eosinophilic dermatosis, reactive neutrophilic dermatosis, pemphigus, pemphigoid, immunobullous dermatosis, fibrohistocytic proliferations of skin, cutaneous lymphomas, and cutaneous lupus. In some cases, the disorder can be eczema. In some cases, the disorder can be rashes.

A disorder can be a cardiovascular condition. Non-limiting examples of cardiovascular conditions include angina, arrhythmia, atherosclerosis, cardiomyopathy, congestive heart failure, coronary artery disease (CAD), carotid artery disease, endocarditis, heart attack, coronary thrombosis, myocardial infarction (MI), high blood pressure/hypertension, aortic aneurysm, brain aneurysm, cardiac fibrosis, cardiac diastolic dysfunction, hypercholesterolemia/hyperlipidemia, heart disease, mitral valve prolapse, peripheral vascular disease, peripheral artery disease (PAD), cardiac stress resistance, stroke, disorders associated with cholesterol, and disorders associated with elevated triglycerides.

A disorder can be a pulmonary disorder. Non-limiting examples of pulmonary conditions include idiopathic pulmonary fibrosis (IPF), chronic obstructive pulmonary disease (COPD), asthma, cystic fibrosis, bronchiectasis, and emphysema.

A disorder can be a connective tissue disorder. Non-limiting examples of connective tissue disorders include rheumatoid arthritis, systemic lupus erythematosus, scleroderma, sarcoidosis, and Wegener's granulomatosis.

A disorder can be cancer. Non-limiting examples of cancers include colorectal cancer, acute lymphoblastic leukemia, acute myeloid leukemia, adrenocortical carcinoma, AIDS-related cancers, AIDS-related lymphoma, anal cancer, appendix cancer, astrocytomas, neuroblastoma, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, Wilms tumor, and metastasis.

A disorder can be a vaginal disorder. Non-limiting examples of vaginal conditions include vaginosis, bacterial vaginosis, viral vaginosis, vulvovaginitis, yeast infection, preterm labor, fertility-associated conditions (e.g., low fertility), *Trichomonas*, Vulvodynia douche follow-up treatment, vulvar vestibulitis, vulvodynia, vaginal douching. Compositions of the disclosure can be used after douching (e.g., after douching in subject with vulvodynia).

A disorder can be a dental disorder. Non-limiting examples of dental disorders include dental cavities and halitosis.

A disorder can be a pregnancy-associated condition. Non-limiting examples of pregnancy-associated conditions include preterm delivery, preterm labor, obesity during pregnancy, or gestational diabetes. Compositions of the disclosure can be administered to a pregnant woman carrying an infant to be born via C-section and/or to an infant born via C-section. Compositions of the disclosure can be administered to infants, pregnant women, or both for decreasing occurrence of intestinal pathogens or any of the disorders described herein in those infants or mothers. The infant can be an infant delivered via a caesarean section. The infant can be a formula-feeding infant.

A disorder can be a sleep disorder, multiple sclerosis, infections such as *Clostridium difficile* infection, genitourinary disorders, oral thrush, diabetic foot ulcers, bacteremia, infantile colic, urinary tract infection, radiation enteropathy, appendicitis, atopic disease, ageing, age-related disorder, premature aging disorder, a chemotherapy or radiotherapy-induced condition, fasting-related condition, metastasis, or a condition associated with drug metabolism. A composition of the disclosure can be administered after an antibiotic treatment (e.g., in kids). A composition of the disclosure can be administered to subjects that have undergone bariatric surgery (e.g., post-bariatric surgery). A composition of the disclosure can be administered as an antibody/immunotherapy companion. A composition of the disclosure can be administered for treating comorbidities of any of the disorders described herein.

A composition can comprise a prebiotic. A prebiotic can affect the growth or activity of microorganisms in a host. Prebiotics can be selectively fermented, e.g. in the colon. A prebiotic can serve as an energy source for a microbe. Non-limiting examples of prebiotics include complex carbohydrates, complex sugars, resistant dextrins, resistant starch, amino acids, peptides, nutritional compounds, biotin, polydextrose, oligosaccharides, polysaccharide, fructooligosaccharide (FOS), fructans, soluble fiber, insoluble fiber, fiber, starch, galactooligosaccharides (GOS), inulin, lignin, psyllium, chitin, chitosan, gums (e.g. guar gum), high amylose cornstarch (HAS), cellulose, β-glucans, hemi-celluloses, lactulose, mannooligosaccharides, mannan oligosaccharides (MOS), oligofructose-enriched inulin, oligofructose, oligodextrose, tagatose, trans-galactooligosaccharide, pectin, resistant starch, xylooligosaccharides (XOS), locust bean gum, P-glucan, and methylcellulose.

A prebiotic and microbe combination can be formulated to create an entirely self-sufficient system that does not require any external input. Such a combination can provide a complete system for producing amino acids, polyphenols, vitamins, and other compounds of nutritive value in a subject. A subject can be treated with a combination of SCFA-producing microbes and prebiotics comprising dietary fiber and other agents required for the activity of the SCFA-producing microbes. In this manner, the prebiotic and microbes form a self-sufficient system, wherein the microbe converts the prebiotic dietary fiber to SCFAs (e.g., butyrate, acetate, propionate), which can trigger downstream signaling for treating a disorder.

Compositions and methods of the disclosure can increase engraftment of a microbe in a subject. Engraftment can be indicated by an increased relative abundance of a microbe in the subject. In an illustrative method, engraftment of a microbe in a subject can be determined by measuring a relative amount of a nucleic acid of the microbe to be engrafted in a biological sample obtained from the subject (e.g., a stool sample for assessing gut microbiome) before administration (e.g., baseline sample) and post-administration (e.g., washout period sample) of the microbe. Engraftment of the administered microbe can result in an increase in the amount of nucleic acid of the microbe in the washout sample relative to the baseline sample or a control. The amount of nucleic acid can be determined using sequencing or qPCR. Target specific primers to a microbe can be used for assaying engraftment.

In another illustrative method, engraftment of a microbe in a subject can be determined by measuring a relative amount of a nucleic acid of the microbe in a biological sample (e.g., a stool sample for assessing gut microbiome) obtained from one subject or group of subjects relative to a second subject or group of subjects. The first subject or group of subjects can have been administered composition of the disclosure (e.g., comprising at least one mucin-degrading microbe and at least one butyrate-producing microbe). The second subject or group of subjects can have been administered a placebo, an alternative composition of the disclosure, or a control composition (e.g., a composition comprising butyrate-producing microbes but no mucin-degrading microbes). The biological samples can be obtained, for example, during administration of the compositions, or after a washout period. Engraftment of the administered microbe can result in an increase in the amount of nucleic acid of the microbe in the first subject or group of subjects relative to the second subject or group of subjects. The amount of nucleic acid can be determined using sequencing or qPCR. Target specific primers to a microbe can be used for assaying engraftment.

Compositions and methods of the disclosure can increase engraftment of a microbe (e.g., as determined by measuring nucleic acid of the microbe) in a subject by at least about 1-fold, 2-fold, 3-fold, 4-fold, 5-fold, 10 fold, 15 fold, 20 fold, 30 fold, 40 fold, 50 fold, 60 fold, 70 fold, 80 fold, 90 fold, 100 fold, or more, relative to a control (e.g., baseline or pre-treatment).

Compositions and methods of the disclosure can increase engraftment of a microbe in a subject by at least about 1%, 2%, 3%, 4%, 5%, 10%, 15%, 20%, 25%, 30%, 35%, 40 45%, 50%, 60%, 70%, 80%, 90%, 91%, 92%, 93%, 94%, 95%, 96%, 97%, 98%, 99% or 100% relative to a control (e.g., baseline or pre-treatment). Compositions and methods of the disclosure can increase engraftment of a microbe in a subject by about 1%, 2%, 3%, 4%, 5%, 10%, 15%, 20%, 25%, 30%, 35%, 40 45%, 50%, 60%, 70%, 80%, 90%, 91%, 92%, 93%, 94%, 95%, 96%, 97%, 98%, 99% or 100% relative to a control (e.g., baseline or pre-treatment).

Compositions and methods of the disclosure can increase SCFA production in a subject by at least about 1%, 2%, 3%, 4%, 5%, 10%, 15%, 20%, 25%, 30%, 35%, 40 45%, 50%, 60%, 70%, 80%, 90%, or 95% relative to a control (e.g., baseline or pre-treatment). Compositions and methods of the disclosure can increase SCFA production in a subject by about 1%, 2%, 3%, 4%, 5%, 10%, 15%, 20%, 25%, 30%, 35%, 40 45%, 50%, 60%, 70%, 80%, 90%, or 95% relative to a control (e.g., baseline or pre-treatment).

Compositions and methods of the disclosure can increase butyrate production in a subject by at least about 1%, 2%, 3%, 4%, 5%, 10%, 15%, 20%, 25%, 30%, 35%, 40 45%, 50%, 60%, 70%, 80%, 90%, or 95% relative to a control (e.g., baseline or pre-treatment). Compositions and methods of the disclosure can increase butyrate production in a subject by about 1%, 2%, 3%, 4%, 5%, 10%, 15%, 20%, 25%, 30%, 35%, 40 45%, 50%, 60%, 70%, 80%, 90%, or 95% relative to a control (e.g., baseline or pre-treatment).

A control sample can refer to a baseline sample such as a sample collected prior to administration of the composition. A control can refer to a microbial composition lacking a microbe that enhances engraftment of other microbes. A control can refer to a placebo sample.

Microbial compositions described herein can be used to create a pharmaceutical composition comprising a therapeutically-effective amount of the composition for treating a subject. A pharmaceutical composition of the disclosure can be a combination of any microorganisms described herein with other components, such as carriers, stabilizers, diluents, dispersing agents, suspending agents, thickening agents, and excipients. The pharmaceutical composition can facilitate administration of the microorganisms to a subject. The appropriate quantity of a therapeutic composition to be administered, the number of treatments, and unit dose can vary according to a subject and/or the disease state of the subject. A composition can be administered as a therapeutic or cosmetic.

Compositions of the disclosure can comprise isolated and purified microbes formulated in a substantially dry powder form. The isolated and purified microbes can be derived from lyophilization of microbial cultures. A lyophilized composition can be mixed with a saline or other solution prior to administration.

A composition can comprise viable microbes. For example, the microbial composition comprises microbes that can replicate once they are delivered to the target habitat (e.g. gut). In some cases, the composition may not comprise spores.

A composition can have a shelf life of at least about: 1, 2, 3, 4, 5, 6, 7, 8, 9, 10, 11, or 12 months. A composition comprising obligate anaerobic microbes may be formulated to reduce or eliminate the exposure to oxygen in order to increase shelf-life.

A composition disclosed herein may be formulated as a food or beverage product, cosmetic, or nutritional supplement. Microbial compositions can be formulated as a dietary supplement. Microbial compositions can be incorporated with vitamin supplements. Microbial compositions can be formulated in a chewable form such as a probiotic gummy. Microbial compositions can be incorporated into a form of food and/or drink. Non-limiting examples of food and drinks where the microbial compositions can be incorporated include, for example, bars, shakes, juices, infant formula, beverages, frozen food products, fermented food products, and cultured dairy products such as yogurt, yogurt drink, cheese, *acidophilus* drinks, and kefir.

A composition can be formulated for release to a suitable part of the gastrointestinal tract of a subject. Non-limiting examples of gastrointestinal tract regions include duodenum, small intestine regions including duodenum, jejunum, ileum, and large intestine regions including cecum, colon, ascending colon, transverse colon, descending colon, sigmoid colon, rectum, and anal canal. The composition can be formulated for delivery to the ileum or colon regions of the gastrointestinal tract.

A composition can be formulated for delivery by any suitable delivery method. Non-limiting examples of delivery routes include topical, oral, parenteral, rectal, mucosal, vaginal, and enteral/gastrointestinal. A combination of administration routes can be utilized.

A composition can be administered orally, for example, through a capsule, pill, powder, tablet, gel, or liquid, designed to release the composition in the gastrointestinal tract.

In one non-limiting example, the microbial composition can be formulated for oral administration for example, in a pill or a capsule. The composition can comprise an enteric coating, for example, to prevent release of the contents in the stomach of the subject. The composition can be designed for a substantial release the composition contents in a gastrointestinal region of the subject (e.g., upper colon; ileum, colon region).

An enteric-coating can protect the contents of a composition, for example, oral composition such as pill or capsule, from the acidity of the stomach. An enteric-coating can provide delivery to the ileum and/or upper colon regions. A microbial composition can be formulated such that the contents of the composition may not be released in a body part other than the gut region, for example, ileum and/or colon region of the subject. Non-limiting examples of enteric coatings include pH sensitive polymers (e.g., eudragit FS30D), methyl acrylate-methacrylic acid copolymers, cellulose acetate succinate, hydroxy propyl methyl cellulose phthalate, hydroxy propyl methyl cellulose acetate succinate (e.g., hypromellose acetate succinate), polyvinyl acetate phthalate (PVAP), methyl methacrylate-methacrylic acid copolymers, shellac, cellulose acetate trimellitate, sodium alginate, zein, other polymers, fatty acids, waxes, shellac, plastics, and plant fibers. The enteric coating can be formed by a pH sensitive polymer. The enteric coating can be formed by eudragit FS30D.

The enteric coating can be designed to dissolve at any suitable pH. The enteric coating can be designed to dissolve at a pH greater than from about pH 6.5 to about pH 7.0. The enteric coating can be designed to dissolve at a pH greater than about pH 6.5. The enteric coating can be designed to dissolve at a pH greater than about pH 7.0. The enteric coating can be designed to dissolve at a pH greater than about: 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, or 8 pH units. The enteric coating can be designed to dissolve in the gut, for example, ileum and/or colon region. The enteric coating can be designed to not dissolve in the stomach.

A composition can be administered topically. The compositions can be formulated as a topically administrable composition, such as solutions, suspensions, lotions, gels, pastes, medicated sticks, balms, creams, ointments, liquid, wrap, adhesive, or patch. The compositions can contain solubilizers, stabilizers, tonicity enhancing agents, buffers and preservatives.

A composition can be administered by injection, for example, for a composition comprising, for example, butyrate, propionate, acetate, and short-chain fatty acids. A composition can be administered using a suppository or by enema. A combination of administration routes can be utilized.

A composition of the disclosure can be administered as part of a fecal transplant process. A composition can be administered to a subject by a tube, for example, nasogastric tube, nasojejunal tube, nasoduodenal tube, oral gastric tube, oral jejunal tube, or oral duodenal tube. A composition can be administered to a subject by colonoscopy, endoscopy, sigmoidoscopy, and/or enema.

A composition can comprise metabolites, bacteriocins, enzymes, anti-microbial peptides, antibiotics, prebiotics, probiotics, glycans, bacteriophages, and any combination thereof. A composition can comprise: inulin, sucrose, trehalose, glycerin, maltodextrin, hydroxypropyl methylcellulose, or a combination thereof. The compositions can include metabolites for example, to assist in the initial efficacy of the therapeutic before the microbes can produce their own metabolites. Metabolites can include short-chain fatty acids, which can be a subgroup of fatty acids with 6 or less carbons in their aliphatic tails, for example, acetate, propionate, isobutyrate, isovaleric acid, 3-methylbutanoic acid, valeric acid, pentanoic acid, delphinic acid, isopentanoic acid, and butyrate.

The composition can be stored in cold storage, for example, at a temperature of about −80° C., about −20° C., about −4° C., or about 4° C. Compositions provided herein can be stored at any suitable temperature. The storage temperature can be, for example, about 0° C., about 1° C., about 2° C., about 3° C., about 4° C., about 5° C., about 6° C., about 7° C., about 8° C., about 9° C., about 10° C., about 12° C., about 14° C., about 16° C., about 20° C., about 22° C., or about 25° C. The storage temperature can be between about 2° C. to about 8° C. Storage of microbial compositions at low temperatures, for example from about 2° C. to about 8° C., can keep the microbes alive and increase the efficiency of the composition. The cooling conditions can also provide soothing relief to patients. Storage at freezing temperature, below 0° C., with a cryoprotectant can further extend stability.

A composition of the disclosure can be at any suitable pH. The pH of the composition can range from about 3 to about 12. The pH of the composition can be, for example, from about 3 to about 4, from about 4 to about 5, from about 5 to about 6, from about 6 to about 7, from about 7 to about 8, from about 8 to about 9, from about 9 to about 10, from about 10 to about 11, or from about 11 to about 12 pH units. The pH of the composition can be, for example, about 3, about 4, about 5, about 6, about 7, about 8, about 9, about 10, about 11, or about 12 pH units. The pH of the composition can be, for example, at least 3, at least 4, at least 5, at least 6, at least 7, at least 8, at least 9, at least 10, at least 11 or at least 12 pH units. The pH of the composition can be, for example, at most 3, at most 4, at most 5, at most 6, at most 7, at most 8, at most 9, at most 10, at most 11, or at most 12 pH units. The pH of the composition can be, for example, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0 pH units. If the pH is outside the range desired by the formulator, the pH can be adjusted by using sufficient pharmaceutically-acceptable acids and bases. The pH of the composition can be from about 4 to about 6 pH units. The pH of the composition can be about 5.5 pH units.

Administration of a composition of the disclosure can be preceded by, for example, colon cleansing methods such as colon irrigation/hydrotherapy, enema, administration of laxatives, dietary supplements, dietary fiber, enzymes, and magnesium.

Microbes of the disclosure can be formulated as a population of spores. Spore-containing compositions can be administered by any suitable route described herein. Orally administered spore-containing compositions can survive the low pH environment of the stomach. The amount of spores employed can be, for example, from about 1% w/w to about 99% w/w of the entire composition. In some cases, a microbial composition does not comprise spores.

Compositions provided herein can include the addition of one or more agents to the therapeutics or cosmetics in order to enhance stability and/or survival of the microbial composition. Non-limiting example of stabilizing agents include genetic elements, glycerin, ascorbic acid, skim milk, lactose, tween, alginate, xanthan gum, carrageenan gum, mannitol, palm oil, and poly-L-lysine (POPL).

A composition can comprise recombinant microbes or microbes that have been genetically modified. For example, the composition comprises microbes that can be regulated, such as a microbe comprising an operon to control microbial growth.

A composition can be customized for a subject. Data specific to the subject comprising for example age, gender, and weight can be combined with an analysis result to provide a therapeutic agent customized to the subject. For example, a subject's microbiome found to be low in a specific microbe relative to a sub-population of healthy subjects matched for age and gender can be provided with a therapeutic and/or cosmetic composition comprising the specific microbe to match that of the sub-population of healthy subjects having the same age and gender as the subject.

A composition can be administered after treatment with an antimicrobial agent such as an antibiotic. For example, the composition can be 12 hours, 1 day, 3 days, 1 week, 2 weeks, or 1 month after treatment with an antibiotic.

A composition can be administered before or after food intake by a subject. In an illustrative example, a composition is administered before food intake by a subject. For example, the composition can be more effective or potent when administered before food intake. For example, the composition can be administered about 10 minutes, about 15 minutes, about 30 minutes, about 45 minutes, about 1 hour, about 2 hours, about 3 hours, about 4 hours, about 5 hours, about 6 hours, about 7 hours, about 8 hours, about 9 hours, about 10 hours, about 12 hours, or about 1 day before food intake by a subject. For example, the composition can be administered at least about 5 minutes, about 10 minutes, about 15 minutes, about 30 minutes, about 45 minutes, about 1 hour, about 2 hours, about 3 hours, about 4 hours, about 5 hours, about 6 hours, about 7 hours, about 8 hours, about 9 hours, about 10 hours, about 12 hours, or about 1 day before food intake by a subject. For example, the composition can be administered at most about 10 minutes, about 15 minutes, about 30 minutes, about 45 minutes, about 1 hour, about 2 hours, about 3 hours, about 4 hours, about 5 hours, about 6 hours, about 7 hours, about 8 hours, about 9 hours, about 10 hours, about 12 hours, or about 1 day before food intake by a subject.

A composition can be administered after food intake by the subject. In some cases, the composition can be more effective or potent when administered after food intake. For example, the composition can be administered at least about 1 minute, 2 minutes, 3 minutes, 5 minutes, 10 minutes, 15 minutes, 30 minutes, 45 minutes, 1 hour, 2 hours, 3 hours, 5 hours, 10 hours, 12 hours, or 1 day after food intake by a subject. For example, the composition can be administered at most about 1 minute, 2 minutes, 3 minutes, 5 minutes, 10 minutes, 15 minutes, 30 minutes, 45 minutes, 1 hour, 2 hours, 3 hours, 5 hours, 10 hours, 12 hours, or 1 day after food intake by a subject.

A composition can include carriers and excipients (including but not limited to buffers, carbohydrates, lipids, mannitol, proteins, polypeptides or amino acids such as glycine, antioxidants, bacteriostats, chelating agents, suspending agents, thickening agents and/or preservatives), metals (e.g., iron, calcium), salts, vitamins, minerals, water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavouring agents, dispersion enhancer, disintegrant, coating agents, plasticizers, preservatives, suspending agents, emulsifying agents, plant cellulosic material and spheronization agents, and any combination thereof.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999), each of which is incorporated by reference in its entirety.

A composition can be substantially free of preservatives. In some applications, the composition may contain at least one preservative.

A composition can be substantially free of fecal matter.

A composition can be encapsulated within a suitable vehicle, for example, a liposome, a microspheres, or a microparticle. Microspheres formed of polymers or proteins can be tailored for passage through the gastrointestinal tract directly into the blood stream. Alternatively, the compound can be incorporated and the microspheres, or composite of microspheres, and implanted for slow release over a period of time ranging from days to months.

A composition can be formulated as a sterile solution or suspension. Therapeutic or cosmetic compositions can be sterilized by conventional techniques or may be sterile filtered. The resulting aqueous solutions may be packaged for use as is, or lyophilized. The lyophilized preparation of the microbial composition can be packaged in a suitable form for oral administration, for example, capsule or pill.

The compositions can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compositions can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as a mixture of fatty acid glycerides, optionally in combination with cocoa butter, can be used.

Microbial compositions can be formulated using one or more physiologically-acceptable carriers comprising excipients and auxiliaries, which facilitate processing of the microorganisms into preparations that can be used pharmaceutically. Compositions can be modified depending upon the route of administration chosen. Compositions described herein can be manufactured in a conventional manner, for example, by means of conventional mixing, dissolving, granulating, dragee-making, levigating, encapsulating, entrapping, emulsifying or compression processes.

Pharmaceutical compositions containing microbes described herein can be administered for prophylactic and/or therapeutic treatments. In therapeutic applications, the compositions can be administered to a subject already suffering from a disease or condition, in an amount sufficient to cure or at least partially arrest the symptoms of the disease or condition, or to cure, heal, improve, or ameliorate the condition. Microbial compositions can also be administered to lessen a likelihood of developing, contracting, or worsening a condition. Amounts effective for this use can vary based on the severity and course of the disease or condition, previous therapy, the subject's health status, weight, and response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills. The composition can be packed together or separately, in a single package or in a plurality of packages. One or all of the therapeutic agents can be given in multiple doses. If not simultaneous, the timing between the multiple doses may vary to as much as about a month.

Compositions described herein can be administered before, during, or after the occurrence of a disease or condition, and the timing of administering the composition can vary. For example, the microbial composition can be used as a prophylactic and can be administered continuously to subjects with a propensity to conditions or diseases in order to lessen a likelihood of the occurrence of the disease or condition. The microbial compositions can be administered to a subject during or as soon as possible after the onset of the symptoms. The administration of the microbial compositions can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any composition described herein. A microbial composition can be administered as soon as is practicable after the onset of a disease or condition is detected or suspected, and for a length of time necessary for the treatment of the disease, such as, for example, from about 1 month to about 3 months. The length of treatment can vary for each subject.

Compositions of the disclosure can be administered in combination with another therapy, for example, immunotherapy, chemotherapy, radiotherapy, anti-inflammatory agents, anti-viral agents, anti-microbial agents, and anti-fungal agents.

Compositions of the disclosure can be packaged as a kit. A kit can include written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. The label can be approved by a regulatory agency, for example the U.S. Food and Drug Administration (FDA), the European Medicines Agency (EMA), or other regulatory agencies.

A composition can be formulated for administration via pH-dependent release delivery, microbially-triggered delivery, time-controlled delivery, osmotically-regulated delivery, pressure-controlled delivery, multi matrix systems delivery, bio-adhesion delivery, or multiparticulate delivery. The composition can also be formulated for release in the small or large intestine, colon, rectum, stomach, anus, or esophagus.

A composition can be formulated for delayed delivery or slow delivery of the contents.

Pharmaceutical compositions described herein can be in unit dosage forms suitable for single administration of precise dosages. In unit dosage form, the composition can be divided into unit doses containing appropriate quantities of one or more microbial compositions. The unit dosage can be in the form of a package containing discrete quantities of the composition. Non-limiting examples are liquids in vials, ampoules, tablets, or capsules. Aqueous suspension compositions can be packaged in single-dose non-reclosable containers. The composition can be in a multi-dose format. Multiple-dose reclosable containers can be used, for example, in combination with a preservative. Compositions for parenteral injection can be presented in unit dosage form, for example, in ampoules, or in multi-dose containers with a preservative.

The dosage can be in the form of a solid, semi-solid, or liquid composition. Non-limiting examples of dosage forms suitable for use in the disclosure include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals, dietary supplement, and any combination thereof.

A microbe can be present in any suitable concentration in a pharmaceutical composition. The concentration of a microbe can be for example, from about $10^1$ to about $10^{18}$ colony forming units (CFU) or active cells/gram, used interchangeably herein. The concentration of a microbe can be, for example, about $10^1$, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$, about $10^{14}$, about $10^{15}$, about $10^{16}$, about $10^{17}$, or about $10^{18}$ CFU. The concentration of a microbe can be, for example, at least about $10^1$, at least about $10^2$, at least about $10^3$, at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, at least about $10^{16}$, at least about $10^{17}$, or at least about $10^{18}$ CFU. The concentration of a microbe can be, for example, at most about $10^1$, at most about $10^2$, at most about $10^3$, at most about $10^4$, at most about $10^5$, at most about $10^6$, at most about $10^7$, at most about $10^8$, at most about $10^9$, at most about $10^{10}$, at most about $10^{11}$, at most about $10^{12}$, at most about $10^{13}$, at most about $10^{14}$, at most about $10^{15}$, at most about $10^{16}$, at most about $10^{17}$, or at most about $10^{18}$ CFU. The concentration of a microbe can be from about $10^8$ CFU to about $10^9$ CFU. The concentration of a microbe can be about $10^8$ CFU. The concentration of a microbe can be about $10^9$ CFU. The concentration of a microbe can be about $10^{10}$ CFU. The concentration of a microbe can be at least about $10^8$ CFU. The concentration of a microbe can be at least about $10^9$ CFU.

The concentration of a microbe in a composition can be equivalent to, for example, about: 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 45, 50, 55, 60, 70, 80, 90, or 100 OD units. The concentration of a microbe in a composition can be equivalent to, for example, at least about: 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 45, 50, 55, 60, 70, 80, 90, or 100 OD units. The concentration of a microbe in a composition can be equivalent to, for example, at most about: 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 45, 50, 55, 60, 70, 80, 90, or 100 OD units.

Pharmaceutical compositions of the disclosure can be formulated with any suitable therapeutically-effective concentration of an active ingredient. For example, the therapeutically-effective concentration of a prebiotic can be at least about 1 mg/ml, about 2 mg/ml, about 3 mg/ml, about 4 mg/ml, about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 110 mg/ml, about 125 mg/ml, about 130 mg/ml, about 140 mg/ml, or about 150 mg/ml. For example, the therapeutically-effective concentration of a prebiotic can be at most about 1 mg/ml, about 2 mg/ml, about 3 mg/ml, about 4 mg/ml, about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 110 mg/ml, about 125 mg/ml, about 130 mg/ml, about 140 mg/ml, or about 150 mg/ml. For example, the therapeutically-effective concentration of a prebiotic can be about 1 mg/ml, about 2 mg/ml, about 3 mg/ml, about 4 mg/ml, about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 110 mg/ml, about 125 mg/ml, about 130 mg/ml, about 140 mg/ml, or about 150 mg/ml. The concentration of a prebiotic in a pharmaceutical composition can be about 70 mg/ml. The prebiotic can be inulin.

Compositions of the present disclosure can be formulated with any suitable therapeutically-effective concentration of an active ingredient in dry powder form. In some cases, the therapeutic composition comprises from about 50% to about 100% of the one or more prebiotics by dry weight. In some cases, the therapeutic composition comprises about 50%, 55%, 60%, 65%, 70%, 75%, 80%, 85%, 90%, 95%, 96%, 97%, 98%, 99%, or 100% of the one or more prebiotics by dry weight. In some cases, the prebiotic composition is a galactooligosaccharides (GOS) composition. In some cases, the GOS composition comprises disaccharides, trisaccharides, tetrasaccharides, and pentasaccharides. In some embodiments, the GOS composition comprises at least 80% disaccharides, trisaccharides, tetrasaccharides, and pentasaccharides by dry weight. In some cases, the GOS composition comprises from about 0.1% to about 5% disaccharides by dry weight, from about 30% to about 75% trisaccharides by dry weight, from about 15% to about 45% tetrasaccharides by dry weight, and from about 1% to about 20% pentasaccharides by dry weight. In some cases, the GOS composition comprises from about 1% to about 2% disaccharides by dry weight, from about 50% to about 60% trisaccharides by dry weight, about 25% to about 35% tetrasaccharides by dry weight, and about 5% to about 15% pentasaccharides by dry weight. In some cases, the GOS composition comprises from about 50% to about 100% GOS by dry weight. In some cases, the GOS composition comprises about 50%, 55%, 60%, 65%, 70%, 75%, 80%, 85%, 90%, 95%, 96%, 97%, 98%, 99%, or 100% GOS by dry weight. In some cases, the pharmaceutical composition comprises less than 10% digestible saccharides by dry weight. In some cases, the pharmaceutical composition comprises less than 5%, 4%, 3%, 2%, or 1% digestible saccharides by dry weight. In some cases, the prebiotic is inulin. In some cases, the therapeutic composition comprises from 1% to 50% inulin by dry weight. In some cases, the therapeutic composition comprises from 1% to 10%, from 10% to 20%, from 20% to 30%, from 30% to 40%, from 40% to 50% inulin by dry weight. In some cases, the therapeutic composition comprises from 50% to 100% inulin by dry weight. In some cases, the therapeutic composition comprises from 50% to 60%, from 60% to 70%, from 70% to 80%, from 80% to 90%, from 90% to 100% inulin by dry weight.

The course of treatment using the therapeutic compositions can vary. Pharmaceutical compositions of the disclosure can be administered, for example, 1, 2, 3, 4, 5, or more times daily. Pharmaceutical compositions of the disclosure can be administered, for example, daily, every other day, three times a week, twice a week, once a week, or at other appropriate intervals for treatment of the condition. Pharmaceutical compositions of the disclosure can be administered, for example, for 1, 2, 3, 4, 5, 6, 7, 10, 11, 12, 13, 14, 15, 20, 25, 30 or more days. Pharmaceutical compositions of the disclosure can be administered, for example, for 1, 2, 3, 4, 5, 6, 7, or more weeks. Pharmaceutical compositions of the disclosure can be administered, for example, for 1, 2, 3, 4, 5, 6, 7, or more months. Therapeutic compositions of the present disclosure can be administered for a period a time such that the one or more microbes in the composition engrafts in a subjects microbiome (e.g., as shown by presence in a stool sample after a washout period).

The time between a first administration and a second administration can vary. In some cases, the time between the first administration and the second administration can be about 30 minutes, 45 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In some cases, the time between the first administration and the second administration can be 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days. In some cases, the time between the first administration and the second administration can be 1 month, 2 months, 3 months, 4 months, 5 months, 6 months, 7 months, or more months.

An exemplary treatment plan can be treating a subject with a therapeutic composition at a first dose for at least 3 days, and then treating the subject with the therapeutic composition at a second dose for at least 3 days. In some treatment plans, a subject can be treated with a therapeutic composition at a first dose for at most 14 days, and then treating the subject with the therapeutic composition at a second dose for at most 14 days. In some treatment plans, a subject can be treated with a therapeutic composition at a first dose for from 7 to 14 days, and then treating the subject with the therapeutic composition at a second dose for from 7 to 14 days. In some treatment plans, a subject can be treated with a therapeutic composition at a first dose for 7 days, and then treating the subject with the therapeutic composition at a second dose for 7 days. In some treatment plans, the first dose and the second dose can be the same. In some treatment plans, the second dose can contain a microbe at an amount that is about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 30-fold, 40-fold, or 50-fold higher than the microbe amount of the first dose. In some treatment plans, the second dose contain a microbe at an amount that is at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 30-fold, at least 40-fold, or at least 50-fold higher than the microbe amount of the first dose. In some treatment plans, the second dose contain a microbe at an amount that is up to 2-fold, up to 3-fold, up to 4-fold, up to 5-fold, up to 6-fold, up to 7-fold, up to 8-fold, up to 9-fold, up to 10-fold, up to 11-fold, up to 12-fold, up to 13-fold, up to 14-fold, up to 15-fold, up to 16-fold, up to 17-fold, up to 18-fold, up to 19-fold, up to 20-fold, up to 30-fold, up to 40-fold, or up to 50-fold higher than the microbe amount of the first dose. In some treatment plans, the second dose can contain a microbe at an amount that is about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 30-fold, 40-fold, or 50-fold lower than the microbe amount of the first dose. In some treatment plans, the second dose contain a microbe at an amount that is at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 30-fold, at least 40-fold, or at least 50-fold lower than the microbe amount of the first dose. In some treatment plans, the second dose contain a microbe at an amount that is up to 2-fold, up to 3-fold, up to 4-fold, up to 5-fold, up to 6-fold, up to 7-fold, up to 8-fold, up to 9-fold, up to 10-fold, up to 11-fold, up to 12-fold, up to 13-fold, up to 14-fold, up to 15-fold, up to 16-fold, up to 17-fold, up to 18-fold, up to 19-fold, up to 20-fold, up to 30-fold, up to 40-fold, or up to 50-fold lower than the microbe amount of the first dose.

A composition can be substantially free of an allergen. Non-limiting examples of allergens include shellfish, crustaceans, peanuts, soy, wheat, milk or dairy, and gluten. In some cases, a composition can comprise milk.

Subjects can be, for example, mammal, humans, pregnant women, elderly adults, adults, adolescents, pre-adolescents, children, toddlers, infants, newborn, or neonates. A subject can be a patient. A subject can be a human. A subject can be a child (i.e. a young human being below the age of puberty). A subject can be an infant. A subject can be an individual enrolled in a clinical study. A subject can be a laboratory animal, for example, a mammal, or a rodent. A subject can be an obese or overweight subject. A subject can be a formula-fed infant.

Figure 9:
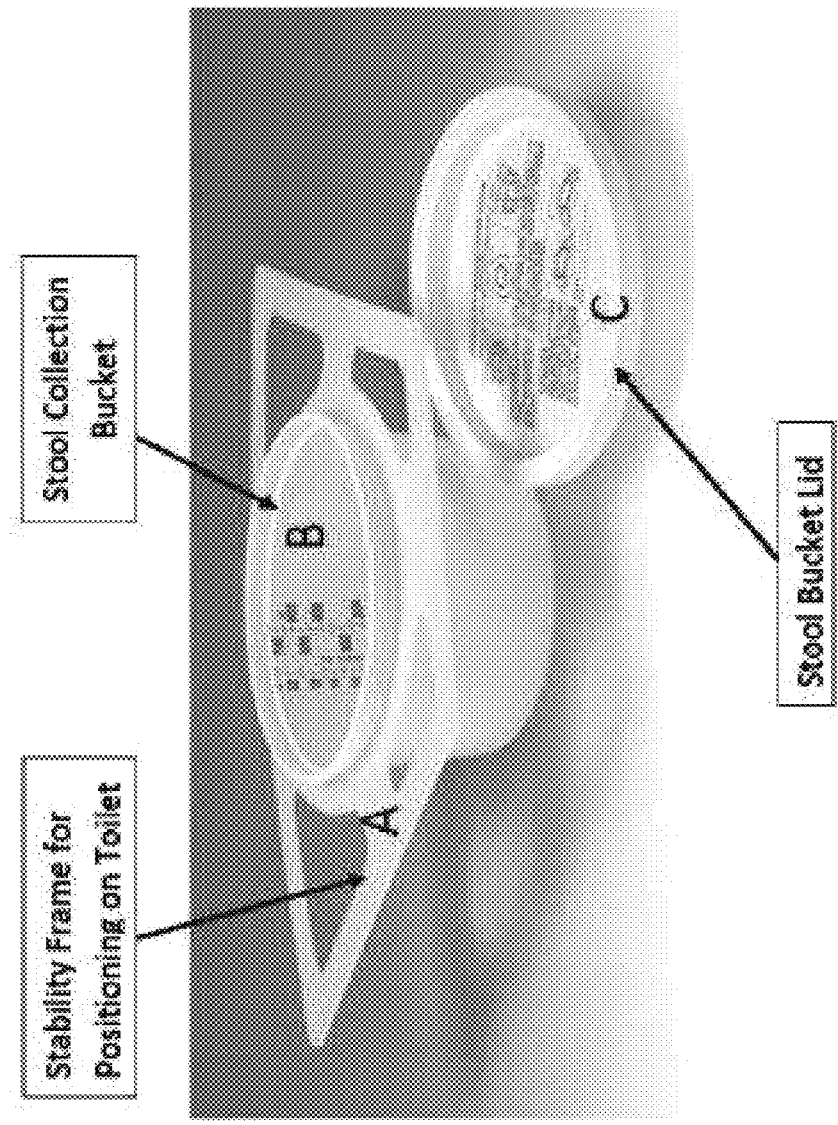
FIG. 9 depicts an exemplary stool collection device. This device can have three separate components: a stability frame for positioning the collection bucket on the toilet (A); a barcoded stool collection bucket (B), and a stool bucket lid with a label for collection date and time (C).

The disclosure provides methods to collect stool samples, and methods to process and extract microbes from the stool samples for further analysis. The entire stool sample can be collected with the aid of mechanical tools or sampling devices. An exemplary device is shown in FIG. 9. Other non-limiting mechanical tools or sampling device include sterile container, sterile tube, swab, spoon, scoop, and spatula.

Stool samples can be collected at any time during the entire course of treatment. For example, the stool samples can be collected a day before the start of the treatment (Day 0) which can be used as the baseline for further analysis. The stool sample can be collected on the start day of the treatment (Day 1). The stool samples can be collected on Day 2, Day 3, Day 4, Day 5, Day 6, Day 7, Day 8, Day 9, Day 10, Day 11, Day 12, Day 13, Day 14, Day 15, Day 16, Day 17, Day 18, Day 19, Day 20, Day 21, Day 22, Day 23, Day 24, Day 25, Day 26, Day 27, Day 28, Day 29, Day 30, Day 31, Day 32, Day 33, Day 34, Day 35, Day 36, Day 37, Day 38, Day 39, Day 40, Day 41, Day 42, Day 43, Day 44, Day 45, Day 46, Day 47, Day 48, Day 49, Day 50, Day 51, Day 52, Day 53, Day 54, Day 55, Day 56, Day 57, Day 58, Day 59, Day 60, Day 61, Day 62, Day 63, Day 64, Day 65, Day 66, Day 67, Day 68, Day 69, Day 70, Day 71, Day 72, Day 73, Day 74, Day 75, Day 76, Day 77, Day 78, Day 79, Day 80, Day 81, Day 82, Day 83, Day 84, Day 85, Day 86, Day 87, Day 88, Day 89, Day 90, Day 91, Day 92, Day 93, Day 94, Day 95, Day 96, Day 97, Day 98, Day 99, Day 100, or every day until the end of the treatment course. For each sample collection day, the stool samples can be collected at any time during the day. In some cases, the stool samples can be collected once per collection day, or more than once per collection day.

In some cases, swabs of fresh stool or rectal swabs can be collected for further microbial analysis. In some cases, a scoop of the stool sample can be collected for further microbial analysis. In some cases, an entire stool sample can be collected for further microbial analysis. An entire stool sample containing all fecal matter from a bowel movement can be collected, resuspended in a solution, and aliquoted out for parallel assessment by different microbiome profiling methods.

In some cases, an entire stool sample can be processed shortly after a bowel movement by suspending in PBS, water or preserving solutions. Non-limiting examples of preserving solutions include formalin, polyvinyl-alcohol, merthiolate-iodineformaldehyde, sodium acetate-acetic acid-formalin, Schaudinn's Fixative, Modified PVA copper or zinc, One-Vial Fixatives (such as Ecofix, Parasafe, Unifix, Protofix, STF, and others that may be available). The final concentration (% v/v) of the preserving solution can be at least 1%, 2%, 3%, 4%, 5%, 6%, 7%, 8%, 9%, 10%, 11%, 12%, 13%, 14%, 15%, 16%, 17%, 18%, 19%, or 20%. The resuspended stool sample can be homogenized in a homogenizer with a paddle (e.g. Stomacher). The homogenized stool sample then can be aliquoted into 2 or more subsamples for different downstream analysis. In some cases, the volume of the sub-sample can be about 1 mL, about 2 mL, about 3 mL, about 4 mL, about 5 mL, about 6 mL, about 7 mL, about 8 mL, about 9 mL, or about 10 mL. In some cases, the volume of the sub-sample can be 0-1 mL, 1-2 mL, 2-3 mL, 3-4 mL, 4-5 mL, 5-6 mL, 6-7 mL, 7-8 mL, 8-9 mL, or 9-10 mL.

To preserve the microbial communities in the stool samples, the collected stool samples can be either frozen or immediately processed for genetic material extraction. In some cases, the entire stool sample is frozen immediately after collection, or within 5 min after collection, or within 10 min after collection, or within 15 min after collection, or within 20 min after collection, or within 30 min after collection, or within 40 min after collection, or within 50 min after collection, or within 1 hour after collection, or within 2 hours after collection. In some cases, the entire stool sample can be frozen at temperature on or below −80° C., or at temperature on or below −70° C., or at temperature on or below −60° C., or at temperature on or below −50° C., or at temperature on or below −40° C., or at temperature on or below −30° C., or at temperature on or below −20° C. or at temperature on or below −10° C., or at temperature on or below 0° C.

Degradation of DNA or RNA in the collected samples can occur when the samples are exposed to environment outside of human body. To better preserve the microbial communities in the stool samples and prevent sample degradation, the stool samples can be collected in situ by a remotely controlled sample collection mechanism. The remote control mechanism can ensure the sample collection step is done at the desired location and at the desired time. The in situ sample collection mechanism can further comprise some inhibitory agents that will prevent DNA or RNA degradation immediately upon sample collection.

For example, a capsule or equivalent collection tool ingested in the human body can be controllably located at a desired location for sample collection. The capsule or equivalent collection tools can have ON or OFF states which can be originally set at OFF state and can be later switched to ON state when it reaches the desired location, for example, transverse colon, ascending colon, descending colon, cecum, ileum, jejunum, duodenum, or rectum. At OFF sate, the collection tools may not collect samples, whereas at ON state, the collection tools can collect one or more samples. In some cases, the ON state can be achieved by a timer mechanism. In some cases, the ON state can be achieved by a pH sensor. In some cases, the ON state can be controlled by an external radio signal. In some cases, the ON state can be controlled by any combinations of the above mentioned mechanisms.

The capsule or equivalent collection tools can contain an inactivating agent to inhibit enzymatic activities that can be responsible for nucleic acid or protein degradation. The enzymes for nucleic acid degradation can include, but are not limited to, various 5' to 3' exonucleases, 3' to 5' exonucleases, and endonucleases for example, exonuclease I, exonuclease II, exonuclease III, exonuclease IV, exonuclease V, exonuclease VI, exonuclease VII, exonuclease VIII, endonuclease.

In some cases, the in situ collection tool can be a capsule.

In some cases, the capsule or equivalent collection tools can further be equipped with a mechanism for external determination of its location in the human body, for example, in the gut. In some cases, the mechanism can be a radio. In some cases, the mechanism can be a RFID.

Different collection mechanisms can be used. In some applications, the collection mechanism can be a syringe-like apparatus that can be activated to suck samples in. In some applications, the collection mechanism can be porous membrane or semi-permeable matrix that can expand to immobilize and inactivate the sample. In some other applications, the collection mechanism can be a capsule chamber with a controllable door or cap or lid that can be opened for sample collection.

In some cases, a series of capsules or equivalent collection tools, ingested in a time course, can be used to collect samples in a time dependent manner. The sample collected in this time dependent manner can be used to track and create a time series of conditions in the human body.

The disclosure provides methods for microbiome profiling. Microbiome profiling can be used to assess engraftment of administered microbes. Microbiome profiling can also be used to customize compositions for a subject. Methods for profiling a microbiome are discussed in U.S. patent application Ser. No. 14/437,133, which is incorporated herein by reference in its entirety for all purposes. An exemplary method can comprise at least one of the following steps: obtaining a biological sample from a subject; measuring at least one microbe in the biological sample of the subject; detecting or measuring the presence or absence of at least one microbe upon measuring; and generating a report that provides details about the determined microbiome profile.

A biological sample can be any sample type from any microbial habitat on the body of a subject. Non-limiting examples of microbial habitats include skin habitat, umbilical habitat, vaginal habitat, amniotic fluid habitat, conjunctival habitat, intestinal habitat, stomach habitat, gut habitat, oral habitat, nasal habitat, gastrointestinal tract habitat, respiratory habitat, and urogenital tract habitat. A biological sample can be tailored to the specific application. The biological sample can be for example, whole blood, serum, plasma, mucosa, saliva, cheek swab, urine, stool, cells, tissue, bodily fluid, lymph fluid, CNS fluid, and lesion exudates. A combination of biological samples can be used with the methods of the disclosure. In some cases, the biological sample is a stool sample.

Cell lysis and/or extraction of nucleic acids from the biological sample can be performed by any suitable methods including physical methods, chemical methods, or a combination of both. Nucleic acids can be isolated from the biological sample using shearing methods, which preserve the integrity and continuity of genomic DNA.

An amplicon approach can be used to prepare the extracted nucleic acids for microbiome profiling. In some cases, the method does not use an amplification step. Examples of such methods include preparation of samples for sequencing by Whole Genome Shotgun (WGS) sequencing. These approaches can provide a benefit by removing amplification bias that can skew microbial distributions.

Profiling methods can comprise determining sequence information of ribosomal RNA (rRNA) operon, 16S rRNA, 23S rRNA, rRNA internal transcribed spacer, intergenic regions, variable regions, and any combination thereof. The methods can comprise use of target-specific nucleic acid probes. The methods can comprise use of sequencing such as next-generation sequencing. The methods can comprise use of long read sequencing.

EXAMPLES

Example 1: Preclinical Study in Rodents

This study was performed to study effects of a microbial composition of the disclosure following daily administration to Sprague Dawley Rats (40 animals) with time points through 28 days.

Dosing regimen used in the study is shown in Table 1. Four study groups were used: placebo (i.e. no microbes), composition comprising strain 1 only; composition comprising strains 1+5+6+8; and composition comprising strains 5+6+8. Strain 1 is a mucin degrading microbe, *Akkermansia muciniphila*. Strains 5, 6, and 8 are butyrate-producing microbes *Clostridium beijerinckii, Clostridium butyricum*, and *Eubacterium hallii*, respectively. PO denotes per os (oral administration). Microbial amount used per serving size is shown in Table 2.

TABLE 1

Dose Administration

| Group | Number of Animals Males | Dosing Regimen |
| --- | --- | --- |
| 1) Placebo | 10 | PO × 28 days |
| 2) Strain 1 only | 10 | PO × 28 days |
| 3) Strains 1 + 5 + 6 +8 | 10 | PO × 28 days |
| 4) Strains 5 + 6 + 8 | 10 | PO × 28 days |

TABLE 2

Microbial amount (CFU per serving size)

| *Akkermansia muciniphila* | *Clostridium beijerinckii* | *Clostridium butyricum* | *Eubacterium hallii* |
| --- | --- | --- | --- |
| $1.69 \times 10^9$ | $4.18 \times 10^8$ | $2.10 \times 10^8$ | $9.06 \times 10^6$ |

Route of Compound Administration: The compositions were administered orally (Per os, PO) to animals as described in Table 1.

Dosing Preparation: A separate vial of lyophilized powder was used for each study arm for each dosing day along with a vial of diluent packaged under anaerobic conditions. Before administration, the diluent was drawn into a syringe and injected into the vial of lyophilized powder. Then, the appropriate amount was withdrawn and administered to each of the 10 animals in that study arm as quickly as possible.

Test System:
  Main Study Animals: 40 Crl: CD (SD) male rats; Extra Animals: 4 Crl: CD (SD) male rats
  Clinical Observations: Performed routinely at each scheduled time point.
  Body Weights: Body weights were recorded prior to each administration of composition.

Blood/Sample Collections:
  a) Feces were collected from all animals on Days 0, 1, 2, 3, 7, 14, 21, and 28. On these days, feces were collected in three intervals over a 24 hour period. Additionally, feces were collected on n=5/animals/group on day 34 and/or day 35 as above. Feces were collected, frozen, and transferred to testing facility after each sample interval was collected (1,020 samples).
  b) Terminal blood sample-Blood (as much as possible) was collected from all animals at the end of the study. An aliquot of the blood was processed appropriately and analyzed for Clinical Chemistry and CBC with Differential (Day 28 sacrifice animals only). The remainder was processed to either serum or plasma, frozen, and shipped to a testing facility. Number of samples:
    Clin Path—20 samples
    Terminal samples—40 samples
  c) Necropsy—n=5 animals/group were sacrificed on Day 28 and the remainder of the animals on Day 35 (after a 7 day washout).
  Day 28 necropsy—Colon, Proximal small intestine, and Distal small intestine were collected from all animals. Samples were flash frozen and shipped to testing facility.
  Day 35 necropsy—gross necropsy (no samples collected).

Results of the study are shown in FIGS. 3-6, which illustrate data obtained from fecal samples of rats in the various study groups and shows microbial detection using target-specific nucleic acid probes. The results demonstrated that select microbes administered orally to the rodents were engrafted in the gastrointestinal tract.

Figure 3:
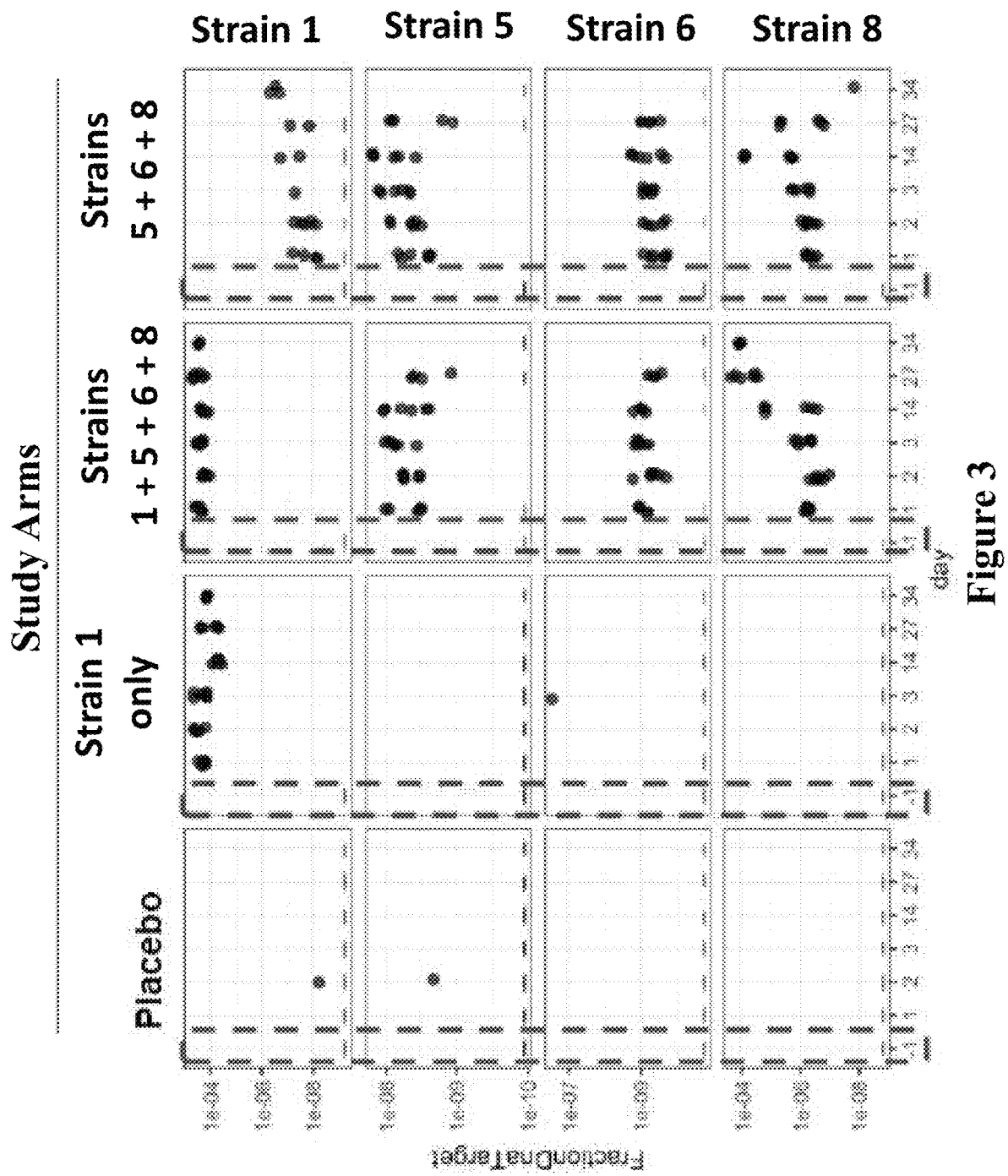
FIG. 3 illustrates data from a rodent study to evaluate engraftment of a microbial composition of the disclosure. Strain 1 is a mucin-degrading microbe, strains 5, 6 and 8 are butyrate producing microbes. The dashed boxes corresponding to day −1 refer to the baseline (i.e. pre-intervention) sample for all groups. The baseline did not have any false positive hits for any of the 4 study groups. This showed that the nucleic acid probes used for detection were highly specific to detecting only the exogenous microbes being administered. Additionally, at baseline the study rats lacked the exogenous microbes being administered in the microbial compositions.

In FIG. 3, the dashed boxes correspond to day −1 and refer to the baseline sample (i.e. pre-intervention) for each group. The "Placebo" panel illustrated that there was very low false positive detection due to the high specificity of the nucleic acid probes used for the study. Day "−1" had no false positive hits for any of the groups, which further illustrated that the nucleic acid probes designed for the study were specific for the microbial DNA being tested. This also showed that the exogenous microbes that were part of the compositions were absent in the rats prior to the intervention.

Figure 4:
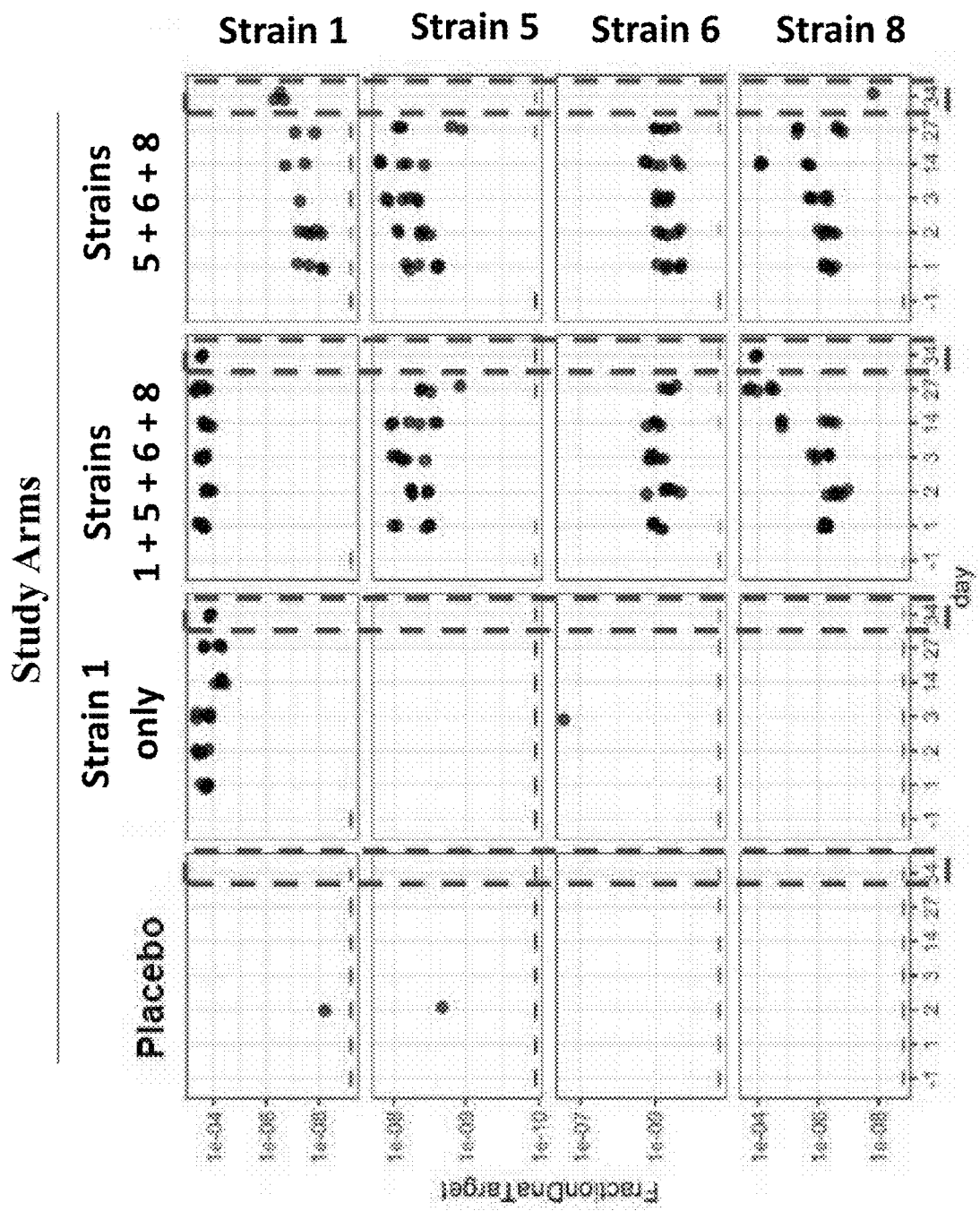
FIG. 4 illustrates data from a rodent study to evaluate engraftment of a microbial composition of the disclosure. Strain 1 is a mucin-degrading microbe, strains 5, 6 and 8 are butyrate-producing microbes. The dashed boxes corresponding to day 34 refer to the washout (i.e. post-intervention) sample for all groups. Engraftment of butyrate-producing microbe strain 8 only occurred when the microbial composition also comprised the mucin-degrading microbial strain 1 (compare bottom row, two right most facets).

In FIG. 4, the dashed boxes correspond to day 34 and refer to the washout sample (i.e. 1 week post-intervention) for each group. Data from the washout period for groups receiving strain 1 only, and strains 1+5+6+8 showed that strains 1 and 8 engrafted at detectable levels. The data also showed that strain 8 increased with time and only engrafted when administered with strain 1. In the absence of strain 1 (see study group panel with strains 5+6+8), strain 8 did not engraft. Thus engraftment of strain 1, a mucin-degrading microbe, promoted engraftment of strain 8, a butyrate-producing strain. Further, it was also observed that while strain 1 engrafted by about day 2 of intervention, strain 8 required more than two weeks (e.g., three weeks) of exposure in the presence of strain 1 for engraftment to occur. The increase in the amount of detected strain 8 by day 14 can be an indicator of engraftment at about the 2 week mark.

Figure 5:
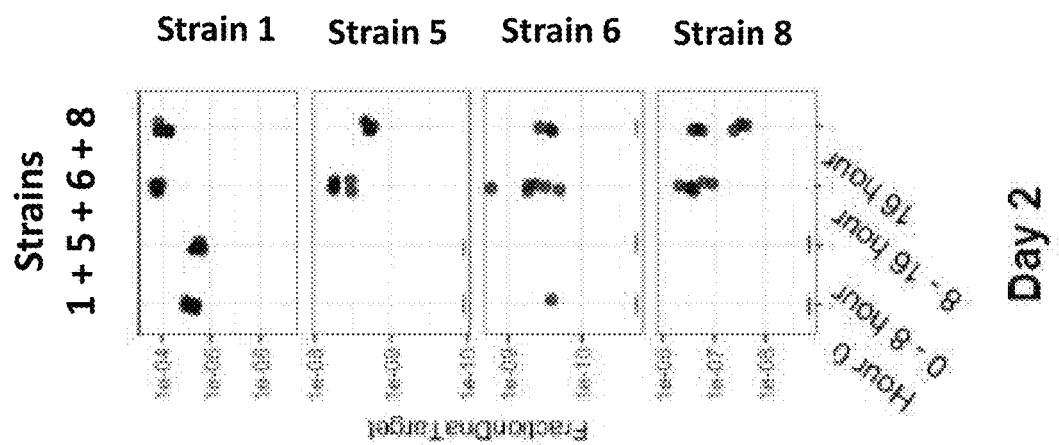
FIG. 5 illustrates data from day 2 of a rodent study to evaluate engraftment of a microbial composition of the disclosure. Strain 1 is a mucin-degrading microbe, strains 5, 6 and 8 are butyrate-producing microbes. A microbial composition comprising strains 1, 5, 6, and 8 was given at 0 hour. Transit time for the microbial composition through the gastrointestinal tract of the rats was calculated to be within about 8-16 hour window. Strain 1 was detected in rat fecal matter before the transit time. This indicated potential engraftment by strain 1 from the previous day's administration. This was confirmed by detection of strain 1 in the washout period. Thus, a ratio of detection signals from early to late collection times can be used as an engraftment indicator of an administered microbe.

FIG. 5 illustrates detection data obtained from day 2 of intervention for the group administered strains 1+5+6+8. Hour 0 represents the time of administration of the microbial composition. Transit time for the microbial composition through the gastrointestinal tract of the rats was calculated to be within about 8-16 hour window. Strain 1 was detected in rat fecal matter before the transit time indicating likely engraftment of Strain 1. This suggested that strain 1 may have engrafted. This was confirmed by detection of strain 1 in the washout samples. Thus, a ratio of detection signals from early to late collection times (for example, corresponding to different times from administration) can be used as an engraftment indicator of an administered microbe. For example, a ratio between a strain detected at an early collection time (e.g. 8-16 hours post administration) and a late collection time (e.g., 16 hours post administration) can be indicative of strain engraftment (e.g, where stain levels remain detectable or consistent over time). In some instances, the amount of strain detected may vary based on administration regimen and transit time through the gastrointestinal tract for collection. A detected presence of an administered strain in a fecal sample before or after a transit window (e.g., an expected time for an administered microbe to pass through a gastrointestinal tract of a subject) may be indicative of engraftment. Such detected presence may indicate that an administered strain is present in the gut even in the absence of administration (e.g., during or after the washout period).

Figure 6:
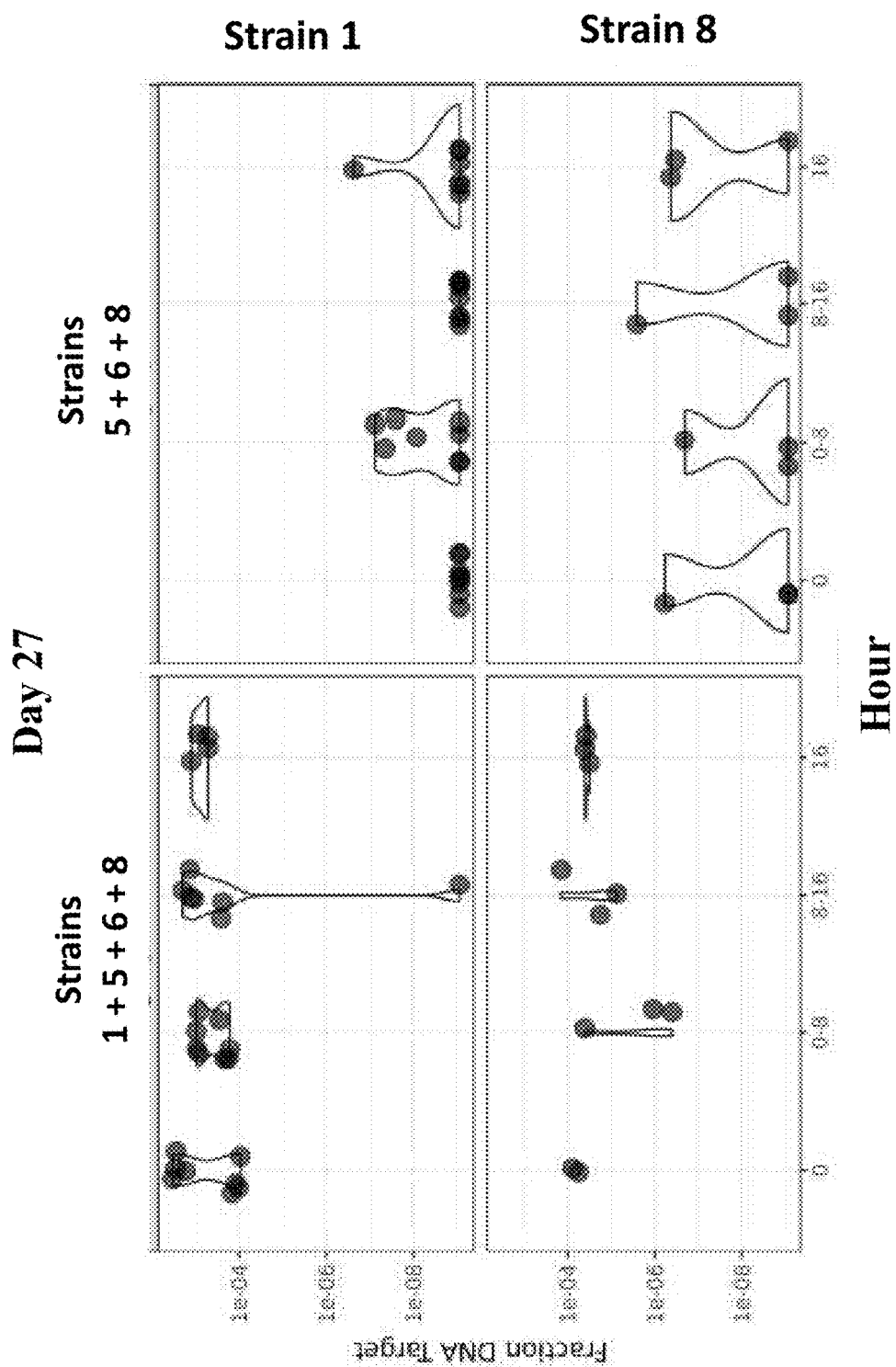
FIG. 6 illustrates data from day 27 of a rodent study to evaluate engraftment of a microbial composition of the disclosure. Strain 1 is a mucin-degrading microbe, strains 5, 6 and 8 are butyrate-producing microbes. The group illustrated in the left column panels was administered strains 1, 5, 6, and 8. The group illustrated in the right column panels was administered strains 5, 6, and 8. Since both microbes 1 and 8 had engrafted by day 27 of the intervention, both were detected in the 0 and 0-8 hour collection time points for the left panel group that was administered strains 1+5+6+8, even though transit time was about 8-16 hours. Thus, a ratio of detection signals from early to late collection times can be indicative of the current engraftment status. This can be advantageous, for example, because the approach of utilizing a final washout period can only report on the engraftment status at the end of a study.

FIG. 6 illustrates detection data obtained from day 27 of intervention for groups administered strains 1+5+6+8 (left panel) and strains 5+6+8 (right panel). Both strains 1 and 8 were detected in the 0 and 0-8 hour collection time points for the group that was administered strains 1+5+6+8, even though transit time was about 8-16 hours. This indicated that strains 1 and 8 had already engrafted, and was confirmed by detection in the washout period. Thus, this data further shows that a ratio of detection signals from early to late collection times can be indicative of continuous engraftment.

Data from clinical observation of the animals, plasma chemistry, hematology panels, and necropsy evaluation confirmed that there were no adverse effects on the rodents from the administered compositions.

Example 2: Clinical Trial

Figure 7:
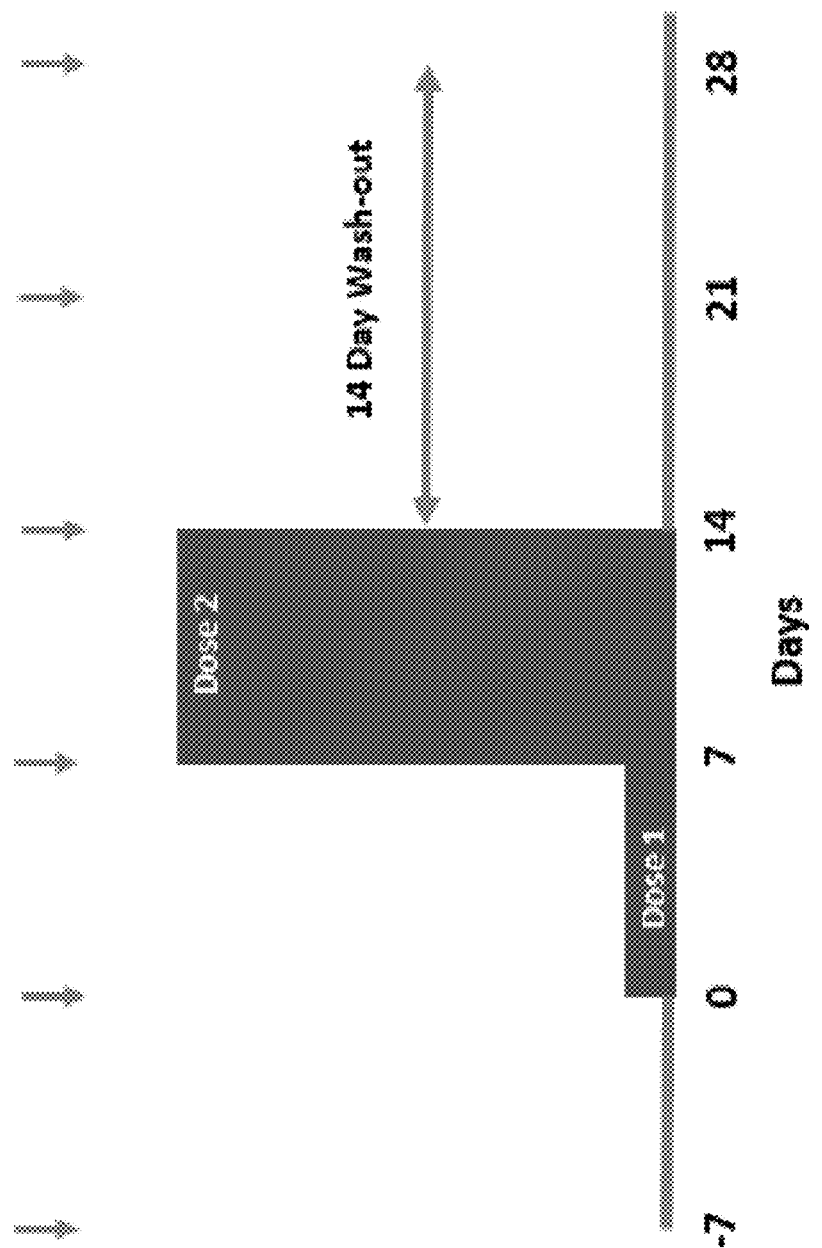
FIG. 7 depicts an overview of an exemplary study design of administration of a microbial composition of the disclosure. The total duration of a subject's participation can be approximately 35 days with a screening visit occurring 3 to 7 days prior to the baseline visit at Day 0, where the initiation of administration and consumption occurs. Following the initial consumption, active participation can extend through Day 28. The arrows indicate the clinic visits where the subject's medical history can be reviewed at screening and clinical history can be reviewed at Day 7, Day 14, Day 21, and Day 28. Stool samples, clinical chemistries, hematology profiles, plasma SCFA, and/or cytokine panel can be collected at the time of each of these clinic visits.
Figure 8:
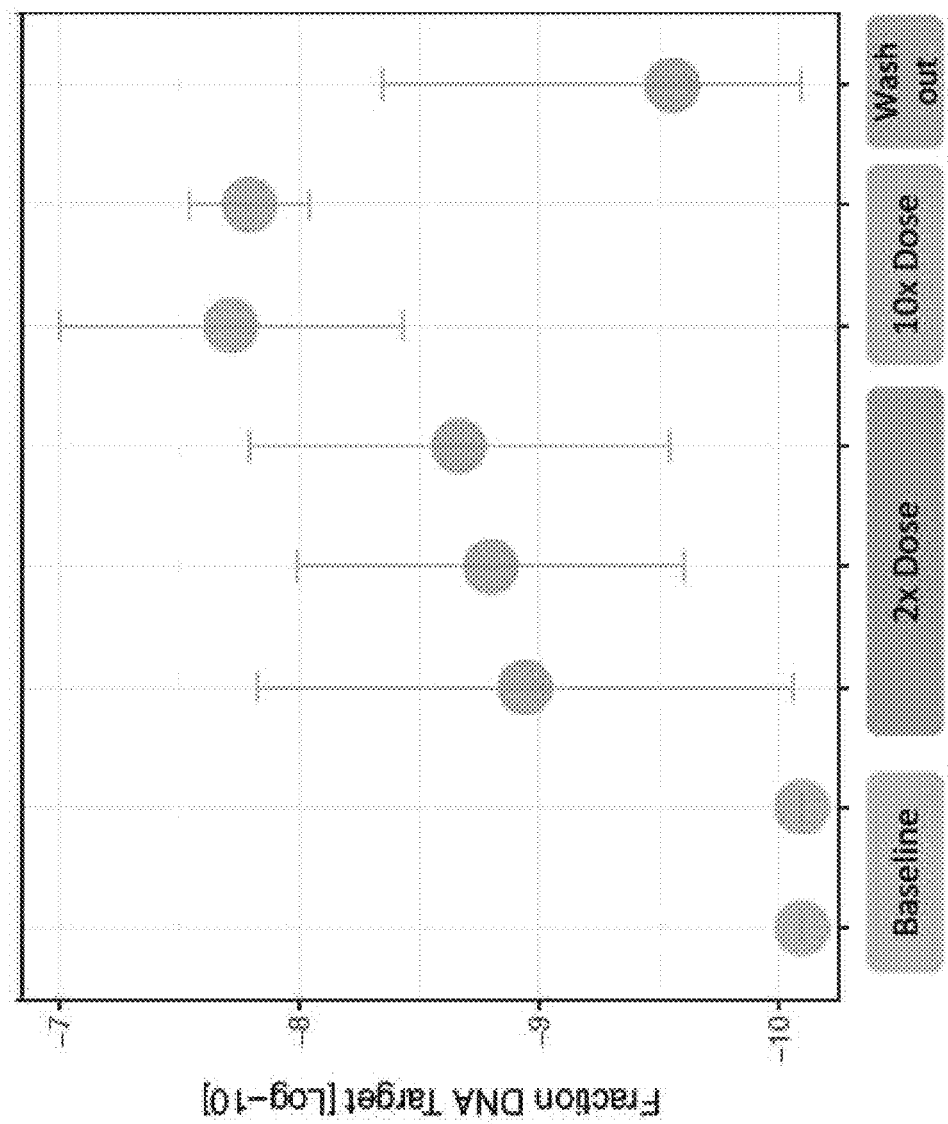
FIG. 8 depicts illustrative data showing the fraction (relative to total DNA) of a specific DNA marker for the exogenous microbes detected in the fecal matter of subjects administered a therapeutic composition of the disclosure during different stages of the treatment. The exogenously administered microbes were detected in the washout period of some subjects, demonstrating that engraftment had occurred.

Format of the study: This is an open label uncontrolled amount escalation study wherein all subjects receive a study food product comprising microbes of the disclosure. The study is focused on evaluating safety and detection of orally administered microbes in the stool during and after the amount escalation. The initial amount of the composition was guided by the amount administered to male Sprague Dawley rats for 28 days without adverse effects (see Example 1). FIG. 7 and Table 3 show dosage for this study. A lower amount is administered from day 0-6. If no untoward effects are observed after 7 days of administration, the amount consumed is increased 5-fold for days 7 to 14. Subjects then enter a 14-day wash-out period when no study food product is administered.

TABLE 3

| | Dosage | | |
|---|---|---|---|
| Study Days | *Clostridium beijerinckii,* | *Clostridium butyricum* (CFU/amount) | *B. infantis* (CFU/amount) |
| Dose 1/Low Amount (Days 0-6) | $7.0 \times 10^9$ | $4.0 \times 10^9$ | $2.0 \times 10^8$ |
| Dose 2/High Amount (Days 7-14) | $3.5 \times 10^{10}$ | $2.0 \times 10^{10}$ | $1.0 \times 10^9$ |

Monitoring for adverse effects is continued through Day 28 with stool samples being collected on Day 20 and 27. The subject's medical history is reviewed at screening and clinical history reviewed at Day 7, Day 14, Day 21, and Day 28. Stool samples, clinical chemistries, hematology profiles, plasma SCFA, and cytokine panel are collected at the time of each of these clinic visits.

Duration of the study: The total duration of a subject's participation is approximately 35 days with a screening visit occurring 3 to 7 days prior to the baseline visit at Day 0, where the initiation of consumption occurs. Following the initial consumption, active participation extends through Day 28.

Number of Subjects: Approximately 20 healthy subjects

Microbial Composition and Administration: Coated capsules comprising the substantially dry population of lyophilized microbes are used. The capsules are designed to disintegrate in the intestine. Subjects consume 1 to 5 capsules within 30 minutes prior to the start of breakfast and dinner for 14 days. The allocation of study capsules is outlined in Table 4. Each capsule comprises microbes (*Clostridium beijerinckii, Clostridium butyricum*, and *B. infantis*), inulin (chicory), sucrose, trehalose, glycerin, maltodextrin and hydroxypropyl methylcellulose. The study food product is provided in sealed, labelled brown screw cap bottles. Each bottle contains the required number of capsules to support 7 days of administration plus 10 capsules to cover any need for replacement amounts and insure that at least 3 capsules remain for return for repeat stability testing. At each of the amount levels, all capsules have the same content. The study food product is stored refrigerated except for dispensing to the subject and at the time of consumption for removal of designated amount.

TABLE 4

Allocation of Study Food Product Capsules

| | Breakfast | Dinner |
|---|---|---|
| Week 1 | 1 Capsules | 1 Capsules |
| Week 2 | 5 Capsules | 5 Capsules |

Study Methods: Prior to all screening and study visits, subjects are asked to fast overnight for at least 10 hours (i.e., no food or beverage except water). Subjects report to the clinical study site in the morning of each scheduled visit (ideally between 0700 and 0900 hours). For all applicable study visits, subjects refrain from administering the morning amount of study product prior to the visit. Subjects bring the study food product along to the study-site to take while in the clinic. For each subject, there are 6 visits in total. The first visit is a screening visit, 3-7 days before the start of the study, where a blood sample is collected. The second visit is on Day 0 (initiation of consumption occurs), where both a blood sample and stool sample(s) are collected. The assessment data using samples collected on Day 0 serve as baseline values. The remaining four visits are on Day 7, Day 14, Day 21, and Day 28. Both blood and stool samples are collected on these visits for outcome assessment.

Treatment outcome assessment: During this study, blood is drawn for various analytes and panels, including chemistry, hematology, SCFA, and inflammatory markers. The total amount of blood drawn (during the entire study) is expected to be <60 mL or 2 ounces for each subject. Entire stool samples are collected and processed immediately after collection. The entire stool samples are aliquoted into 4 fractions, and each fraction is subjected to microbiome profiling methods to detect the administered microbes.

FIG. 8 depicts data showing the relative amount of administered microbes detected in the fecal matter of a subject who is administered the therapeutic composition, during different stages of the treatment. The data showed that engraftment of the administered microbes had occurred as seen in the washout sample.

Example 3: Stool Collection

Stool collection, for example, as required for the study described in Example 2 can be carried out with a stool collection device illustrated in FIG. 9. The stool collection can be carried out from a patient's home. The device has three separate components: a stability frame for positioning the collection bucket on the toilet; a barcoded stool collection bucket, and a stool bucket lid, with, optionally, a label for collection date and time, as shown in FIG. 9. The device can be positioned on the toilet seat in two different ways.

The toilet seat can be lifted and the stool collection device can be placed horizontally on the edges of the toilet bowl. The narrow side of the frame can be positioned to face towards the rear end of the toilet bowl. Depending on the personal anatomy, the narrow side of the frame can be positioned to face the front of the toilet bowl, which may better facilitate acquisition of stool sample. The toilet seat can be lowered to secure the stool collection device.

Instructions to use: Completely empty bladder. Remove all items from the biohazard bag. Use a sanitary wipe to cleanse toilet seat and rim of toilet bowl. Fill out the date (month/day/year) and check the box corresponding to the time of day on the bucket lid label with the provided ballpoint pen. Remove the lid from the bucket and place the lid inside of the biohazard bag. Assemble the device by inserting the Collection Bucket (FIG. 9B) securely into the Stability Frame (FIG. 9A). Do not touch the inside of the bucket. Lift the toilet seat and place the device horizontally on the edges of the toilet bowl. The narrow side of the frame should face towards the rear end of the toilet bowl. Depending on a subject's anatomy, repositioning the narrow side of the frame to face the front of the toilet bowl may better facilitate acquisition of stool sample. Lower the toilet seat to secure the device. Sit on the toilet and arrange yourself so that the stool sample will fall directly into the bucket. Do not urinate or place toilet paper into the Collection Bucket. When finished, use toilet paper to clean yourself and discard used toilet paper outside of the bucket. Flush the toilet. When complete, lift the toilet seat and remove the device from the toilet. Set the device on a flat surface. Push down on the Stability Frame to detach it from the Collection Bucket. Discard frame. Remove the lid from biohazard bag and push the lid onto the Collection Bucket. The lid is secure when a "snap" is heard. Place the sealed Collection Bucket into the empty biohazard bag and close the bag. Place the closed biohazard bag with collected stool sample into a freezer. After 4 hrs or more, pack biohazard bag with collection bucket into an insulated shipment package. Add 2-3 ice packs to the shipment package and ship package to testing facility.

Example 4: Isolation of Mucin-Degrading or Mucin Regulating Microbes Using Selective Media This example describes an illustrative selective medium that was used to isolate a mucin-degrading microbe. The selective media comprises mucin, which serves as the primary energy source. Mucin-degrading microbes can degrade mucin and grow in the selective media while microbes lacking the ability to degrade mucin are unable to grow.

Prepare selective media: The following components were mixed in a final volume of 800 mL: rumen fluid, vitamins, minerals, basal salt solution, calcium chloride, cysteine chloride, and water. The mixture was degassed for 20 minutes and filtered. 2.5 grams of purified mucin was resuspended in 200 mL of distilled water, sealed in a serum vial and autoclaved for 20 min at 121 degrees Celsius. The mucin solution was mixed with the filtered solution to produce the selective media.

Figure 10:
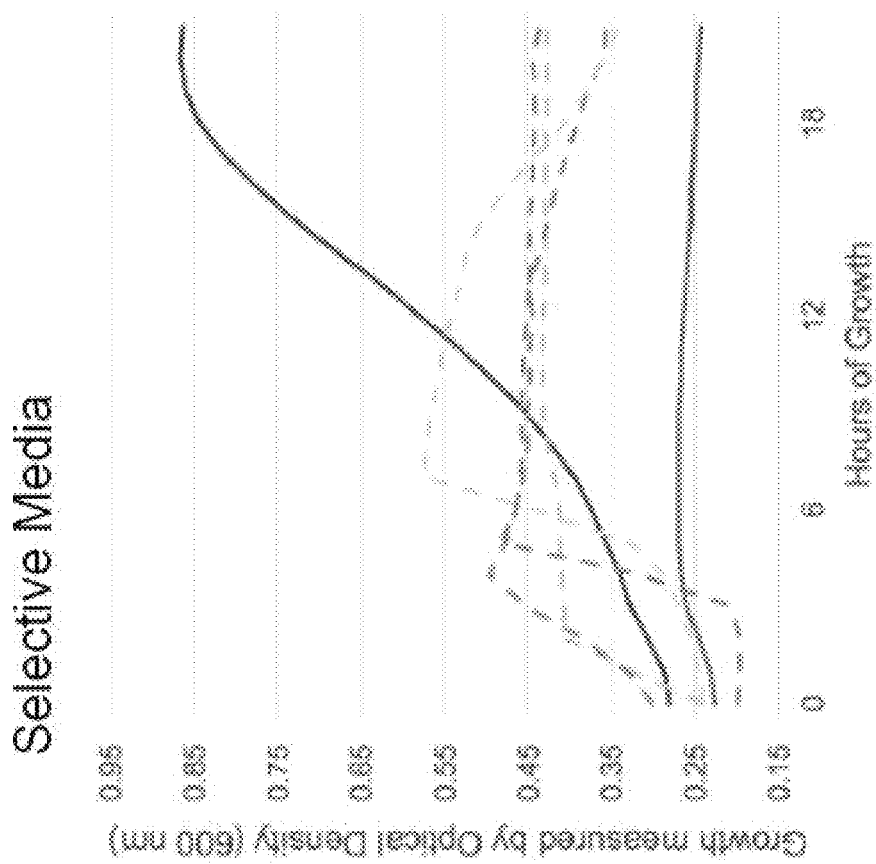
FIG. 10 illustrates microbial growth in selective media for isolating mucin-degrading microbes.

Isolate targets: Fresh stool was used for isolation experiments. The isolated microbes were grown in the selective media. FIG. 10 shows isolates grown on the selective media.

Informatic Screen: Selectively isolated microbes were identified using sequencing and bioinformatics tools.

Characterize New Strains: The identified strains were characterized using genomic and biochemical assays.

Table 5 provides 16S rRNA consensus sequence for six illustrative mucin-degrading *Akkermansia muciniphila* strains identified using methods of the disclosure.

TABLE 5

Illustrative mucin-degrading microbes

| SEQ ID NO. | Strain/Isolate | Sequence |
| --- | --- | --- |
| 1 | Akkermansia muciniphila Isolate 1 | AAAATTAATTTGATGGAGAGTTTGATTCTGGCTCAGAACGAACGCTGG CGGCGTGGATAAGACATGCAAGTCGAACGAGAGAATTGCTAGCTTGCT AATAATTCTCTAGTGGCGCACGGGTGAGTAACACGTGAGTAACCTGCC CCCGAGAGCGGGATAGCCCTGGGAAACTGGGATTAATACCGCATAGT ATCGAAAGATTAAAGCAGCAATGCGCTTGGGGATGGGCTCGCGGCCT ATTAGTTAGTTGGTGAGGTAACGGCTCACCAAGGCGATGACGGGTAGC CGGTCTGAGAGGATGTCCGGCCACACTGGAACTGAGACACGGTCCAG ACACCTACGGGTGGCAGCAGTCGAGAATCATTCACAATGGGGGAAAC CCTGATGGTGTGACGCCGCGTGGGGGAATGAAGGTCTTCGGATTGTAA ACCCCTGTCATGTGGGAGCAAATTAAAAAGATAGTACCACAAGAGGA AGAGACGGCTAACTCTGTGCCAGCAGCCGCGGTAATACAGAGGTCTC AAGCGTTGTTCGGAATCACTGGGCGTAAAGCGTGCGTAGGCTGTTTCG TAAGTCGTGTGTGAAAGGCGCGGGCTCAACCCGCGGACGGCACATGA TACTGCGAGACTAGAGTAATGGAGGGGGAACCGGAATTCTCGGTGTA GCAGTGAAATGCGTAGATATCGAGAGGAACACTCGTGGCGAAGGCGG GTTCCTGGACATTAACTGACGCTGAGGCACGAAGGCCAGGGGAGCGA AAGGGATTAGATACCCCTGTAGTCCTGGCAGTAAACGGTGCACGCTTG GTGTGCGGGGAATCGACCCCCTGCGTGCCGGAGCTAACGCGTTAAGCG TGCCGCCTGGGGAGTACGGTCGCAAGATTAAAACTCAAAGAAATTGA CGGGGACCCGCACAAGCGGTGGAGTATGTGGCTTAATTCGATGCAAC GCGAAGAACCTTACCTGGGCTTGACATGTAATGAACAACATGTGAAAG CATGCGACTCTTCGGAGGCGTTACACAGGTGCTGCATGGCCGTCGTCA GCTCGTGTCGTGAGATGTTTGGTTAAGTCCAGCAACGAGCGCAACCCC TGTTGCCAGTTACCAGCACGTGAAGGTGGGGACTCTGGCGAGACTGCC CAGATCAACTGGGAGGAAGGTGGGGACGACGTCAGGTCAGTATGCC CTTATGCCCAGGGCTGCACACGTACTACAATGCCCAGTACAGAGGGGG CCGAAGCCGCGAGGCGGAGGAAATCCTGAAAACTGGGCCCAGTTCGG ACTGTAGGCTGCAACCCGCCTACACGAAGCCGGAATCGCTAGTAATGG CGCATCAGCTACGGCGCCGTGAATACGTTCCCGGGTCTTGTACACACC GCCCGTCACATCATGGAAGCCGGTCGCACCCGAAGTATCTGAAGCCAA |

TABLE 5-continued

Illustrative mucin-degrading microbes

| SEQ ID NO. | Strain/Isolate | Sequence |
|---|---|---|
| | | CCGCAAGGAGGCAGGGTCCTAAGGTGAGACTGGTAACTGGGATGAAG<br>TCGTAACAAGGTAGCCGTAGGGGAACCTGCGGCTGGATCACCTCCTTT<br>CT |
| 2 | Akkermansia muciniphila Isolate 2 | AGAGTTTGATTCTGGCTCAGAACGAACGCTGGCGGCGTGGATAAGACA<br>TGCAAGTCGAACGAGAGAATTGCTAGCTTGCTAATAATTCTCTAGTGG<br>CGCACGGGTGAGTAACACGTGAGTAACCTGCCCCCGAGAGCGGGATA<br>GCCCTGGGAAACTGGGATTAATACCGCATAGTATCGCAAGATTAAAGC<br>AGCAATGCGCTTGGGGATGGGCTCGCGGCCTATTAGTTAGTTGGTGAG<br>GTAACGGCTCACCAAGGCGATGACGGGTAGCCGGTCTGAGAGGATGT<br>CCGGCCACACTGGAACTGAGACACGGTCCAGACACCTACGGGTGGCA<br>GCAGTCGAGAATCATTCACAATGGGGGAAACCCTGATGGTGCGACGC<br>CGCGTGGGGGAATGAAGGTCTTCGGATTGTAAACCCCTGTCATGTGGG<br>AGCAAATTAAAAAGATAGTACCACAAGAGGAAGAGACGGCTAACTCT<br>GTGCCAGCAGCCGCGGTAATACAGAGGTCTCAAGCGTTGTTCGGAATC<br>ACTGGGCGTAAAGCGTGCGTAGGCTGTTTCGTAAGTCGTGTGTGAAAG<br>GCGCGGGCTCAACCCGCGGACGGCACATGATACTGCGAGACTAGAGT<br>AATGGAGGGGGAACCGGAATTCTCGGTGTAGCAGTGAAATGCGTAGA<br>TATCGAGAGGAACACTCGTGGCGAAGGCGGGTTCCTGGACATTAACTG<br>ACGCTGAGGCACGAAGGCCAGGGGAGCGAAAGGGATTAGATACCCCT<br>GTAGTCCTGGCAGTAAACGGTGCACGCTTGGTGTGCGGGGAATCGACC<br>CCCTGCGTGCCGGAGCTAACGCGTTAAGCGTGCCGCCTGGGGAGTACG<br>GTCGCAAGATTAAAACTCAAAGAAATTGACGGGGACCCGCACAAGCG<br>GTGGAGTATGTGGCTTAATTCGATGCAACGCGAAGAACCTTACCTGGG<br>CTTGACATGTAATGAACAACATGTGAAAGCATGCGACTCTTCGGAGGC<br>GTTACACAGGTGCTGCATGGCCGTCGTCAGCTCGTGTCGTGAGATGTT<br>TGGTTAAGTCCAGCAACGAGCGCAACCCCTGTTGCCAGTTACCAGCAC<br>GTGAAGGTGGGGACTCTGGCGAGACTGCCCAGATCAACTGGGAGGAA<br>GGTGGGGACGACGTCAGGTCAGTATGGCCCTTATGCCCAGGGCTGCAC<br>ACGTACTACAATGCCCAGTACAGAGGGGGCCGAAGCCGCGAGGCGGA<br>GGAAATCCTAAAAACTGGGCCCAGTTCGGACTGTAGGCTGCAACCCGC<br>CTACACGAAGCCGGAATCGCTAGTAATGGCGCATCAGCTACGGCGCC<br>GTGAATACGTTCCCGGGTCTTGTACACACCGCCCGTCACATCATGGAA<br>GCCGGTCGCACCCGAAGTATCTGAAGCCAACCGCAAGGAGGCAGGGT<br>CCTAAGGTGAGACTGGTAACTGGGATGAAGTCGTAACAAGGTAGCCG<br>TAGGGGAACCTGCGGCTGGATCACCTCCTTTCT |
| 3 | Akkermansia muciniphila Isolate 3 | CTGGCGGCGTGGATAAGACATGCAAGTCGAACGAGAGAATTGCTAGC<br>TTGCTAATAATTCTCTAGTGGCGCACGGGTGAGTAACACGTGAGTAAC<br>CTGCCCCCGAGAGCGGGATAGCCCTGGGAAACTGGGATTAATACCGC<br>ATAGTATCGAAAGATTAAAGCAGCAATGCGCTTGGGGATGGGCTCGC<br>GGCCTATTAGTTAGTTGGTGAGGTAACGGCTCACCAAGGCGATGACGG<br>GTAGCCGGTCTGAGAGGATGTCCGGCCACACTGGAACTGAGACACGG<br>TCCAGACACCTACGGGTGGCAGCAGTCGAGAATCATTCACAATGGGG<br>GAAACCCTGATGGTGCGACGCCGCGTGGGGAATGAAGGTCTTCGGA<br>TTGTAAACCCCTGTCATGTGGGAGCAAATTAAAAAGATAGTACCACAA<br>GAGGAAGAGACGGCTAACTCTGTGCCAGCAGCCGCGGTAATACAGAG<br>GTCTCAAGCGTTGTTCGGAATCACTGGGCGTAAAGCGTGCGTAGGCTG<br>TTTCGTAAGTCGTGTGTGAAAGGCGCGGGCTCAACCCGCGGACGGCAC<br>ATGATACTGCGAGACTAGAGTAATGGAGGGGGAACCGGAATTCTCGG<br>TGTAGCAGTGAAATGCGTAGATATCGAGAGGAACACTCGTGGCGAAG<br>GCGGGTTCCTGGACATTAACTGACGCTGAGGCACGAAGGCCAGGGGA<br>GCGAAAGGGATTAGATACCCCTGTAGTCCTGGCAGTAAACGGTGCAC<br>GCTTGGTGTGCGGGGAATCGACCCCCTGCGTGCCGGAGCTAACGCGTT<br>AAGCGTGCCGCCTGGGGAGTACGGTCGCAAGATTAAAACTCAAAGAA<br>ATTGACGGGGACCCGCACAAGCGGTGGAGTATGTGGCTTAATTCGATG<br>CAACGCGAAGAACCTTACCTGGGCTTGACATGTAATGAACAACATGTG<br>AAAGCATGCGACTCTTCGGAGGCGTTACACAGGTGCTGCATGGCCGTC<br>GTCAGCTCGTGTCGTGAGATGTTTGGTTAAGTCCAGCAACGAGCGCAA<br>CCCCTGTTGCCAGTTACCAGCACGTGAAGGTGGGGACTCTGGCGAGAC<br>TGCCCAGATCAACTGGGAGGAAGGTGGGGACGACGTCAGGTCAGTAT<br>GGCCCTTATGCCCAGGGCTGCACACGTACTACAATGCCCAGTACAGAG<br>GGGGCCGAAGCCGCGAGGCGGAGGAAATCCTAAAAACTGGGCCCAGT<br>TCGGACTGTAGGCTGCAACCCGCCTACACGAAGCCGGAATCGCTAGTA<br>ATGGCGCATCAGCTACGGCGCCGTGAATACGTTCCCGGGTCTTGTACA<br>CACCGCCCGTCACATCATGGAAGCCGGTCGCACCCGAAGTATCTGAAG<br>CCAACCGCAAGGAGGCAGGGTCCTAAGGTGAGACTGGTAACTGGGAT<br>GAAGTCGTAACAAGGTAGCCGTAGGGGAACCTGCGGCTGGATCACCT<br>CCTTTCTATGGAGCAAGTGCACGGAAGTGCAC |

TABLE 5-continued

Illustrative mucin-degrading microbes

| SEQ ID NO. | Strain/Isolate | Sequence |
|---|---|---|
| 4 | Akkermansia muciniphila Isolate 4 | TGCTAGCTTGCTAATAATTCTCTAGTGGCGCACGGGTGAGTAACACGT GAGTAACCTGCCCCCGAGAGCGGGATAGCCCTGGGAAACTGGGATTA ATACCGCATAGTATCGCAAGATTAAAGCAGCAATGCGCTTGGGGATGG GCTCGCGGCCTATTAGTTAGTTGGTGAGGTAACGGCTCACCAAGGCGA TGACGGGTAGCCGGTCTGAGAGGATGTCCGGCCACACTGGAACTGAG ACACGGTCCAGACACCTACGGGTGGCAGCAGTCGAGAATCATTCACA ATGGGGGAAACCCTGATGGTGCGACGCCGCGTGGGGGAATGAAGGTC TTCGGATTGTAAACCCCTGTCATGTGGGAGCAAATTAAAAAGATAGTA CCACAAGAGGAAGAGACGGCTAACTCTGTGCCAGCAGCCGCGGTAAT ACAGAGGTCTCAAGCGTTGTTCGGAATCACTGGGCGTAAAGCGTGCGT AGGCTGTTTCGTAAGTCGTGTGTGAAAGGCGCGGGCTCAACCCGCGGA CGGCACATGATACTGCGAGACTAGAGTAATGGAGGGGGAACCGGAAT TCTCGGTGTAGCAGTGAAATGCGTAGATATCGAGAGGAACACTCGTGG CGAAGGCGGGTTCCTGGACATTAACTGACGCTGAGGCACGAAGGCCA GGGGAGCGAAAGGGATTAGATACCCCTGTAGTCCTGGCAGTAAACGG TGCACGCTTGGTGTGCGGGGAATCGACCCCCTGCGTGCCGGAGCTAAC GCGTTAAGCGTGCCGCCTGGGGAGTACGGTCGCAAGATTAAAACTCA AAGAAATTGACGGGGACCCGCACAAGCGGTGGAGTATGTGGCTTAAT TCGATGCAACGCGAAGAACCTTACCTGGGCTTGACATGTAATGAACAA CATGTGAAAGCATGCGACTCTTCGGAGGCGTTACACAGGTGCTGCATG GCCGTCGTCAGCTCGTGTCGTGAGATGTTTGGTTAAGTCCAGCAACGA GCGCAACCCCTGTTGCCAGTTACCAGCACGTGAAGGTGGGGACTCTGG CGAGACTGCCCAGATCAACTGGGAGGAAGGTGGGGACGACGTCAGGT CAGTATGGCCCTTATGCCCAGGGCTGCACACGTACTACAATGCCCAGT ACAGAGGGGGCCGAAGCCGCGAGGCGGAGGAAATCCTAAAAACTGG GCCCAGTTCGGACTGTAGGCTGCAACCCGCCTACACGAAGCCGGAATC GCTAGTAATGGCGCATCAGCTACGGCGCCGTGAATACGTTCCCGGGTC TTGTACACACCGCCCGTCACATCATGGAAGCCGGTCGCACCCGAAGTA TCTGAAGCCAACCGCAAGGAGGCAGGGTCCTAAGGTGAGACTGGTAA CTGGGATGAAGTCGTAACAAGGTAGCCGTAGGGGAACCTGCGGCTGG ATCACCTCCTTTC |
| 5 | Akkermansia muciniphila Isolate 5 | TCCAGCAATTTCAAAAATTAATTTGATGGAGAGTTTGATTCTGGCTCA GAACGAACGCTGGCGGCGTGGATAAGACATGCAAGTCGAACGAGAGA ATTGCTAGCTTGCTAATAATTCTCTAGTGGCGCACGGGTGAGTAACAC GTGAGTAACCTGCCCCCGAGAGCGGGATAGCCCTGGGAAACTGGGAT TAATACCGCATAGTATCGCAAGATTAAAGCAGCAATGCGCTTGGGGAT GGGCTCGCGGCCTATTAGTTAGTTGGTGAGGTAACGGCTCACCAAGGC GATGACGGGTAGCCGGTCTGAGAGGATGTCCGGCCACACTGGAACTG AGACACGGTCCAGACACCTACGGGTGGCAGCAGTCGAGAATCATTCA CAATGGGGGAAACCCTGATGGTGCGACGCCGCGTGGGGAATGAAGG TCTTCGGATTGTAAACCCCTGTCATGTGGGAGCAAATTAAAAAGATAG TACCACAAGAGGAAGAGACGGCTAACTCTGTGCCAGCAGCCGCGGTA ATACAGAGGTCTCAAGCGTTGTTCGGAATCACTGGGCGTAAAGCGTGC GTAGGCTGTTTCGTAAGTCGTGTGTGAAAGGCGCGGGCTCAACCCGCG GACGGCACATGATACTGCGAGACTAGAGTAATGGAGGGGAACCGGA ATTCTCGGTGTAGCAGTGAAATGCGTAGATATCGAGAGGAACACTCGT GGCGAAGGCGGGTTCCTGGACATTAACTGACGCTGAGGCACGAAGGC CAGGGGAGCGAAAGGGATTAGATACCCCTGTAGTCCTGGCAGTAAAC GGTGCACGCTTGGTGTGCGGGGAATCGACCCCCTGCGTGCCGGAGCTA ACGCGTTAAGCGTGCCGCCTGGGGAGTACGGTCGCAAGATTAAAACTC AAAGAAATTGACGGGGACCCGCACAAGCGGTGGAGTATGTGGCTTAA TTCGATGCAACGCGAAGAACCTTACCTGGGCTTGACATGTAATGAACA ACATGTGAAAGCATGCGACTCTTCGGAGGCGTTACACAGGTGCTGCAT GGCCGTCGTCAGCTCGTGTCGTGAGATGTTTGGTTAAGTCCAGCAACG AGCGCAACCCCTGTTGCCAGTTACCAGCACGTGAAGGTGGGGACTCTG GCGAGACTGCCCAGATCAACTGGGAGGAAGGTGGGGACGACGTCAGG TCAGTATGGCCCTTATGCCCAGGGCTGCACACGTACTACAATGCCCAG TACAGAGGGGCCGAAGCCGCGAGGCGGAGGAAATCCTAAAAACTGG GCCCAGTTCGGACTGTAGGCTGCAACCCGCCTACACGAAGCCGGAATC GCTAGTAATGGCGCATCAGCTACGGCGCCGTGAATACGTTCCCGGGTC TTGTACACACCGCCCGTCACATCATGGAAGCCGGTCGCACCCGAAGTA TCTGAAGCCAACCGCAAGGAGGCAGGGTCCTAAGGTGAGACTGGTAA CTGGGATGAAGTCGTAACAAGGTAGCCGTAGGGGAACCTGCGGCTGG ATCACCTCCTTTCTNNNNNNATGGAGCAAGTA |
| 6 | Akkermansia muciniphila Isolate 6 | GAGTTTGATTCTGGCTCAGAACGAACGCTGGCGGCGTGGATAAGACAT GCAAGTCGAACGAGAGAATTGCTAGCTTGCTAATAATTCTCTAGTGGC GCACGGGTGAGTAACACGTGAGTAACCTGCCCCCGAGAGCGGGATAG CCCTGGGAAACTGGGATTAATACCGCATAGTATCGAAAGATTAAAGCA GCAATGCGCTTGGGGATGGGCTCGCGGCCTATTAGTTAGTTGGTGAGG TAACGGCTCACCAAGGCGATGACGGGTAGCCGGTCTGAGAGGATGTC CGGCCACACTGGAACTGAGACACGGTCCAGACACCTACGGGTGGCAG |

TABLE 5-continued

Illustrative mucin-degrading microbes

| SEQ ID NO. | Strain/Isolate | Sequence |
|---|---|---|
| | | CAGTCGAGAATCATTCACAATGGGGGAAACCCTGATGGTGTGACGCC<br>GCGTGGGGGAATGAAGGTCTTCGGATTGTAAACCCCTGTCATGTGGGA<br>GCAAATTAAAAAGATAGTACCACAAGAGGAAGAGACGGCTAACTCTG<br>TGCCAGCAGCCGCGGTAATACAGAGGTCTCAAGCGTTGTTCGGAATCA<br>CTGGGCGTAAAGCGTGCGTAGGCTGTTTCGTAAGTCGTGTGTGAAAGG<br>CGCGGGCTCAACCCGCGGACGGCACATGATACTGCGAGACTAGAGTA<br>ATGGAGGGGGAACCGGAATTCTCGGTGTAGCAGTGAAATGCGTAGAT<br>ATCGAGAGGAACACTCGTGGCGAAGGCGGGTTCCTGGACATTAACTG<br>ACGCTGAGGCACGAAGGCCAGGGGAGCGAAAGGGATTAGATACCCCT<br>GTAGTCCTGGCAGTAAACGGTGCACGCTTGGTGTGCGGGGAATCGACC<br>CCCTGCGTGCCGGAGCTAACGCGTTAAGCGTGCCGCCTGGGGAGTACG<br>GTCGCAAGATTAAAACTCAAAGAAATTGACGGGGACCCGCACAAGCG<br>GTGGAGTATGTGGCTTAATTCGATGCAACGCGAAGAACCTTACCTGGG<br>CTTGACATGTAATGAACAACATGTGAAAGCATGCGACTCTTCGGAGGC<br>GTTACACAGGTGCTGCATGGCCGTCGTCAGCTCGTGTCGTGAGATGTT<br>TGGTTAAGTCCAGCAACGAGCGCAACCCCTGTTGCCAGTTACCAGCAC<br>GTGAAGGTGGGGACTCTGGCGAGACTGCCCAGATCAACTGGGAGGAA<br>GGTGGGGACGACGTCAGGTCAGTATGGCCCTTATGCCCAGGGCTGCAC<br>ACGTACTACAATGCCCAGTACAGAGGGGGCCGAAGCCGCGAGGCGGA<br>GGAAATCCTGAAAACTGGGCCCAGTTCGGACTGTAGGCTGCAACCCGC<br>CTACACGAAGCCGGAATCGCTAGTAATGGCGCATCAGCTACGGCGCC<br>GTGAATACGTTCCCGGGTCTTGTACACACCGCCCGTCACATCATGGAA<br>GCCGGTCGCACCCGAAGTATCTGAAGCCAACCGCAAGGAGGCAGGGT<br>CCTAAGGTGAGACTGGTAACTGGGATGAAGTCGTAACAAGGTAGCCG<br>TAGGGGAACCTGCGGCTGGATCACCTCCTTTCTA |

Example 5: Short-Chain Fatty Acid Production

Figure 11:
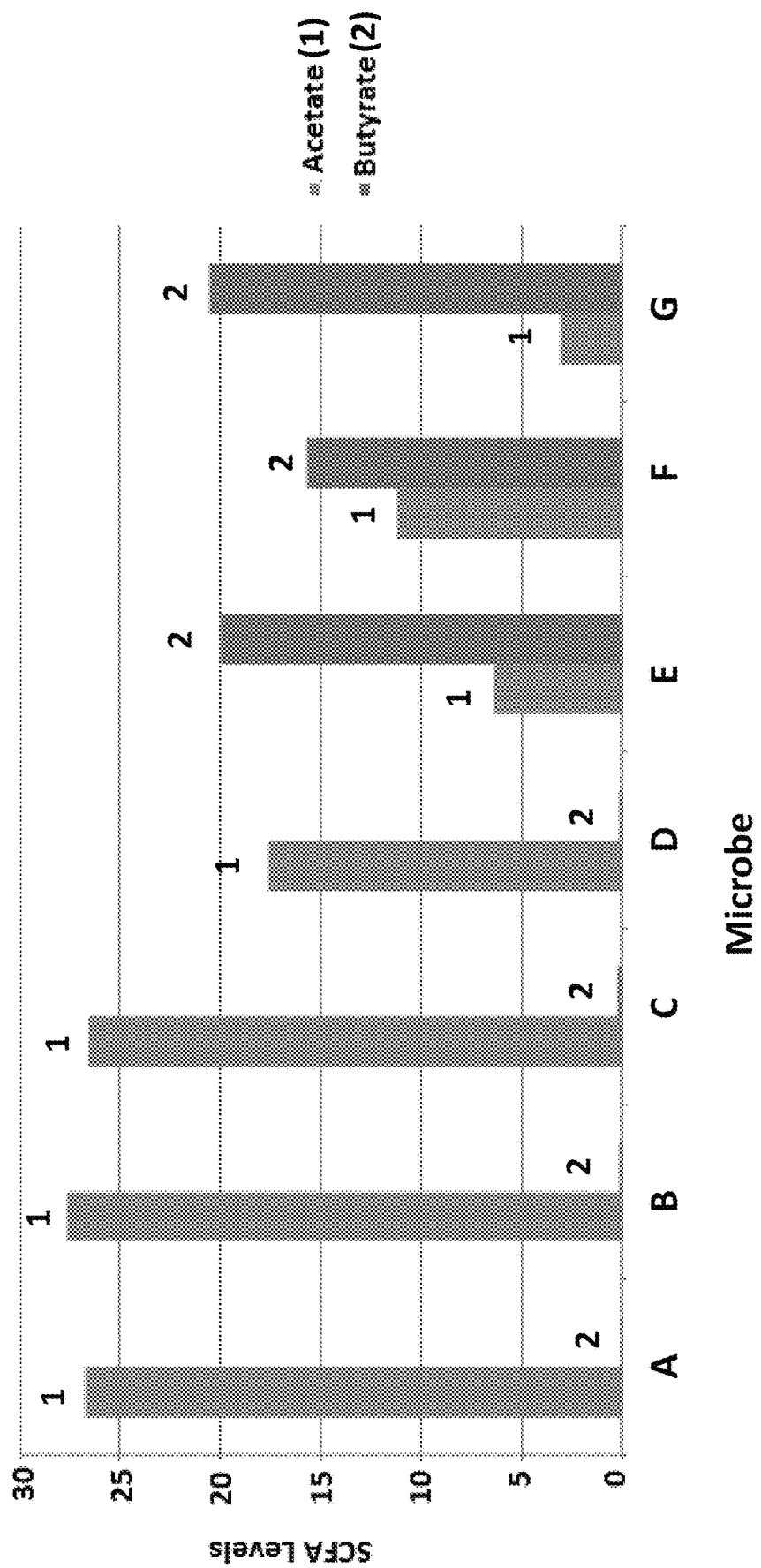
FIG. 11 illustrates levels of short-chain fatty acids acetate and butyrate produced by microbes of the disclosure.

FIG. 11 illustrates short chain fatty acid levels produced by microbes of the disclosure. The short chain fatty acid produced by each microbe shows that the predicted genomic function of the microbes matches the actual function. Microbes A-D primarily produced acetate which can serve as a substrate for butyrate production by a butyrate-producing microbe (e.g., a butyrate intermediate). Microbes E, F, and G primarily produced butyrate. A combination of a first microbe producing a butyrate intermediate (e.g., any of microbes A-D) and a second microbe converting the intermediate to butyrate (e.g., any of microbes E-G) can be utilized for treating a condition. In one non-limiting example, strain A can be *Bifidobacterium adolescentis* (BADO). In one non-limiting example, strain B can be *Bifidobacterium infantis* (BINF). In one non-limiting example, strain C can be *Bifidobacterium longum* (BLON). In one non-limiting example, strain D can be *Clostridium indolis* (CIND). In one non-limiting example, strain E can be *Clostridium beijerinckii* (CBEI). In one non-limiting example, strain F can be *Clostridium butyricum* (CBUT). In one non-limiting example, strain G can be *Eubacterium hallii* (EHAL).

Example 6: Stability Studies for Microbial Composition

Figure 12:
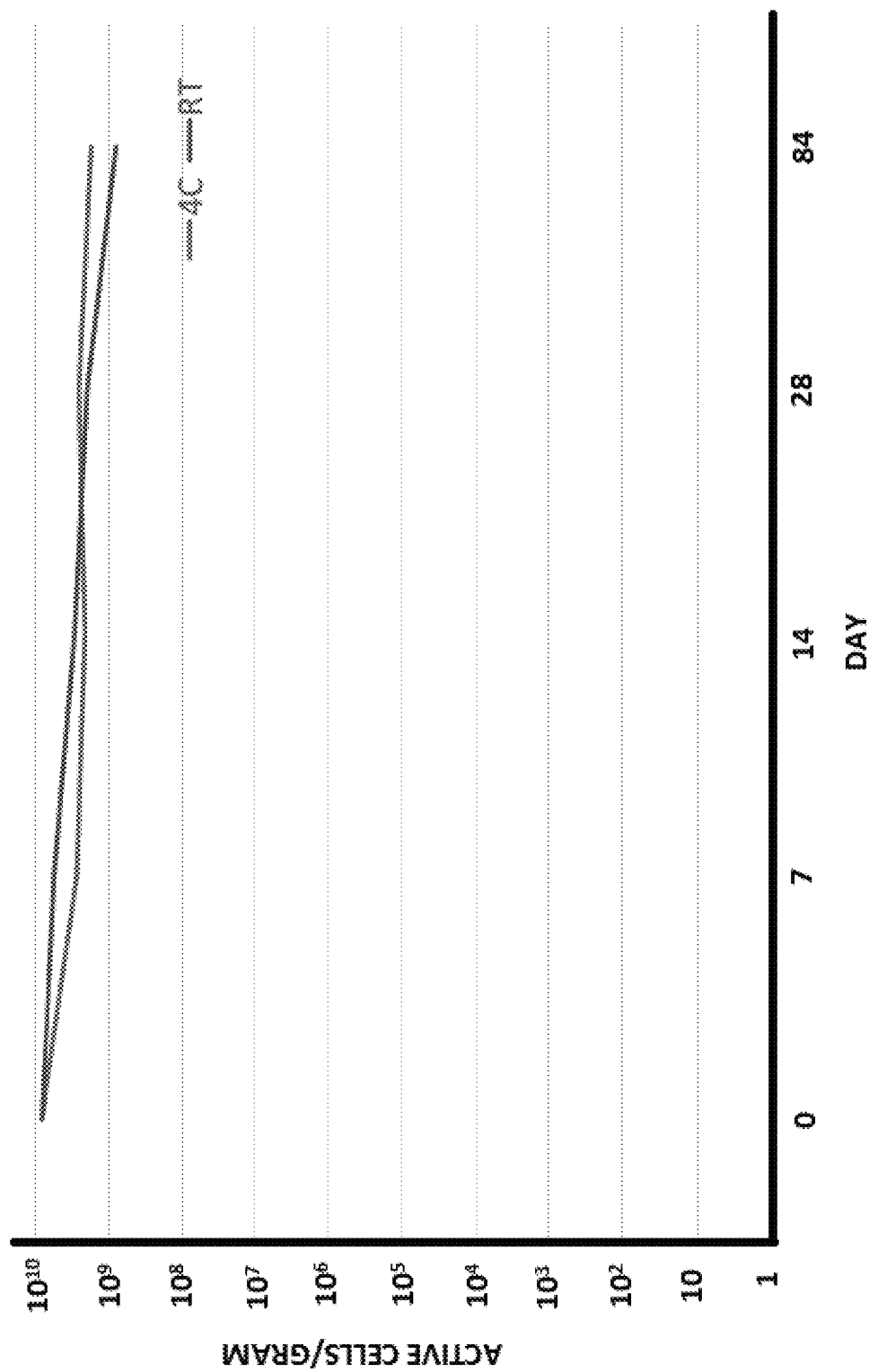
FIG. 12 depicts stability of an illustrative therapeutic composition. The therapeutic composition was stored in 4 degrees C. or at room temperature, and the active cells per gram present over time were measured and compared.

FIG. 12 illustrates stability data for a composition that comprises strictly anaerobic microbes (e.g., *Clostridium beijerinckii* and *Clostridium butyricum*) in a substantially dry form produced by lyophilization. The composition was stored in 4° C. or room temperature for 84 days, and the number of active cells within the composition was quantified by flow cytometry during the storage period. The data showed that the composition is stable for at least 84 days in both 4° C. and room temperature.

Example 7: Low Allergen Microbial Compositions

Provided herein are compositions with a reduced or negligible amount of allergens for patients allergic to, for example, soy, peanuts, shellfish, wheat, or milk. Such compositions can also be beneficial for disorders where these agents can act as irritants exacerbating the symptoms, for example, in Inflammatory Bowel Syndrome (IBS).

Table 6 shows allergen analysis for a microbial composition of the disclosure. The allergens are present in negligible amounts so as not cause an allergic reaction.

TABLE 6

Allergen Analysis

| Allergen Analysis | Results |
|---|---|
| Crustacean | <4.0 ppm |
| Peanut | <2.5 ppm |
| Soy | <2.5 ppm |
| Wheat (Gliadin-Gluten) | <5.0 ppm |

Example 8: Study to Evaluate Engraftment-Enhancing Microbial Compositions in Human Subjects Objective: The purpose of the study is to assess the effect of engraftment-enhancing microbial compositions of the disclosure in promoting engraftment of exogenously administered microbes in human subjects Methods: Thirty human subjects enter a double-blind, placebo controlled and randomized study.
1) Placebo group: Ten human subjects are administered a placebo composition lacking microbes.
2) Control Group: Ten human subjects are administered a control composition comprising at least one butyrate producing microbe but lacking a mucin-degrading microbe.

3) Experimental group: Ten human subjects are administered the experimental microbial composition comprising at least one butyrate-producing microbe and at least one mucin-degrading microbe.

For each group, the microbial composition is administered orally twice a day (e.g., prior to breakfast and prior to dinner) for 2 weeks. Gut microbiome profile (e.g., using stool sample analysis) of subjects in each group is evaluated before and after completion of treatment regimen.

Following treatment, subjects in the experimental group exhibit engraftment of both the exogenously administered mucin-degrading microbe and the exogenously administered butyrate-producing microbe. Additionally, the experimental group exhibits at least a 5% higher engraftment level of the butyrate-producing microbe as compared with the control group that do not receive the mucin-degrading microbe.

Example 9: Compositions to Promote Microbial Engraftment for Treatment of a Health Condition A subject is administered a microbial composition for treatment of a health condition (e.g., metabolic disorder, diabetes-type 1 or type 2, insulin resistance, inflammation, IBS, diarrhea, autism, depression, eczema, rashes) or for promoting good gut health (e.g., improve gut lining, reduce GI distress, restore healthy microbiome). The microbial composition comprises one or more butyrate-producing microbes. The microbial composition lacks a mucin-degrading microbe. Even after following the dosing regimen, the subject does not see any improvement in symptoms. Profiling of the subject's gut microbiome shows that the microbes in the composition did not engraft in the subject. The subject is administered another microbial composition that comprises a mucin-degrading microbe in addition to the other microbes that were in the previous composition. Upon starting this composition, the subject sees an improvement in symptoms. Profiling of the subject's gut microbiome after the dosing regimen is complete (e.g., after administration is ceased) shows that the exogenous microbes administered in the composition have successfully engrafted.

Example 10: Study to Evaluate Engraftment-Enhancing Microbial Compositions in Human Subjects Objective: The purpose of the study was to assess the effect of engraftment-enhancing microbial compositions of the disclosure in promoting engraftment of exogenously administered microbes in human subjects.

Methods: Human subjects entered a double-blind, placebo controlled and randomized study.

Placebo group: Human subjects were administered a placebo composition lacking microbes.

Control Group: Human subjects were administered a control composition comprising at least one butyrate producing microbe but lacking a mucin-degrading microbe for example, a composition comprising strains 5, 6, and 9, corresponding to, e.g., strains of *Clostridium beijerenckii, Clostridium butyricum*, and *Bifidobacterium infantis*, respectively Experimental group: Human subjects were administered the experimental microbial composition comprising at least one butyrate-producing microbe and at least one mucin-degrading microbe, for example, a composition comprising strains 1, 5, 6, 8, and 9, corresponding to, e.g., *Akkermansia muciniphila, Clostridium beijerenckii, Clostridium butyricum, Eubacterium hallii*, and *Bifidobacterium infantis*, respectively.

For each group, the microbial composition was orally administered twice a day (e.g., prior to breakfast and prior to dinner) at a dose of between $2.7 \times 10^9$ and $4.8 \times 10^{10}$ CFU of each microbial strain. Compositions were administered for 12 weeks, followed by a four week washout period where the microbial compositions were not administered. Subject gut microbiome profiles were evaluated via stool sample analysis before and during the treatment regimen, and after the four week washout period. Stool samples were collected at baseline, 4 weeks, 12 weeks, and 16 weeks (4 weeks after discontinuing administration of the compositions) to determine if the administered bacterial strains could be detected in feces and, if so, whether the strains persisted after composition administration ceased.

Stool samples were collected, immediately frozen, and maintained at a cold temperature until processing. Samples were resuspended in 50 mM Tris HCl buffer (pH 8.0) with 5 mM EDTA, homogenized for 5 minutes in a paddle homogenizer, and filtered through 280 μM mesh before being aliquoted and refrozen at −80° C. Frozen fecal samples were extracted using the DNeasy PowerSoil HTP 96 Kit and DNA content of specific target microbes measured in qPCR reactions using primer pairs specifically designed for the detection of each strain. Duplicate eight point standard curves were run each with three technical replicates by diluting known quantities of purified genomic DNA from target organisms. These standard curves were used to relate threshold cycle (Ct) values to mass of DNA of target organism for each sample.

Butyrate-producing microbes persisted through the washout period in a greater proportion of subjects in the experimental group than the control group, demonstrating engraftment of the butyrate-producing microbes was enhanced when the butyrate-producing microbes were administered with a mucin-degrading microbe. The mucin-degrading microbe also engrafted in some subjects.

Figure 13:
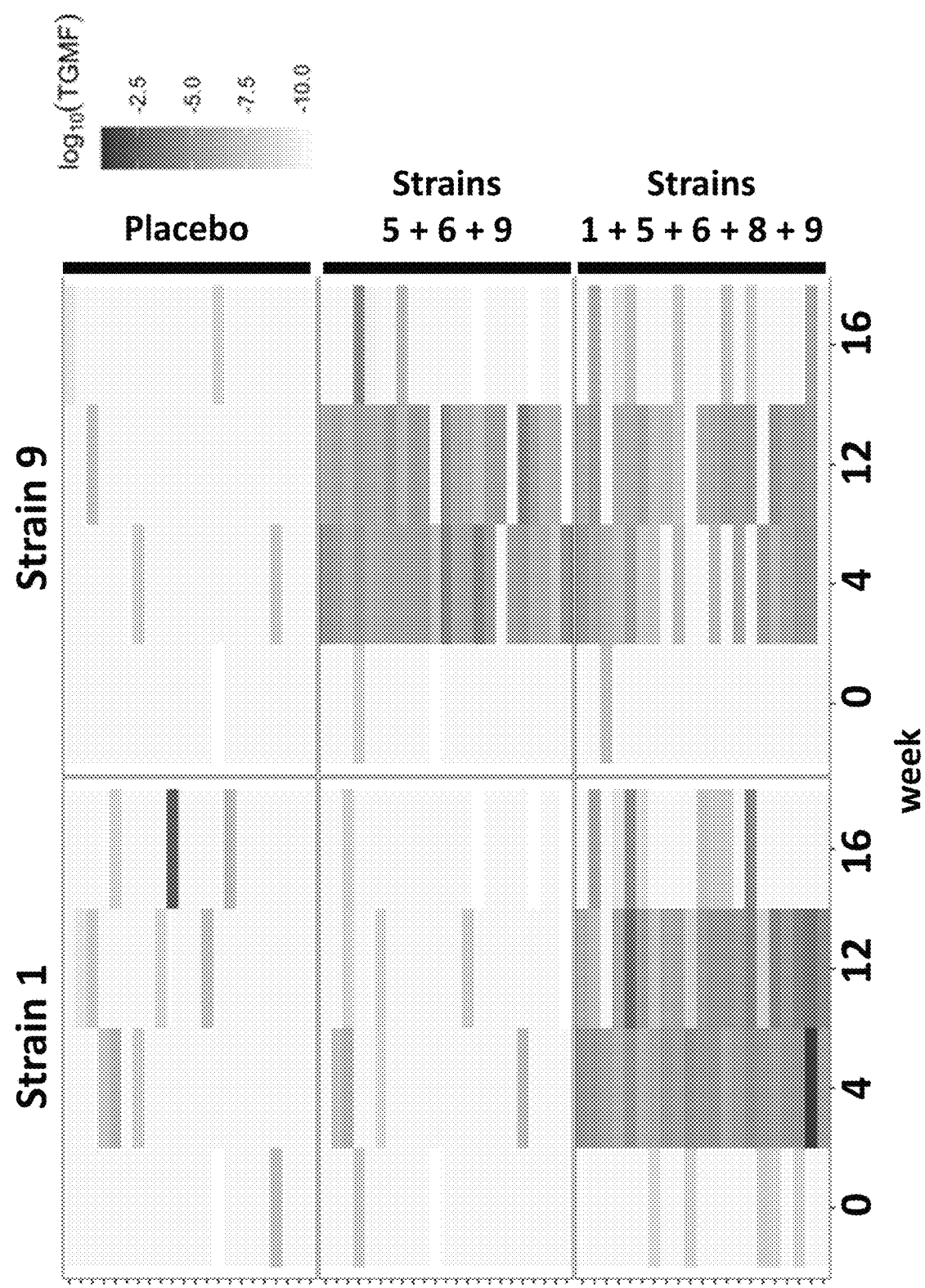
FIG. 13 illustrates data from a human study to evaluate engraftment of a microbial composition of the disclosure. Strain 1 is a mucin-degrading microbe (e.g., *Akkermansia muciniphila*); strains 5, 6, 8, and 9 are butyrate-producing microbes (e.g., *Clostridium beijerenckii, Clostridium butyricum, Eubacterium hallii*, and *Bifidobacterium infantis*, respectively). Subjects were administered a placebo (topmost panel), a composition of the disclosure comprising only butyrate-producing microbes (strains 5, 6, and 9, corresponding to, e.g., strains of *Clostridium beijerenckii, Clostridium butyricum*, and *Bifidobacterium infantis*, respectively; middle panel), or a composition of the disclosure comprising butyrate-producing microbes (strains 5, 6, 8, and 9, corresponding to, e.g., strains of *Clostridium beijerenckii, Clostridium butyricum, Eubacterium hallii*, and *Bifidobacterium infantis*, respectively) and a mucin-degrading microbe (strain 1, corresponding to, e.g., *Akkermansia muciniphila*) (bottom panel) for 12 weeks, followed by a four week washout period. Each rectangle represents the relative abundance of the strain's genome in a stool sample as indicated in the scale. Of subjects administered only the butyrate-producing microbes, only two subjects lacking strain 9 at baseline (week 0) exhibited engraftment of strain 9 at washout (week 16). Of subjects administered the butyrate-producing microbes and the mucin-degrading microbe, seven subjects lacking strain 9 at baseline exhibited engraftment of strain 9 at washout, indicating enhanced engraftment of butyrate-producing microbes when administered together with a mucin-degrading microbe. TGMF=target genome mass fraction.

FIG. 13 illustrates engraftment of a butyrate-producing microbe when administered with a mucin-degrading microbe as part of a composition of the disclosure. Strain 1 is a mucin-degrading microbe (e.g., *Akkermansia muciniphila*); strains 5, 6, 8, and 9 are butyrate-producing microbes (e.g., *Clostridium beijerenckii, Clostridium butyricum, Eubacterium hallii*, and *Bifidobacterium infantis*, respectively). Subjects were administered a placebo (topmost panel), a composition of the disclosure comprising only butyrate-producing microbes (strains 5, 6, and 9, corresponding to, e.g., strains of *Clostridium beijerenckii, Clostridium butyricum*, and *Bifidobacterium infantis*, respectively; middle panel), or a composition of the disclosure comprising butyrate-producing microbes (strains 5, 6, 8, and 9, corresponding to, e.g., strains of *Clostridium beijerenckii, Clostridium butyricum, Eubacterium hallii*, and *Bifidobacterium infantis*, respectively) and a mucin-degrading microbe (strain 1, corresponding to, e.g., *Akkermansia muciniphila*) (bottom panel) for 12 weeks, followed by a four week washout period. Each rectangle represents the relative abundance of the strain's genome in a stool sample as indicated in the scale. Of subjects administered only the butyrate-producing microbes, only two subjects lacking strain 9 at baseline (week 0) exhibited engraftment of strain 9 at washout (week 16). Of subjects administered the butyrate-producing microbes and the mucin-degrading microbe, seven subjects lacking strain 9 at baseline exhibited engraftment of strain 9 at washout, indicating enhanced engraftment of butyrate-producing microbes when administered together with a mucin-degrading microbe. TGMF=target genome mass fraction.

Figure 14:
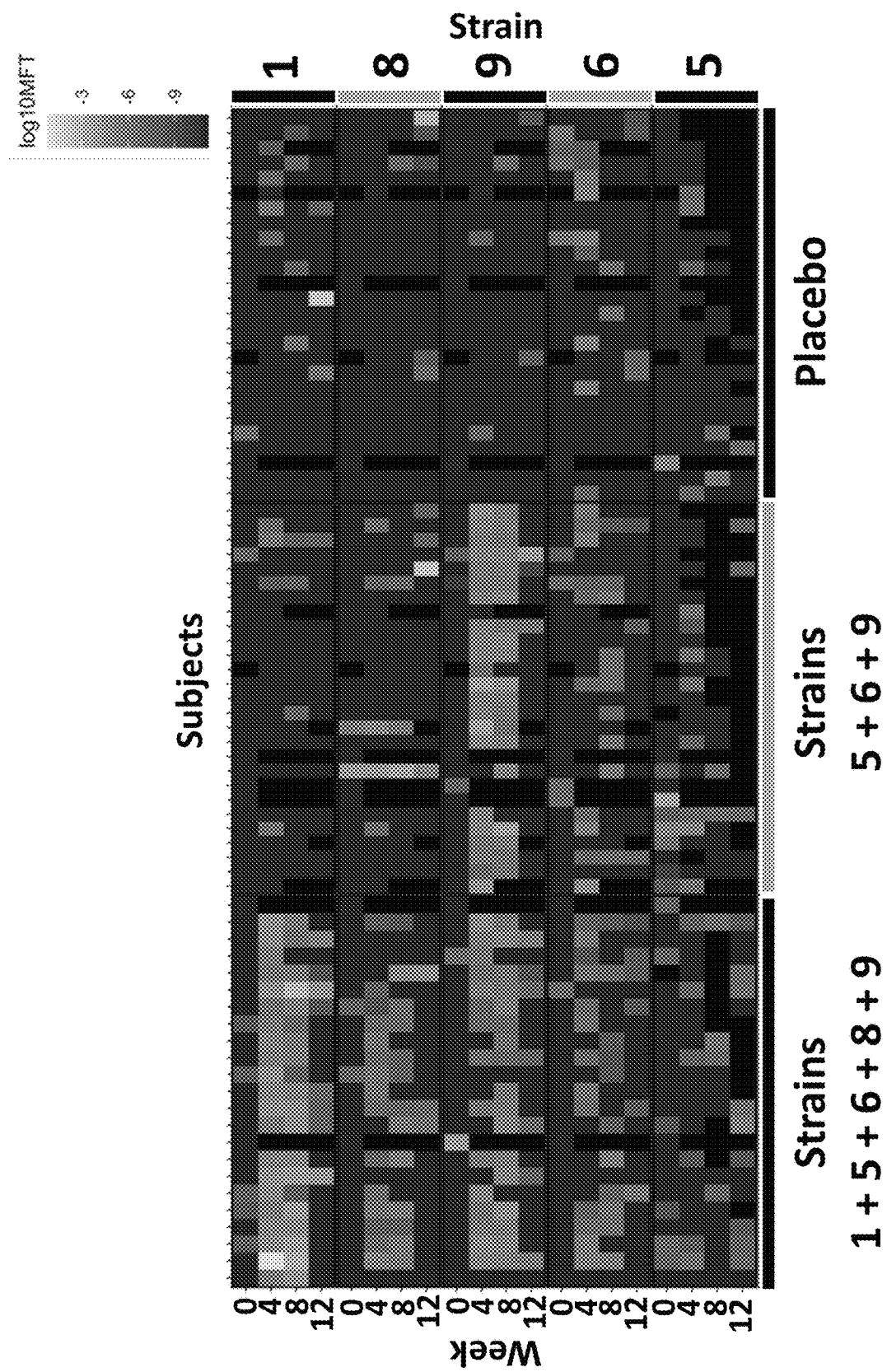
FIG. 14 illustrates data from a human study to evaluate engraftment of a microbial composition of the disclosure. Strain 1 is a mucin-degrading microbe (e.g., *Akkermansia muciniphila*); strains 5, 6, 8, and 9 are butyrate-producing microbes (e.g., *Clostridium beijerenckii, Clostridium butyricum, Eubacterium hallii*, and *Bifidobacterium infantis*, respectively). Subjects were administered a placebo (right), a composition of the disclosure comprising only butyrate-producing microbes (strains 5, 6, and 9, corresponding to, e.g., strains of *Clostridium beijerenckii, Clostridium butyricum*, and *Bifidobacterium infantis*, respectively; middle), or a composition of the disclosure comprising butyrate-producing microbes (strains 5, 6, 8, and 9, corresponding to, e.g., strains of *Clostridium beijerenckii, Clostridium butyricum, Eubacterium hallii*, and *Bifidobacterium infantis*, respectively) and a mucin-degrading microbe (strain 1, corresponding to, e.g., *Akkermansia muciniphila*) (left) for 12 weeks, followed by a 4 week washout period. Each rectangle represents the relative abundance of the strain's genome in a stool sample as indicated in the scale. Of subjects administered only the butyrate-producing microbes, two subjects lacking strain 9 at baseline (week 0), two subjects lacking strain 6 at baseline, and two subjects lacking strain 5 at baseline exhibited engraftment of the respective strains at washout (week 12). Of subjects administered the butyrate-producing microbes and the mucin-degrading microbe, seven subjects lacking strain 9 at baseline, six subjects lacking strain 6 at baseline, and six subjects lacking strain 5 at baseline exhibited engraftment of the respective strains at washout. These data indicate enhanced engraftment of butyrate-producing microbes when administered together with a mucin-degrading microbe.

FIG. 14 illustrates engraftment of butyrate-producing microbes when administered with a mucin-degrading microbe as part of a composition of the disclosure. Strain 1 is a mucin-degrading microbe (e.g., *Akkermansia muciniphila*); strains 5, 6, 8, and 9 are butyrate-producing microbes (e.g., *Clostridium beijerenckii, Clostridium butyricum, Eubacterium hallii*, and *Bifidobacterium infantis*, respectively). Subjects were administered a placebo (right), a composition of the disclosure comprising only butyrate-producing microbes (strains 5, 6, and 9, corresponding to, e.g., strains of *Clostridium beijerenckii, Clostridium butyricum*, and *Bifidobacterium infantis*, respectively; middle), or a composition of the disclosure comprising butyrate-producing microbes (strains 5, 6, 8, and 9, corresponding to, e.g., strains of *Clostridium beijerenckii, Clostridium butyricum, Eubacterium hallii*, and *Bifidobacterium infantis*, respectively) and a mucin-degrading microbe (strain 1, corresponding to, e.g., *Akkermansia muciniphila*) (left) for 12 weeks, followed by a 4 week washout period. Each rectangle represents the relative abundance of the strain's genome in a stool sample obtained at a certain time (week, left Y axis) as indicated in the scale. Of subjects administered only the butyrate-producing microbes, two subjects lacking strain 9 at baseline (week 0), two subjects lacking strain 6 at baseline, and two subjects lacking strain 5 at baseline exhibited engraftment of the respective strains at washout (week 12). Of subjects administered the butyrate-producing microbes and the mucin-degrading microbe, seven subjects lacking strain 9 at baseline, six subjects lacking strain 6 at baseline, and six subjects lacking strain 5 at baseline exhibited engraftment of the respective strains at washout. These data indicate enhanced engraftment of butyrate-producing microbes when administered together with a mucin-degrading microbe.

Figure 15A:
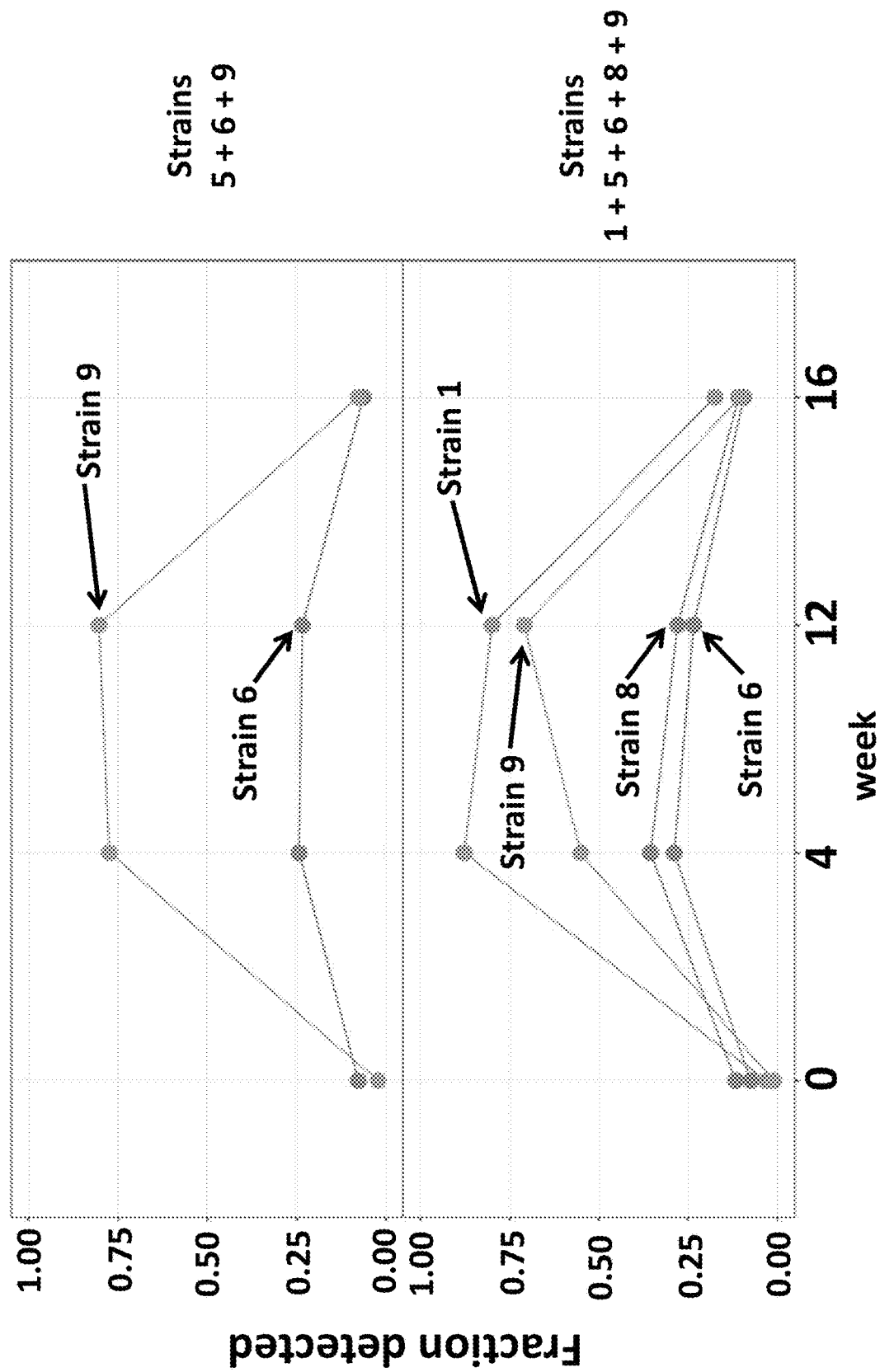
FIGS. 15A-B illustrate data from a human study to evaluate engraftment of a microbial composition of the disclosure. Strain 1 is a mucin-degrading microbe (e.g., *Akkermansia muciniphila*); strains 5, 6, 8, and 9 are butyrate-producing microbes (e.g., *Clostridium beijerenckii, Clostridium butyricum, Eubacterium hallii*, and *Bifidobacterium infantis*, respectively). Subjects were administered a composition of the disclosure comprising only butyrate-producing microbes (strains 5, 6, and 9, corresponding to, e.g., *Clostridium beijerenckii, Clostridium butyricum*, and *Bifidobacterium infantis*, respectively; top panel), or a composition of the disclosure comprising butyrate-producing microbes (strains 5, 6, 8, and 9, corresponding to, e.g., strains of *Clostridium beijerenckii, Clostridium butyricum, Eubacterium hallii*, and *Bifidobacterium infantis*, respectively) and a mucin-degrading microbe (strain 1, corresponding to, e.g., *Akkermansia muciniphila*) (bottom panel) for 12 weeks, followed by a 4 week washout period. Subjects' stool samples were processed and the presence of the strains detected by qPCR.
Figure 15B:
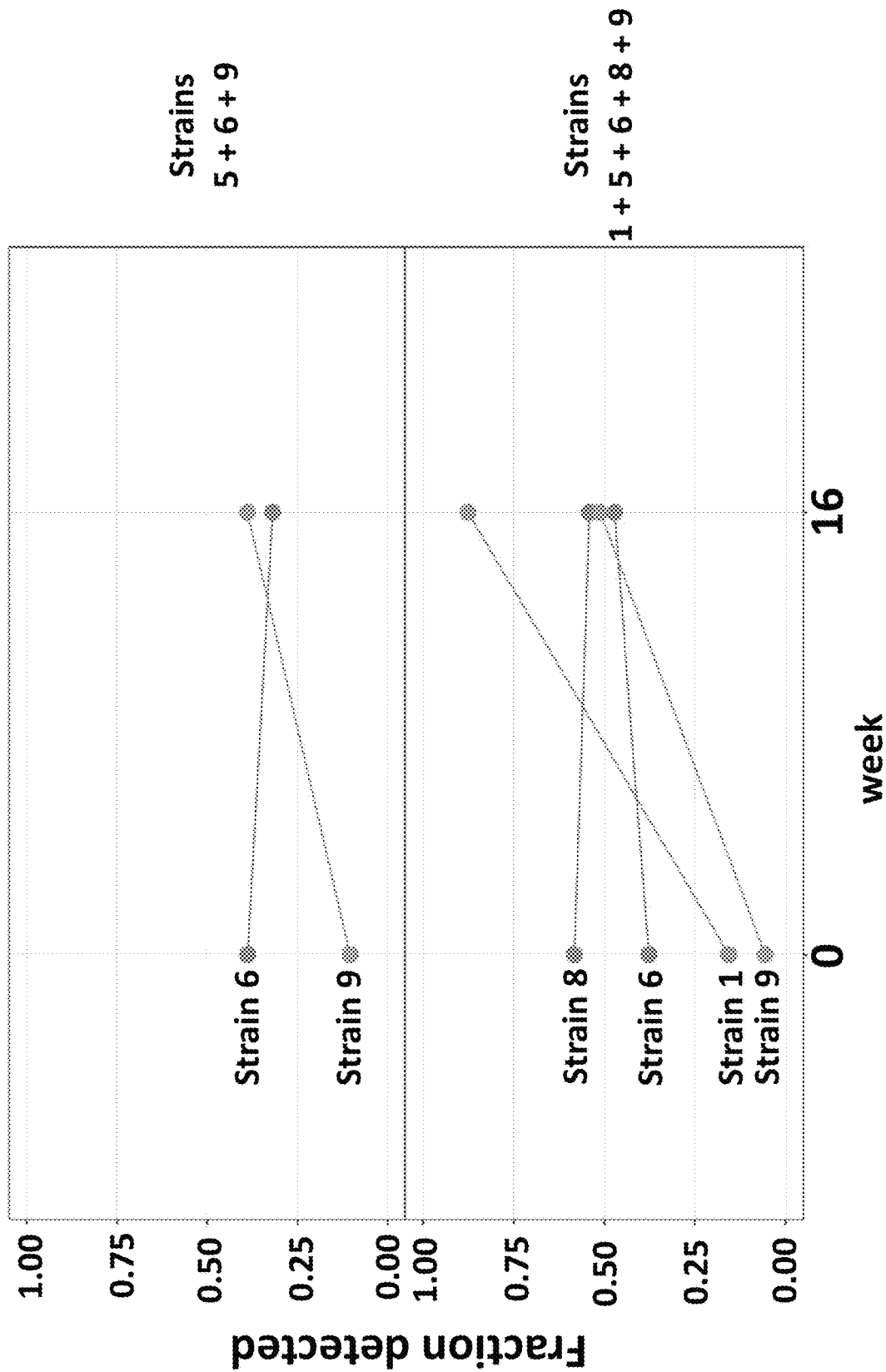

FIGS. 15A-B illustrate engraftment of butyrate-producing microbes when administered with a mucin-producing microbe as part of a composition of the disclosure. Strain 1 is a mucin-degrading microbe (e.g., *Akkermansia muciniphila*); strains 5, 6, 8, and 9 are butyrate-producing microbes (e.g., *Clostridium beijerenckii, Clostridium butyricum, Eubacterium hallii*, and *Bifidobacterium infantis*, respectively). Subjects were administered a composition of the disclosure comprising only butyrate-producing microbes (strains 5, 6, and 9, corresponding to, e.g., *Clostridium beijerenckii, Clostridium butyricum*, and *Bifidobacterium infantis*, respectively; top panel), or a composition of the disclosure comprising butyrate-producing microbes (strains 5, 6, 8, and 9, corresponding to, e.g., strains of *Clostridium beijerenckii, Clostridium butyricum, Eubacterium hallii*, and *Bifidobacterium infantis*, respectively) and a mucin-degrading microbe (strain 1, corresponding to, e.g., *Akkermansia muciniphila*) (bottom panel) for 12 weeks, followed by a 4 week washout period. Subjects' stool samples were processed and the presence of the strains was detected by qPCR. FIG. 15A shows the fraction qPCR reactions in which the indicated strains were detected at baseline (week 0), week 4 of administration, week 12 of administration, and following a 4 week washout period (week 16). FIG. 15B indicates the fraction qPCR reactions in which the indicated strains were detected at baseline (week 0), and following the washout period (week 16).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of increasing engraftment of *Eubacterium hallii* in the gut of a mammalian subject, the method comprising:

administering to the gut of the mammalian subject *Eubacterium hallii* and *Akkermansia muciniphila*; and measuring increased engraftment of *Eubacterium hallii* in the gut of the subject.

2. The method according to claim 1, wherein the engraftment is increased by at least about 5%.

3. The method according to claim 1, wherein the increased engraftment is measured by measuring an increased relative abundance of the at least one butyrate producing microbe *Eubacterium hallii* in the subject for more than 4 weeks after administration has ceased.

4. The method according to claim 1, wherein the *Eubacterium hallii* only engrafts in a presence of *Akkermansia muciniphila*.

5. The method according to claim 1, wherein the *Eubacterium hallii* and *Akkermansia muciniphila* are formulated for oral delivery.

6. The method according to claim 1, further comprising administering a prebiotic.

7. The method according to claim 6, wherein the prebiotic is inulin.

* * * * *